(12) United States Patent
Okawa et al.

(10) Patent No.: US 7,129,472 B1
(45) Date of Patent: Oct. 31, 2006

(54) OPTICAL SCANNING PROBE SYSTEM

(75) Inventors: Atsushi Okawa, Hachioji (JP); Hiroki Hibino, Hachioji (JP); Hiroyuki Sangu, Akishima (JP)

(73) Assignee: Olympus Corporation, Tokyo (JP)

( * ) Notice: Subject to any disclaimer, the term of this patent is extended or adjusted under 35 U.S.C. 154(b) by 819 days.

(21) Appl. No.: 09/857,614

(22) PCT Filed: Oct. 4, 2000

(86) PCT No.: PCT/JP00/06901

§ 371 (c)(1),
(2), (4) Date: Jun. 6, 2001

(87) PCT Pub. No.: WO01/24686

PCT Pub. Date: Apr. 12, 2001

(30) Foreign Application Priority Data

Oct. 6, 1999 (JP) .............................. H11-285963
Sep. 26, 2000 (JP) .............................. 2000-292546

(51) Int. Cl.
*H01J 5/16* (2006.01)
*G02B 21/00* (2006.01)
*G02B 26/08* (2006.01)

(52) U.S. Cl. .................. 250/234; 250/216; 250/227.2; 359/201

(58) Field of Classification Search ............. 250/201.3, 250/216, 227.2, 234–236; 359/201, 202, 359/223, 224, 368, 385; 600/173, 425, 476
See application file for complete search history.

(56) References Cited

U.S. PATENT DOCUMENTS

| | | | |
|---|---|---|---|
| 4,500,204 A * | 2/1985 | Ogura ........................ 356/318 |
| 4,619,249 A | 10/1986 | Landry | |
| 4,900,252 A * | 2/1990 | Liefke et al. ................. 433/27 |
| 5,120,953 A | 6/1992 | Harris | |
| 5,557,544 A * | 9/1996 | Simon et al. ................. 702/77 |
| 5,634,790 A * | 6/1997 | Pathmanabhan et al. ...... 433/29 |
| 5,691,635 A * | 11/1997 | Pot et al. .................... 324/115 |
| 5,742,419 A | 4/1998 | Dickensheets et al. | |
| 5,892,458 A * | 4/1999 | Anderer et al. .......... 340/10.41 |
| 5,952,562 A | 9/1999 | Yagi et al. | |
| 6,038,022 A * | 3/2000 | Jones et al. ................. 356/326 |
| 6,398,549 B1 * | 6/2002 | Koivisto et al. .............. 433/29 |
| 6,483,626 B1 * | 11/2002 | Suga ........................ 359/212 |
| 6,795,181 B1 * | 9/2004 | McCallum et al. ......... 356/326 |
| 2001/0043383 A1 * | 11/2001 | Suga ........................ 359/212 |

FOREIGN PATENT DOCUMENTS

| | | |
|---|---|---|
| JP | 1-297044 | 11/1989 |
| JP | 4-409 | 1/1992 |
| JP | 5-136953 | 6/1993 |
| JP | 5-344764 | 12/1993 |
| JP | 6-281445 | 10/1994 |
| JP | 9-21970 | 1/1997 |

(Continued)

*Primary Examiner*—Stephone B. Allen
(74) *Attorney, Agent, or Firm*—Scully, Scott, Murphy & Presser, PC

(57) ABSTRACT

An identification circuit (131) recognizes optical probes (112A, 112B) of different scanning types that are connected to a light source unit (113) and a control device (114), the frequency of the drive signal of a control circuit (130) for driving a scanner inside the optical probe is varied by this recognition signal, corresponding drive signals are applied to the optical probes connected, the scanner of each probe is scanned, and two-dimensional optical information is imaged by an imaging device (115) and displayed on a monitor (116).

56 Claims, 34 Drawing Sheets

FOREIGN PATENT DOCUMENTS

| | | |
|---|---|---|
| JP | 9-145721 | 6/1997 |
| JP | 10-311949 | 11/1998 |
| WO | WO 90/00754 | 1/1990 |
| WO | WO 99/27865 | 6/1999 |

* cited by examiner

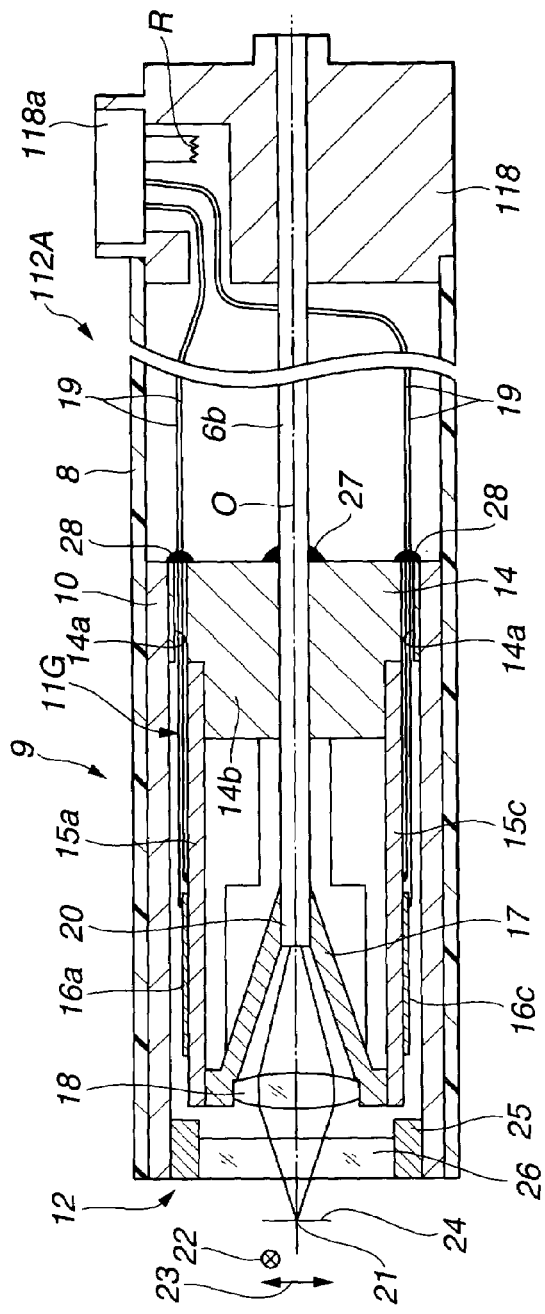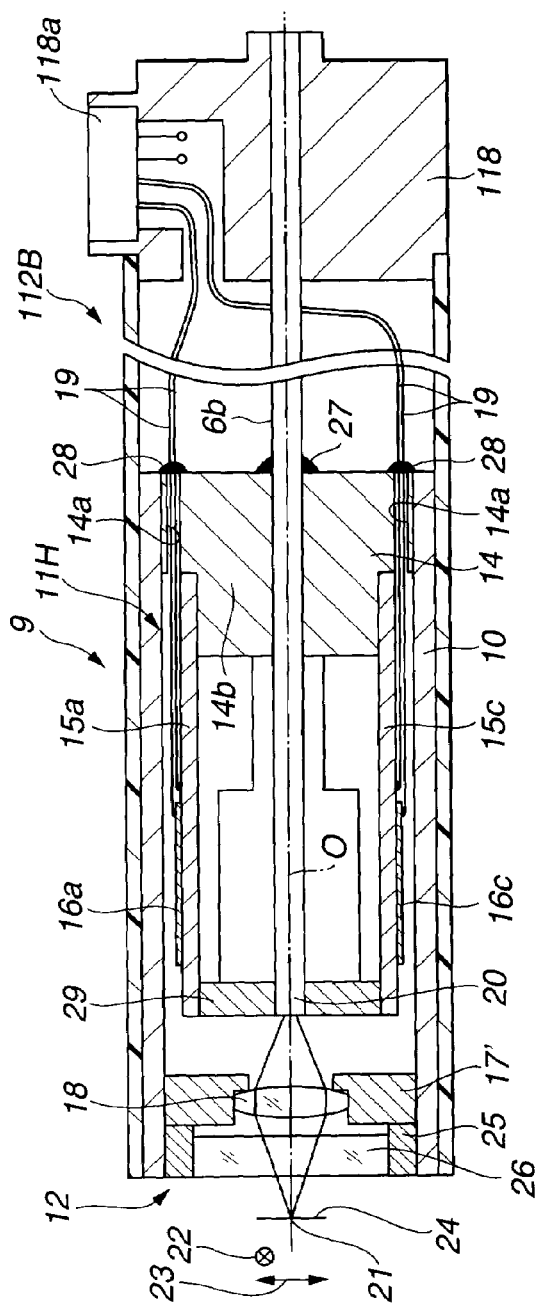

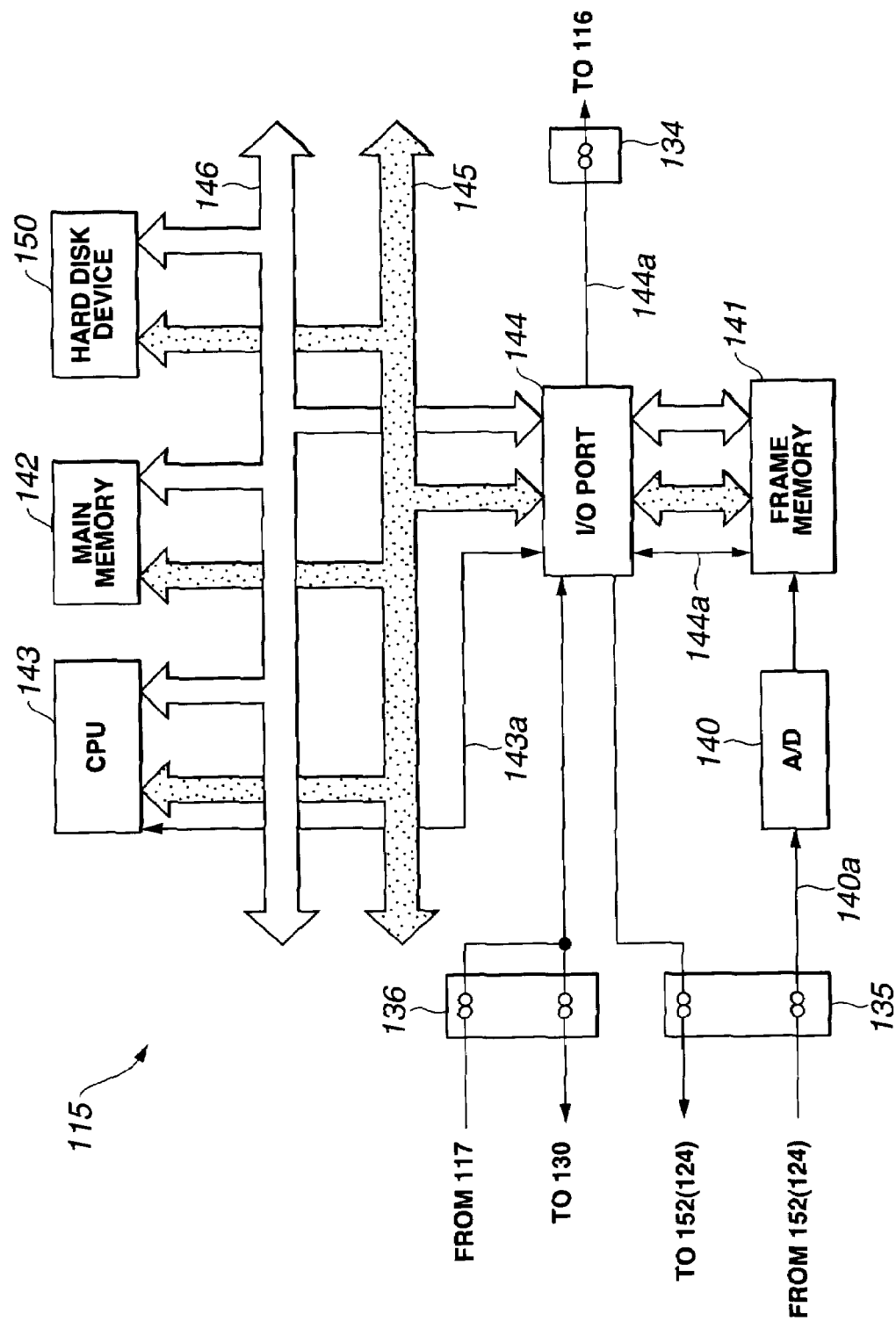

FIG.7A  FIG.7B
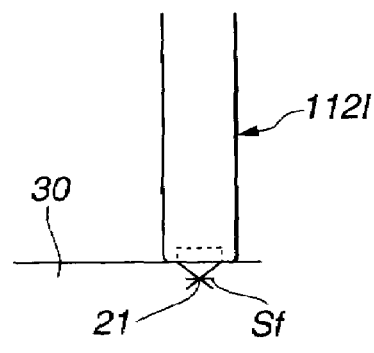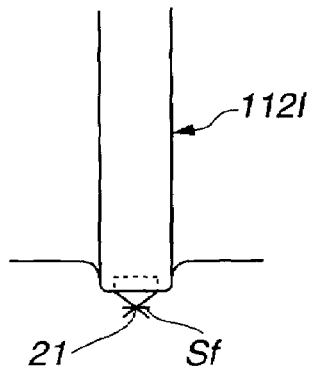
FIG.7C  FIG.7D
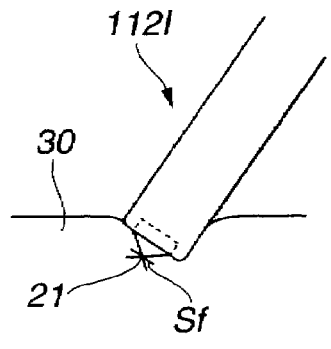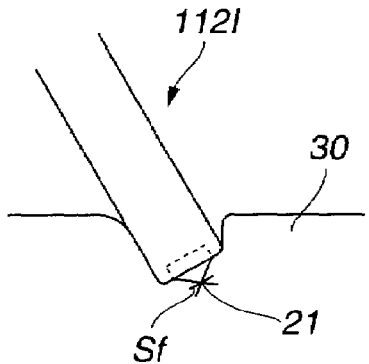
FIG.8
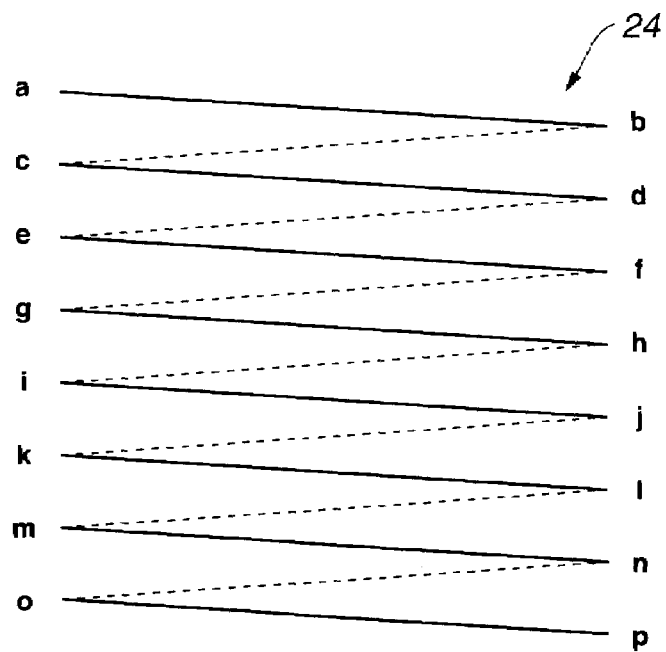

FIG.12A
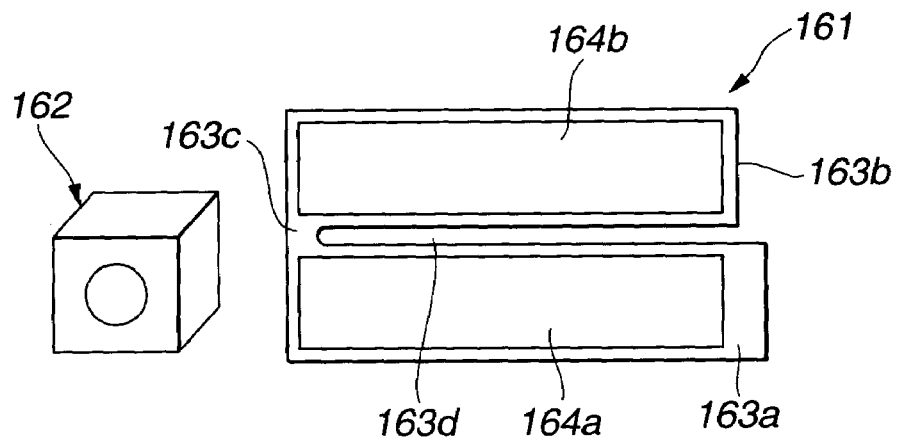
FIG.12D    FIG.12B
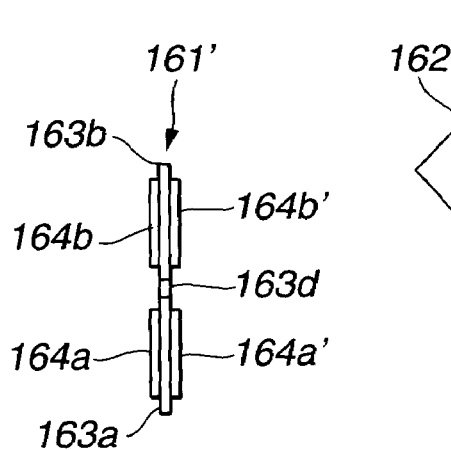    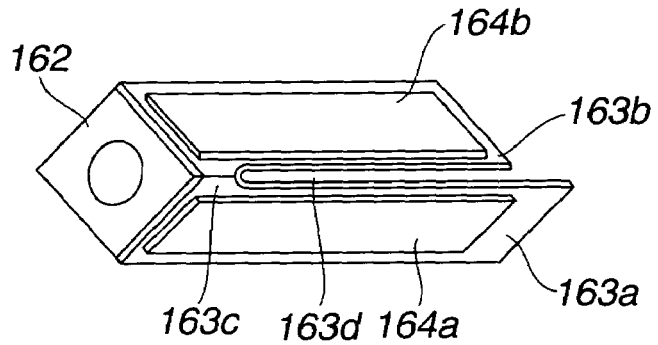
FIG.12C
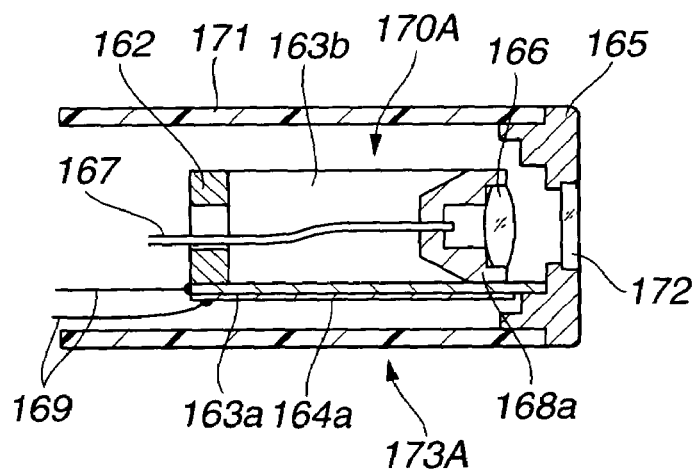

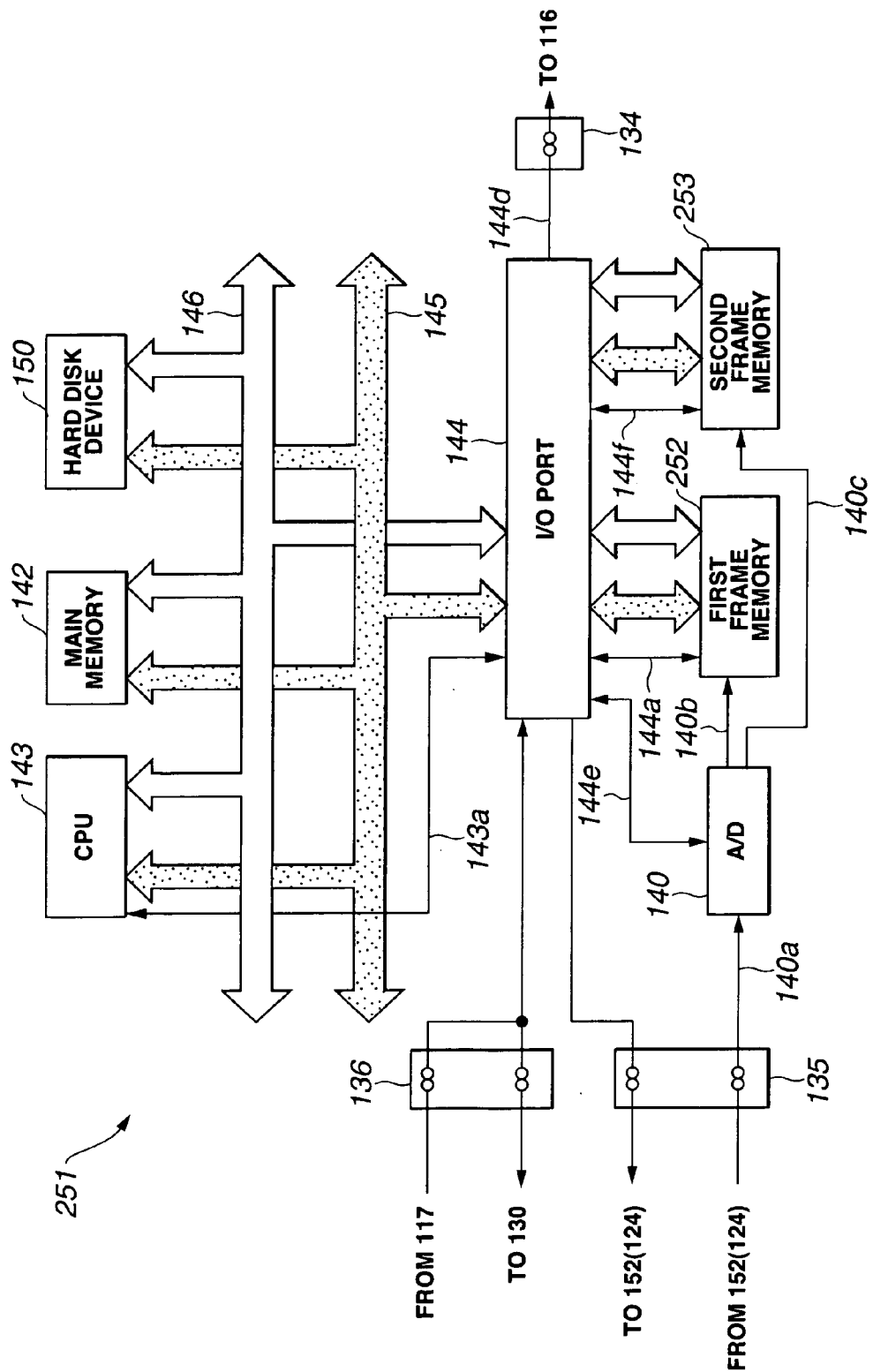

| APPLIED VOLTAGE V | DISPLACEMENT OF FORWARD PATH U(=f(V)) | CORRECTION COEFFICIENT α | DISPLACEMENT OF BACKWARD PATH U(=αf(V)) |
|---|---|---|---|
| ⋮ | ⋮ | ⋮ | ⋮ |

FIG.28
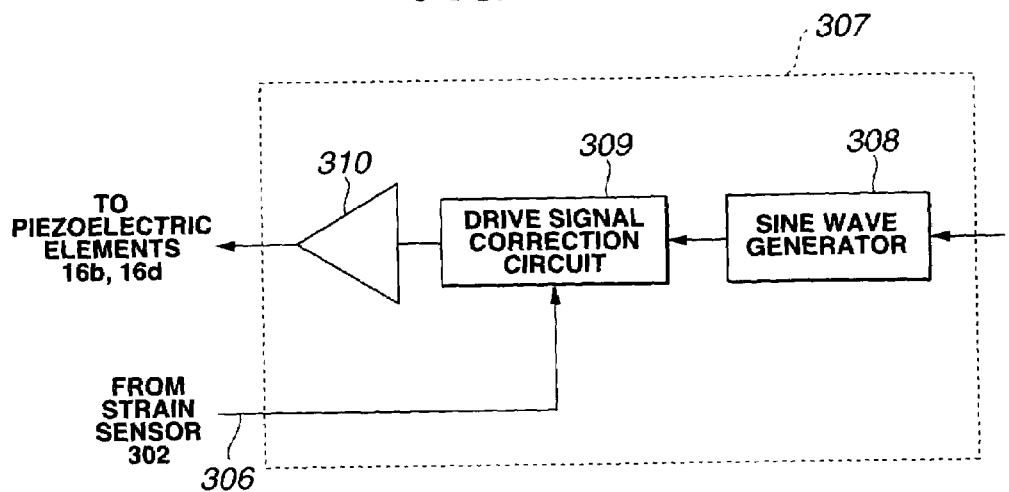
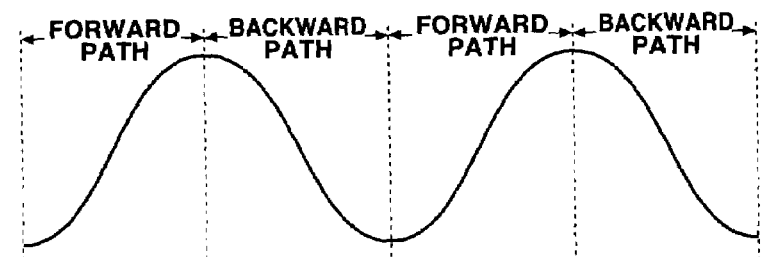
FIG.29A
SINE WAVE OUTPUT
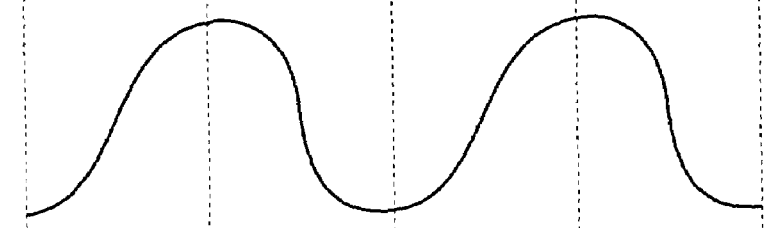
FIG.29B
SENSOR OUTPUT
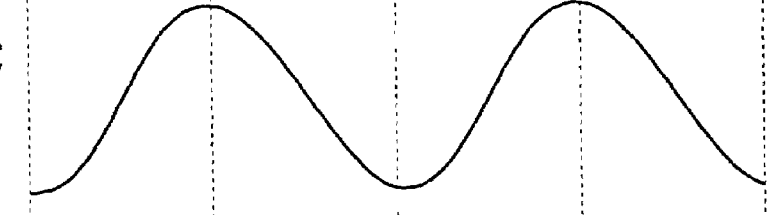
FIG.29C
CORRECTION SIGNAL OUTPUT
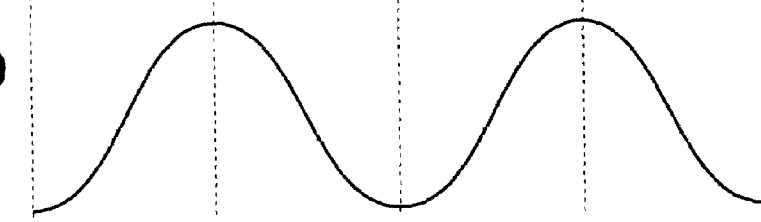
FIG.29D
SENSOR OUTPUT

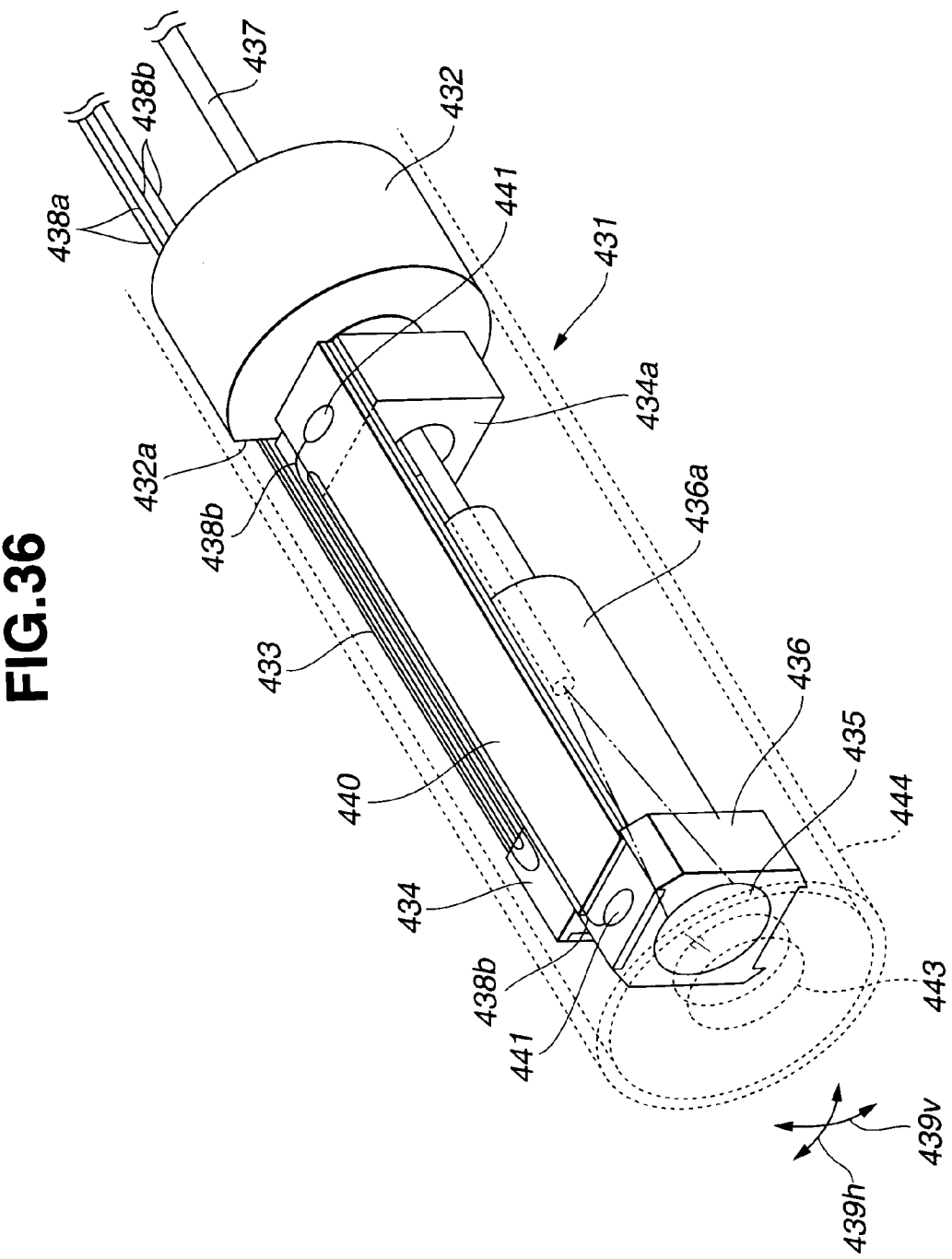

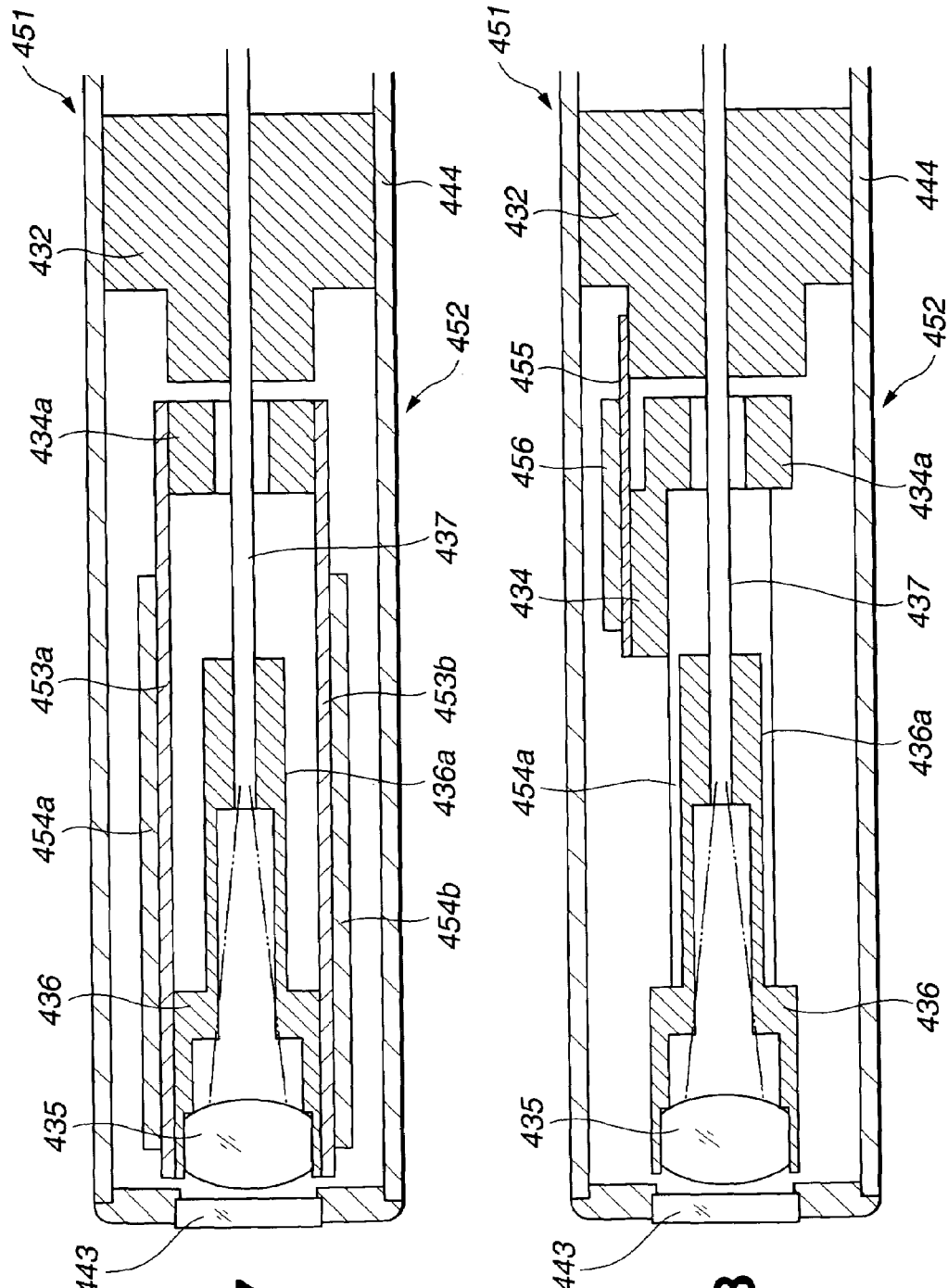

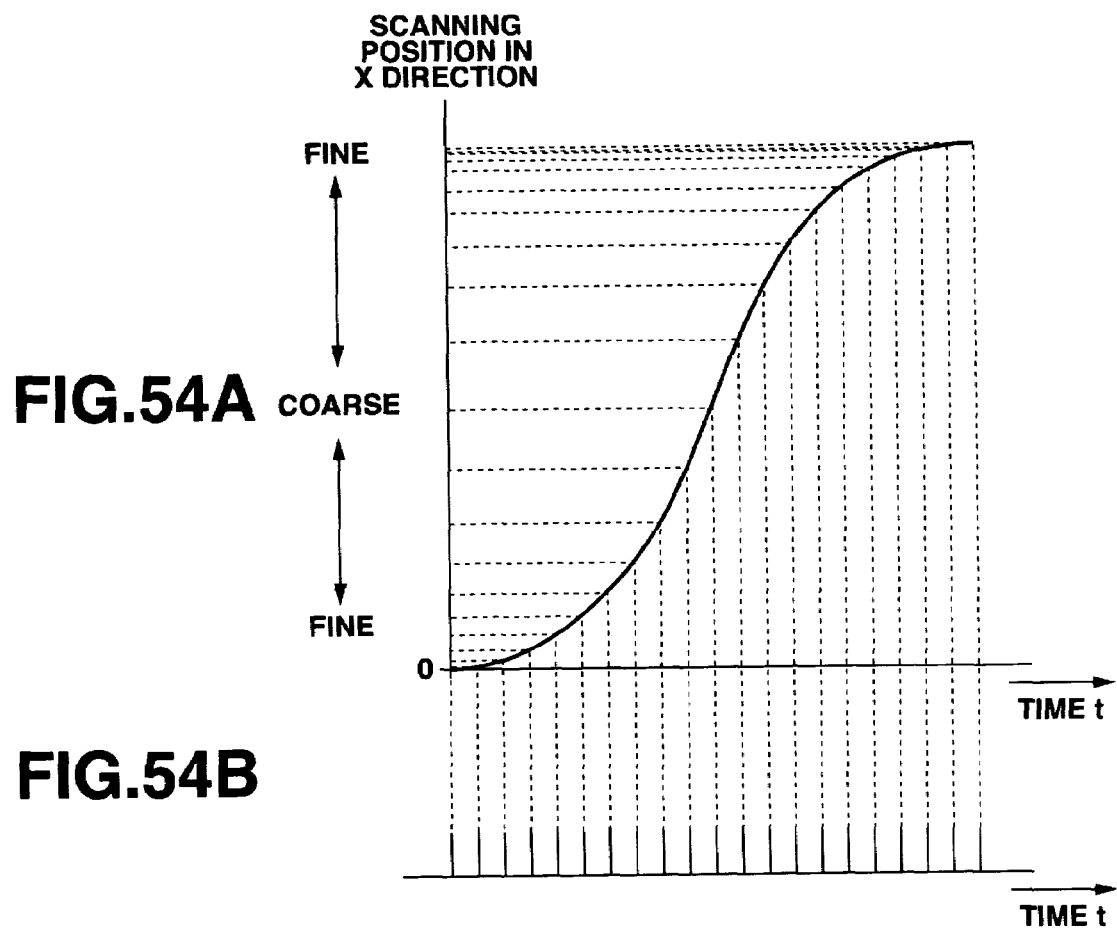
FIG.54A
FIG.54B
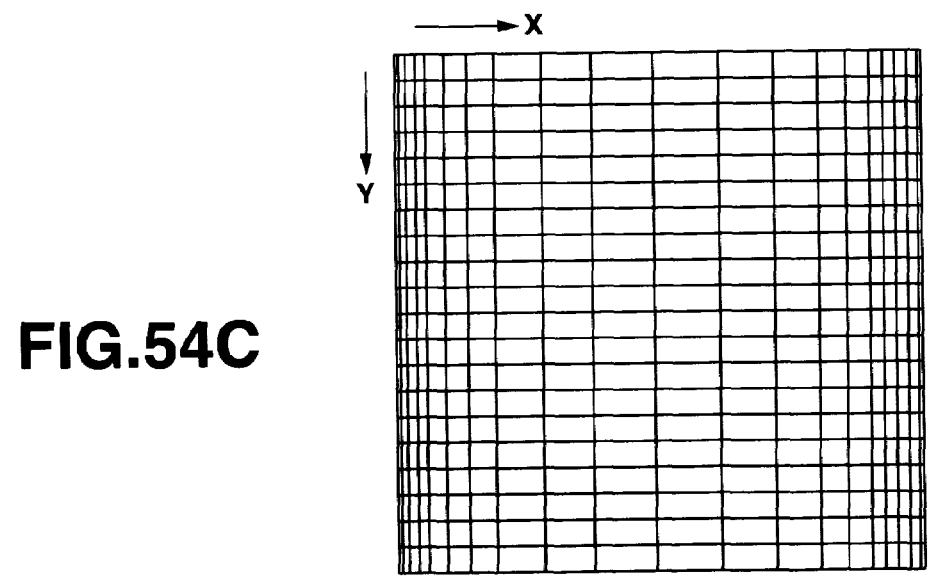
FIG.54C

OPTICAL SCANNING PROBE SYSTEM

TECHNICAL FIELD

This invention relates to an optical scanning probe system with which different types of optical scanning probes are connected according to the site to be examined, optical scanning is performed according to the probe that is connected, and optical image information is obtained.

BACKGROUND ART

Optical scanning probe devices have been developed in recent years with which optical information about an examination site is obtained by transmitting light generated by a light source device through an optical fiber, emitting this light from the tip of the optical fiber and shining it on the examination site, and scanning the focal position back and forth.

A conventional example of this is U.S. Pat. No. 5,120,953.

This conventional example discloses an endoscope that gives an enlarged view of the tissue at the examination site. This conventional example also discloses the technique of scanning the tip of an optical fiber with an actuator, and scanning the focal point with a condensing lens disposed in front of this actuator. The scanning of a focal point with a scanning mirror has also been disclosed in U.S. Pat. No. 5,742,419.

However, when optical fiber scanning is performed by scanning the optical fiber tip end with respect to the lens, the optical fiber, which is disposed along the optical axis of the lens, deviates from this optical axis, making it difficult to achieve high resolution.

Accordingly, the present applicant proposed an optical fiber and (object) lens scanning type of optical scanning probe with which the (object) lens is scanned along with the optical fiber tip in such a case.

With this type, the optical fiber tip disposed along the optical axis of the lens does not deviate in its relative position from the lens when scanned, so in principle the aperture number can be larger and higher resolution is possible.

On the other hand, because optical fiber and lens scanning requires the scanning of both the optical fiber tip and the lens with an optical fiber and lens scanning type of optical scanning probe, an optical fiber scanning type is advantageous in that faster scanning is possible.

Accordingly, when this apparatus is used inside the body, for example, if an optical fiber scanning type can be used if the site being observed is one that moves, such as the heart, and if an optical fiber and lens scanning type, which affords higher resolution, can be used if the site being observed does not move, then the resulting system will be extremely convenient.

The present invention was conceived in light of the above situation, and it is an object thereof to provide an optical scanning probe system with which it is possible to use the optical scanning probe best suited to the site being examined.

Another object is to provide an optical scanning probe with which higher resolution can be obtained.

DISCLOSURE OF THE INVENTION

The optical scanning probe system of the present invention comprises:

a plurality of types of mounting means (119, 122) for mounting optical scanning probes (112A, 112B), at least one of which is detachable, having scanning means (16a, 16c, 16b) for scanning an examination site with the focal point of observation light emitted by a light source device (113);

recognition means (131) for recognizing the type of optical scanning probe mounted to the mounting means (119); and control means (130) for controlling the scanning means (16a, 16c, 16b) in the optical scanning probe according to the optical scanning probe recognized by the recognition means (131), and therefore the optical scanning probe best suited to the site being examined can be mounted and used.

BRIEF DESCRIPTION OF THE DRAWINGS

FIGS. 1 to 11 pertain to a first embodiment of the present invention;

FIG. 1 is a block diagram of the overall optical probe system in the first embodiment;

FIG. 2 is a cross section of the structure of an optical fiber and object lens scanning type of optical probe;

FIG. 3 is a perspective view of the optical unit portion in FIG. 2;

FIG. 4 is a cross section of the structure of an optical fiber scanning type of optical probe;

FIG. 5 is a diagram of the structure of the light source unit;

FIG. 6 is a block diagram of the structure of the imaging device;

FIGS. 7A to 7D are diagrams of how biological tissue is examined;

FIG. 8 is a diagram of the operation of sampling and imaging only in one direction when the scanner is scanned back and forth;

FIG. 10 is a flow chart of the operation of line interpolation;

FIG. 11 is a flow chart of scanning including line interpolation;

FIGS. 12A to 19 pertain to a second embodiment of the present invention;

FIGS. 12A to 12C illustrate, for example, the step of assembling the optical probe in the second embodiment, and FIG. 12D illustrates the structure with a bimorph type;

FIG. 13 is a perspective view of the scanner portion in an optical fiber and object lens scanning type of optical probe;

FIG. 14 is a perspective view of the scanner portion in an optical fiber scanning type of optical probe;

FIG. 15 is a cross section of the structure of an optical fiber scanning type of optical probe;

FIG. 16 illustrates, for example, the spring material in a first variation example;

FIG. 17 illustrates, for example, the spring material in a second variation example;

FIG. 19 is a cross section of the structure on the tip end of an optical fiber scanning type of optical probe;

FIGS. 23 to 25 pertain to a sixth embodiment of the present invention;

FIG. 23 is a block diagram of the structure of an imaging device in the sixth embodiment;

FIG. 25 is a flow chart of the operation of correcting and imaging the hysteresis characteristics using the table in FIG. 24;

FIGS. 26 to 32 pertain to a seventh embodiment of the present invention;

FIG. 26 is a perspective view of the optical unit in the seventh embodiment;

FIG. 27 is a block diagram of the structure of the main components of a control circuit;

FIG. 28 is a block diagram of the structure of an X drive circuit;

FIGS. 29A to 29D illustrate the action of correcting the waveform of a drive signal using the output of a strain sensor;

FIG. 30 is a perspective view of the optical unit in a first variation example;

FIG. 31 is a perspective view of the optical unit in a second variation example;

FIG. 32 is a perspective view of the optical unit in a third variation example;

FIGS. 36 to 38 pertain to a tenth embodiment of the present invention;

FIG. 36 is a perspective view of the structure of the optical unit in the tenth embodiment;

FIG. 37 is a cross section of the structure on the tip end of the optical probe in a variation example;

FIG. 38 is a cross section viewed from a direction perpendicular to that in FIG. 37;

FIG. 39 is an overall structural diagram of the optical scanning microscope in the eleventh embodiment;

FIG. 40 is a cross section of the structure of the tip of the optical probe;

FIG. 41 is a perspective view of the structure of the optical unit provided to the tip;

FIG. 42 is a block diagram of the structure of the controller;

FIG. 43 is a diagram of how the scanning surface is optically scanned;

FIG. 44 is a perspective view of the tip of an endoscope when the optical probe has been inserted;

FIG. 45 is a cross section of the structure of the tip of the optical probe in the twelfth embodiment;

FIG. 46 is a perspective view of the structure of the optical unit provided to the tip;

FIG. 48 is a cross section of the structure of the tip of the optical probe in the fourteenth embodiment;

FIG. 49 is a perspective view of the structure of the optical unit provided to the tip;

FIG. 50 is an overall structural diagram of the optical scanning microscope in the fifteenth embodiment;

FIG. 51 is a cross section of the structure of the tip of the optical probe;

FIG. 52 is a perspective view of the structure of the optical unit provided to the tip;

FIG. 53 is a cross section of a scanning mechanism for scanning the permanent magnet peripheral portion in FIG. 50 in the X and Y directions; and FIGS. 54A to 54C illustrate the scanning operation for imaging in prior art.

BEST MODE FOR CARRYING OUT THE INVENTION

First Embodiment

Figure 1:
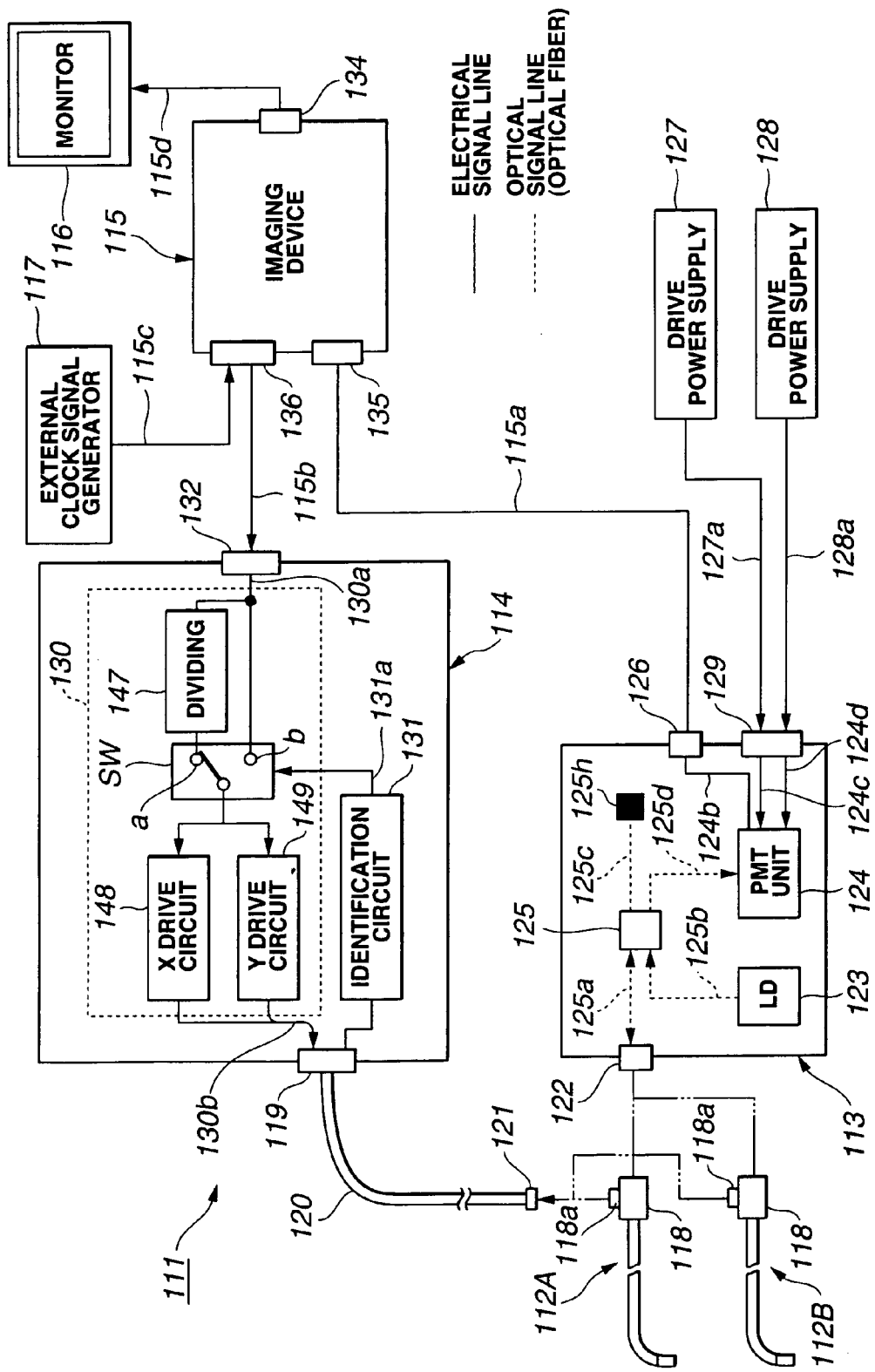

The optical probe system in the first embodiment of the present invention will now be described through reference to FIGS. 1 to 11.

In this embodiment, the object is to provide a system with which optical probes of different scanning types can be selectively used so as to obtain an observation image suited to the examination site.

In specific terms, when an organ near the heart is to be observed, for instance, an observation image that is not greatly affected by the movement of the heart (that is, one with little blurring) can be obtained by using an optical fiber scanning type of optical probe which affords higher scanning speed. When an organ that is distant from the heart and therefore moves very little is to be observed, an image of higher resolution can be obtained by using an optical fiber and lens scanning type of optical probe.

The optical probe system 111 shown in FIG. 1 comprises an optical fiber and object lens integrated scanning type of optical probe (hereinafter referred to as an integrated scanning type of optical probe) 112A, an optical fiber scanning type of optical probe 112B, a light source unit 113 that is detachably connected to either of these optical probes 112A and 112B and thereby supplies light to the optical probe 112I (I=A or B) and detects optical information from the optical probe 112I and outputs it as an electrical signal, a control device 114 that drives the optical unit (the inside scanner) of the optical probe 112I, an imaging device 115 that performs imaging processing in which an image is obtained from the signal coming from the light source unit 113, a monitor 116 that displays the image signal from the imaging device 115, and an external clock signal generator 117 that generates clock signals that serve both as a reference for the drive waveform at which the scanner is driven, and as a reference in image processing.

The optical probe 112I has an electrical connector 118a provided on the side of a connector 118 at the rear end of the optical probe 112I, and this electrical connector 118a is detachably connected to a connector 121 of an electrical cable 120 extending from a connector 119 of the control device 114.

The connector 118, to which is fixed the rear end of an optical fiber 6b (see FIGS. 2 and 4) built into the optical probe 112I, is detachably connected to a connector 122 of the light source unit 113. The control device 114 is electrically connected to the imaging device 115 via a signal line 115b.

The imaging device 115 is electrically connected to the light source unit 113 via a signal line 115a. The imaging device 115 is electrically connected to the monitor 116 via a signal line 115d. The imaging device 115 is also electrically connected to the external clock signal generator 117 via a signal line 115c.

The light source unit 113 has a laser diode (hereinafter referred to as LD) 123 that serves as a light source, a photomultiplier (hereinafter referred to as PMT) unit 124 that detects and multiplies weak optical signals at high sensitivity, and a four-terminal coupler 125. The light source unit 113 is further provided with the connector 122 connected to the connector 118, a connector 126 connected to the signal line 115a, and a connector 129 connected to signal lines 127a and 128a of drive power supplies 127 and 128.

In this light source unit 113, the four-terminal coupler 125 has four terminals 125a, 125b, 125c, and 125d, with the terminal 125a being optically connected to the optical fiber 6b, and the terminal 125b optically connected to the LD 123. The terminal 125c is terminated by an optical fiber terminal 125h, and the terminal 125d is optically connected to the PMT unit 124.

Part of the light coming in through the terminals 125a and 125c is diverted to the terminals 125b and 125d, and conversely, part of the light coming in through the terminals 125b and 125d is diverted to the terminals 125a and 125c.

The PMT unit 124 is electrically connected to the connector 126 via a signal line 124b. The PMT unit 124 is also electrically connected to the drive power supplies 127 and 128 via the drive signal lines 127a and 128a and the connector 129, to which signal lines 124c and 124d are connected.

The control device 114 is equipped with a control circuit 130 having a built-in X drive circuit 148 and Y drive circuit 149 for two-dimensionally driving the scanner, and an identification circuit (recognition circuit) 131 that identifies (at least recognizes) the connected optical probe 112I.

The control circuit 130 is electrically connected to a connector 132 connected to the signal line 115b via a signal line 130a. This control circuit 130 takes in clock signals inputted from the connector 132 via the signal line 130a and either inputs these clock signals directly to the X drive circuit 148 and Y drive circuit 149 via a contact b of a switch SW, or inputs the clock signals via a contact a of the switch SW after the clock signals have undergone frequency division by a frequency dividing circuit 147, producing X drive signals and Y drive signals synchronized to the clock signals or frequency-divided clock signals, which can be outputted from the connector 119 to the optical probe 112I side via a signal line 130b.

The identification circuit 131 identifies the connected optical probe 112I as being the optical probe 112A or 112B based on whether a resistor R is connected to the electrical connector 118a as shown in FIGS. 2 and 4, an identification signal is applied to a selection switch SW via a signal line 131a, and contact a or b is selected.

For example, contact a is switched ON if the probe is identified as 112A, whereas contact b is switched ON if the probe is identified as 112B. When contact b is ON, the frame rate (the number of images obtained per second) is set to 30 Hz, and when contact a is set to be ON, clock signals are frequency-divided by the frequency dividing circuit 147 to ⅙, for example, in which case the frame rate is set to 5 Hz.

In other words, in the case of the probe 112B, an image with little blurring can be obtained even at examination sites where there is movement by scanning two-dimensionally at high speed, and in the case of the probe 112A, an image of high resolution can be obtained by scanning two-dimensionally at low speed.

The imaging device 115 is a device that produces imaging signals, and is equipped with a connector 135 connected to the signal line 115a, a connector 136 connected to the signal lines 115b and 115c, and a connector 134 connected to the signal line 115d.

The imaging device 115 is electrically connected to the control device 114 via the signal line 115b, and clock signals, for instance, can be transmitted to the control device 114. Clock signals that serve as a reference for the drive waveform at which the scanner is driven are inputted via the signal line 115c to the connector 136 of the imaging device 115.

The imaging device 115 is also electrically connected to the PMT unit 124 of the light source unit 113 via the signal line 115a, etc., and produces image signals from the output signals of the PMT unit 124.

The structure of the optical probe 112A will now be described through reference to FIGS. 2 and 3.

As shown in FIG. 2, the optical probe 112A is such that the distal end of a flexible tube 8 is fastened in a circular shape to a rigid optical frame 10 to form a tip component 9, and an optical unit 11G that performs two-dimensional scanning of light and a (transparent and rigid) tip cover unit 12 that serves as a transparent window which is pressed against the examination site at the tip of the optical frame 10 are attached on the inside of this optical frame 10.

The slender optical fiber 6b inserted into the flexible tube 8 is fixed at its rear end through the center hole of the connector 118, while the tip end of the optical fiber 6b is inserted into a hole formed along the center of a rigid base 14 that forms the optical unit 11G, and fixed with an adhesive 27 (such as at the rear end thereof).

This optical fiber 6b emits transmitted light from its tip component (end component) 20, this emitted light is condensed and directed at the examination site through an optical scanning mechanism (scanner), and the reflected light from the examination site (return light) is received by this optical fiber 6b.

Figure 3:
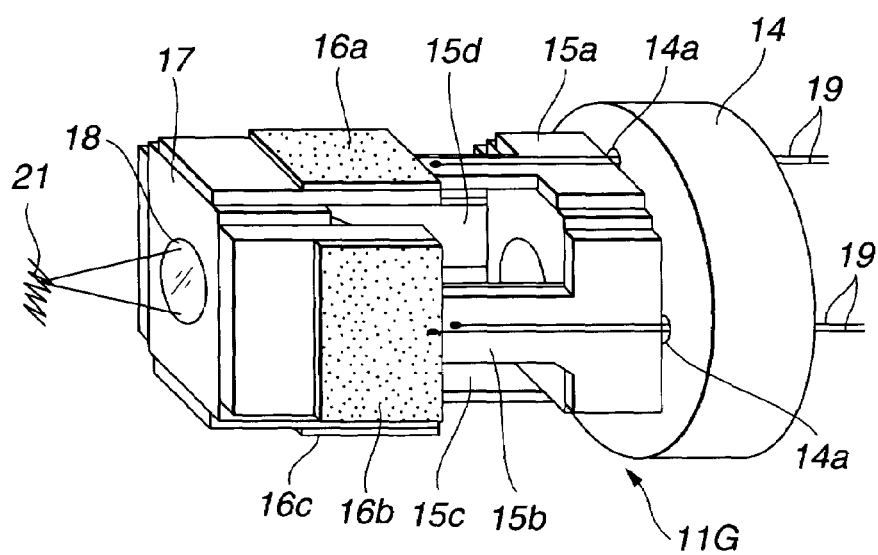

The optical unit 11G portion shown in cross section in FIG. 2 is shown in detail in the perspective view of FIG. 3. This optical unit 11G has the following structure.

The optical probe 112A shown in FIG. 2 has the optical unit 11G at its tip.

The base 14 of the optical unit 11G is fixed to the optical frame 10. The base 14 is designed to be heavier than a lens holder 17 and object lens 18 (discussed below) so that it will stay in place better. The tip end of the optical fiber 6b is inserted in a center hole of the base 14, and part of the optical fiber 6b near the tip is fixed at the rear end of the base 14.

Two sets of parallel thin plates 15a, 15b, 15c, and 15d are fixed at the rear end to the base 14. More specifically, the thin plates 15a and 15c and the thin plates 15b and 15d, which constitute parallel flat springs, are parallel to each other in their plate planes, respectively, the thin plate 15a (or 15c) is disposed such that its plate plane is perpendicular to that of the thin plate 15b (or 15d), the rear end of each plate is fixed to the base 14, and the distal end (as opposed to the rear end) is capable of elastic deformation up and down and to the left and right.

Each thin plate 15*i* (i=a, b, c, or d) has mounted to it, at a location near the front of the thin plate 15*i*, a piezoelectric element 16*i* (16*d* is not shown) in the form of a plate polarized in the thickness direction. Each piezoelectric element 16*i* is a unimorph piezoelectric element. The electrodes on either side of each piezoelectric element 16*i* are each connected to two cables 19 for driving these piezoelectric elements 16*i*. These cables 19 are passed through insertion holes 14*a* formed near the top and bottom and right and left of the base, and are fixed near their rear end with an adhesive 28 and then passed through the inside of the tube 8 until they reach the contact of the electrical connector 118*a*. These cables 19 are then connected to the control circuit 130.

The lens holder 17 is adhesively fixed to the distal ends of the four thin plates 15*i*, and to this lens holder 17 are fixed the object lens 18 (which serves as a condensing optical system) and the tip component of the optical fiber 6*b* (which serves as a light transmission means), that is, the optical fiber tip 20. This lens holder 17 has a frame for attaching the object lens 18, and a frame extension that extends conically from this frame toward the rear, and the optical fiber tip 20 is fixed by being press-fitted into a small hole provided at the apex of this frame extension, which is located on the optical axis O of the object lens 18 (the optical fiber tip component (optical fiber end component) 20 is disposed on the optical axis O of the object lens 18).

When a drive signal is applied to the piezoelectric element 16*i*, the combination of the plate-shaped piezoelectric element 16*i* and the thin plate 15*i* deforms such that the tip end thereof bends perpendicularly to the plate plane with respect to the rear end, the lens holder 17 held at the tip is designed to be able to move in the direction of the bending caused by this deformation, and the object lens 18 and the optical fiber tip 20 held by the lens holder 17 both move, allowing the emitted light to be scanned.

Here, the spreading emitted light is condensed by the object lens 18 using the extremely slender optical fiber tip 20 as the focal point, with the light being emitted so as to be focused at the position of a focal point 21 on the examination site side.

The focal point 21 is scanned in the horizontal direction (X direction) 22 and the vertical direction (Y direction) 23 in FIG. 2 by driving the piezoelectric elements 16*a*, 16*b*, 16*c*, and 16*d*, allowing the scanning plane 24 including the focal point 21 to be scanned. This scanning plane 24 is substantially perpendicular to the axial direction of the optical probe 112A.

The object lens 18 is one with a numerical aperture of at least 0.3, for example.

As can be seen from FIG. 2, the cables 19 driving the piezoelectric elements 16*a*, 16*b*, 16*c*, and 16*d* are inserted into upper/lower and left/right insertion holes 14*a* that are off-center with respect to the optical fiber 6*b* inserted into and fixed in the center hole of the base 14, and a separation component or barrier component 14*b* is formed in which these pairs of insertion holes 14*a* are separated by the base 14. The cables 19 are kept from coming into contact with the optical fiber 6*b* at their tip ends.

Meanwhile, the tip cover unit 12 consists of a cover holder 25 and a cover glass 26 fixed to this cover holder 25. The cover holder 25 is fixed to the distal end of the optical frame 10. The construction here is such that the probe tip component 9 is sealed.

FIG. 4 shows the structure of the fiber scanning type of optical probe 112B. This optical probe 112B employs an optical unit 11H that is different from the optical unit 11G of the optical probe 112A in FIG. 2.

With the optical unit 11G in FIG. 2, the object lens 18 was attached via the lens holder 17 to the tip of the movable thin plate 15*i*, but with this optical unit 11H, the object lens 18 is attached to the optical frame 10 and is immovable, with only the optical fiber 6*b* side being movable.

As shown in FIG. 4, with the optical unit 11H provided to the tip component 9 of this optical probe 112B, the object lens 18 is fixed to the optical frame 10 by a ring-shaped lens holder 17' on the inside near the cover glass 26.

The tip 20 of the optical fiber 6*b*, which is mounted by an adhesive 27 at the rear end of the base 14 along the optical axis O of the object lens 18, and extends forward from the base 14, is press-fitted into and fixed in the center hole of a fiber holder 29. The square outer surface of this fiber holder 29 is fastened to the tip of the thin plate 15*i* just as with the lens holder 17 in FIG. 2.

Also, the resistor R was connected to the electrical connector 118*a* with the optical probe 112A in FIG. 2, but no resistor is connected with this optical probe 112B, resulting in an open state.

The rest of the structure is the same as in FIG. 2, and those structural components that are the same are labeled the same and will not be described again.

Figure 5:
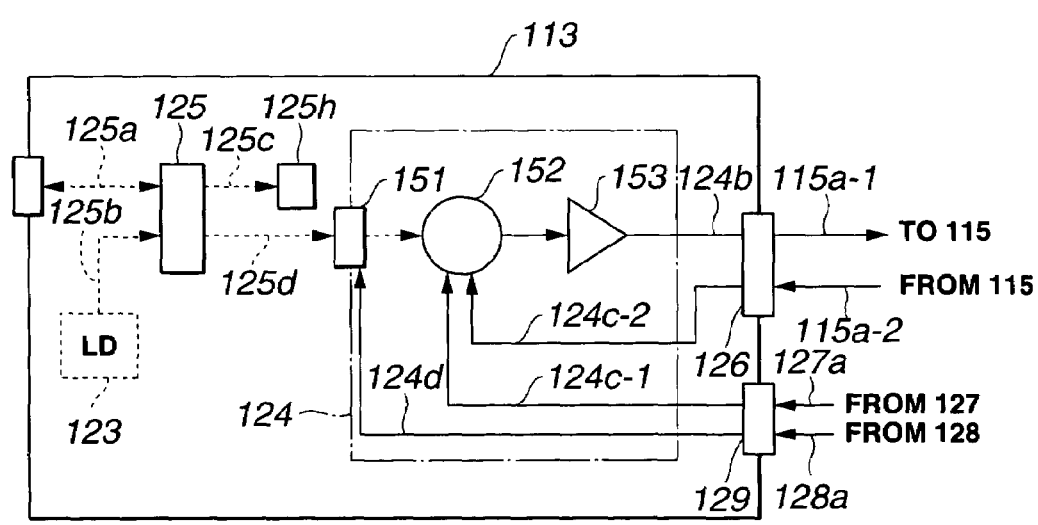

FIG. 5 shows the structure of the light source unit 113.

The light source unit 113 has the LD 123 and the PMT unit 124. The four-terminal coupler 124 comprises a connector 151, a photomultiplier tube (hereinafter referred to as PMT) 152, and a head amplifier 153. The PMT 152 is an element that converts optical signals into electrical signals, and the converted electrical signals are outputted to the head amplifier 153. The head amplifier 153 amplifies the electrical signals from the PMT 152 and outputs them to the connector 126.

With this light source unit 113, as shown in FIG. 1, the laser light generated by the LD 123 is transmitted to the optical probe 112I via the terminal 125*b*, the coupler 125, the terminal 125*a*, and the connector 122, and the examination site is optically scanned by the scanner in the optical probe 112I.

The optical signal reflected from the examination site during scanning by the scanner mechanism in the optical probe 112I is transmitted to the PMT 152 via the optical fiber 6*b*, the connector 122, the terminal 125*a*, the coupler 125, the terminal 125*d*, and the connector 151. The PMT 152 converts this optical signal into an electrical signal, this converted electrical signal is transmitted to the head amplifier 153, and the head amplifier 153 amplifies the inputted signal. This amplified electrical signal is sent to the imaging device 115 via the signal line 124*b*, the connector 126, the signal line 115*a*, and the connector 135.

The signal line 115*a* is a multiple line, of which a signal line 115*a*-1 is used to transmit the above-mentioned electrical signal, while a signal line 115*a*-2 and a signal line 124*c*-2 are used to transmit a control signal controlling the sensitivity of the PMT 152 from the imaging device 115.

The structure of the imaging device 115 will be described through reference to FIG. 6.

The imaging device 115 has an A/D converter 140 that performs A/D conversion, a frame memory 141 that stores one frame of imaging signal, a main memory 142 used for such purposes as temporarily storing an imaging signal, a CPU 143 that controls the imaging, an I/O port 144 used for the input and output of signals, and a hard disk device 150 that contains the operating software for the CPU 143 and so forth. Except for the A/D converter 140, these components are connected to each other via an address bus 145 and a data bus 146.

Clock signals from the external clock signal generator 117 are applied to the various components that require clock signals, such as the I/O port 144, and these clock signals are also supplied to the control device 114 side via the signal line 115b and used in the production of drive signals for the scanner mechanism as discussed above. The drive signals from the X drive circuit 148 and Y drive circuit 149 are applied to the piezoelectric elements 16a, 16b, 16c, and 16d that make up the scanner mechanism, the piezoelectric elements 16b and 16d are vibrated in the X direction and the piezoelectric elements 16a and 16c in the Y direction, and light is scanned in the vibration directions.

The operation of this imaging device 115 will now be described.

The clock signals inputted to the imaging device 115 are sent to the control device 114 side, the X drive signals and Y drive signals produced by the X drive circuit 148 and Y drive circuit 149, respectively, are applied to the scanner of the optical probe 112I, and the light emitted from the scanner is two-dimensionally scanned on the examination site side in the X and Y directions. The returning light is received at the tip face of the optical fiber 6b, goes through the PMT unit 124 of the light source unit 113, and is inputted to the A/D converter 140 of the imaging device 115.

The A/D converter 140 receives the electrical signals inputted through a signal line 140a, subjects them to A/D conversion, and outputs digital signals.

These digital signals are stored as data one line at a time in the frame memory 141.

The data stored in the frame memory 141 is written by the CPU 143 to the main memory 142 via the I/O port 144. Specifically, as shown in FIG. 6, the CPU 143 specifies a data address through the address bus 145 to the frame memory 141 via a control line 143a, the I/O port 144, and a control line 144a.

The specified address data is controlled so as to be stored in the main memory 142 through the I/O port 144 and the data bus 146. Meanwhile, the read-out of the data stored in the main memory 142 is controlled via the control line 143a so that the address data specified by the CPU 143 via the address bus 145 is transferred to the I/O port 144 via the data bus 146.

This data is then converted into an analog signal by a D/A converter (not shown) in the I/O port 144, becoming a video signal which is sent through the control line 144a to the monitor 116 and displayed as an image.

The storage of data in the frame memory 141 is carried out in parallel with the reading of data from the frame memory 141. The CPU 143 performs all control and computational processing within the imaging device 115 other than the above-mentioned transfer of data.

Of the two-dimensional scanning done by the scanner, scanning in the X direction is carried out by resonant drive using a sine wave with a frequency of a few kilohertz. Scanning in the Y direction, meanwhile, is driven at a frequency of from a few hertz to several tens of hertz. More specifically, in the case of the optical probe 112B, the frequency of scanning in the Y direction is set at 30 Hz so as to be compatible with the frame rate of standard television signals, whereas in the case of the optical probe 112A, the frequency of scanning in the Y direction is about 5 Hz, for example.

The operation of the optical probe system 111 structured as above will now be described.

When an organ or other site near the heart is to be observed, the optical probe 112B is connected to the light source unit 113- and the control device 114.

On the other hand, when an organ or other site that is further away from the heart and therefore moves very little is to be observed, the optical probe 112A is connected instead. The connected optical probe 112I is identified by the identification circuit 131, external clock signals of a frequency suited to the identified optical probe 112I are inputted to the X drive circuit 148 and Y drive circuit 149, and X drive signals and Y drive signals are produced in synchronization with these clock signals.

For instance, when the optical probe 112B is used, the X and Y drive signals are set to have a higher frequency than when the optical probe 112A is used, which allows an image to be obtained that is not affected as much by movement. Conversely, when the optical probe 112A is used, it is driven by X and Y drive signals of a lower frequency than when the optical probe 112B is used, in which case imaging is performed at the same clock timing as with the optical probe 112B on the imaging device 115 side, allowing an image of high resolution to be obtained.

The probe tip component 9 is then pressed against the area to be examined. There will be very little blurring of the image here since the examination site is fixed by the tip component 9.

FIGS. 7A to 7D show how the probe can be pressed against a mucous membrane 30 for observation. FIG. 7A depicts an observation with the axial direction of the optical probe 112I perpendicular to the plane of the mucous membrane 30, while FIG. 7B depicts an observation with the tip face of the optical probe 112I pressed into the mucous membrane 30.

In FIG. 7B, pressing the tip face of the optical probe 112I into the mucous membrane 30 stretches the mucous membrane 30 at the portion where the probe is pressed, making the mucous membrane 30 thinner at this portion, putting the focal point 21 (the resulting observation plane Sf (or scanning plane 24)) relatively deep into the mucous membrane 30, and allowing this deeper location to be observed. In other words, the depth of observation can be adjusted by adjusting the force with which the examination site is pressed.

FIGS. 7C and 7D depicts an observation in which the axial direction of the optical probe 112I in the case of FIGS. 7A and 7B is tilted in different directions from the direction perpendicular to the plane of the mucous membrane 30. The angle of the observation plane Sf can be adjusted by adjusting the angle at which the probe is pressed against the site.

Next, the operation of directing laser light at the optical fiber 6b of the optical probe 112I and performing scanning with the scanner of the optical unit 11G or 11H will be described.

The laser light incident at the rear end of the optical fiber 6b is spread out and emitted such that the optical fiber tip 20 is the focal point, after which the light is condensed by the object lens 18 and transmitted through a cover glass 26, after which the focal point 21 is focused on the examination site.

The light reflected from the focal point 21 travels the same optical path as the incident light, and is again incident on the optical fiber 6b at the optical fiber tip 20. In other words, the optical fiber tip 20 and the focal point 21 of the examination site are in a confocal relationship with respect to the object lens 18.

The reflected light that is not at this focal point 21 cannot travel the same optical path as the incident light, and therefore virtually none of it is incident on the fiber of the optical fiber tip 20. Therefore, the optical probe 112I forms a confocal optical system.

The piezoelectric elements 16b and 16d are driven by the X drive circuit 148 in this state. The operation of the piezoelectric elements 16i will be described here.

The thickness of the piezoelectric elements 16i changes when voltage is applied to them. The thickness increases when a positive voltage is applied to the piezoelectric elements 16i, which is accompanied by contraction of the piezoelectric elements 16i in the lengthwise direction. Because the piezoelectric elements 16i are bonded to thin plates 15i whose length does not change at this point, there is an overall deformation involving curvature toward the piezoelectric elements 16i.

Conversely, the thickness decreases when a negative voltage is applied to the piezoelectric elements 16i, which is accompanied by expansion of the piezoelectric elements 16i in the lengthwise direction. Because the piezoelectric elements 16i are bonded to thin plates 15i whose length does not change, there is an overall deformation involving curvature toward the thin plates 15i. If drive signals of different polarity are applied to the two opposing piezoelectric elements 16b and 16d such that one is deformed toward the piezoelectric element and one toward the thin plate, these piezoelectric elements will be deformed in the same direction as the horizontal direction 22.

In the case of the optical probe 112A, when alternating current of opposite polarity is applied to the piezoelectric elements 16b and 16d, the lens holder 17 vibrates, this causes the object lens 18 and the optical fiber tip 20 to move, and the position of the focal point 21 of the laser light is scanned in the X direction 22 of the scanning plane 24 (perpendicular to the paper plane in FIG. 2).

In the case of the optical probe 112B shown in FIG. 4, the object lens 18 is fixed so that only the optical fiber tip 20 side moves, and the position of the focal point 21 of the laser light is scanned in the X direction 22 of the scanning plane 24 (perpendicular to the paper plane in FIG. 4).

In these cases, significant displacement results from driving this system at a resonant frequency. Just as with the X drive, the position of the focal point 21 of the laser light is scanned in the Y direction 23 of the scanning plane 24 by the Y drive circuit 149.

Figure 43:
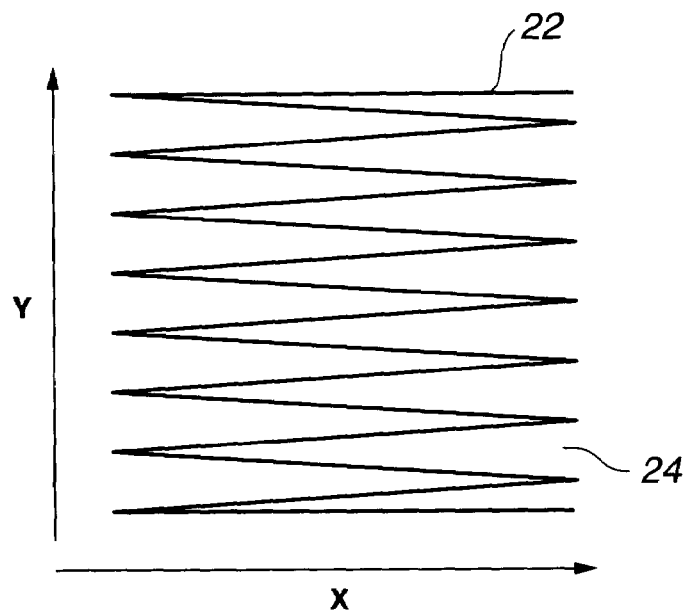

Here, the frequency of vibration in the Y direction is made sufficiently slower than the frequency of scanning in the X direction, the result of which is that the focal point is scanned over the scanning plane 24 as shown in FIG. 43 from top to bottom (Y direction) while vibrating at high speed in the horizontal direction. Along with this, the reflected light at the various points of the scanning plane 24 is transmitted by the optical fiber 6b.

The light incident on the tip 20 of the optical fiber 6b from the examination site side is guided through the coupler 125 of the light source unit 113 to the PMT unit 124, where it is converted into an electrical signal according to the intensity of the light, after which this signal is inputted to the imaging device 115.

The imaging device 115 uses clock signals to determine the drive waveforms of the X drive circuit 148 and Y drive circuit 149, calculates where the focal point is located from the signal output, further calculates the intensity of the reflected light at this point, and repeats this procedure to image the reflected light of the scanning plane 24. This result is temporarily stored as image data in the frame memory 141 inside the imaging device 115, this image data is read out in synchronization with a synchronization signal, and a two-dimensional image of the reflected light intensity of the focal point position when the scanning plane 24 is scanned is displayed on the monitor 116. If needed, the image data is recorded in the hard disk device 150.

With this embodiment, either the optical probe 112A with its higher resolution or the optical probe 112B with its higher scanning speed is used according to the site to be observed. Such specialized usage was impossible in the past.

The scanning plane is scanned as shown in FIG. 8 in this embodiment, and because the piezoelectric elements 16i exhibit hysteresis characteristics in which the displacement varies from the forward path to the backward path even with drive signals of the same value, the degradation of the image due these hysteresis characteristics is eliminated, so sampling need only be performed on either the forward path or the backward path, and not both.

When scanning is performed in the order of the letters in FIG. 8, that is, a→b→c→d→e→f . . . n→o→p →o→n . . . d→c→b→a, the conventional approach was to image data sampled from each scan, but with this embodiment, sampling is performed during scanning for a→b, c→d, e→f, . . . m→n, and o→p, and this data is imaged. Thus sampling only when diagonally scanning in one direction produces an image that is not affected by hysteresis characteristics, and with a simple structure.

With this system 111, the optical fiber and object lens integrated scanning type of optical probe 112A and the optical fiber scanning type of optical probe 112B can both be used, and an observation image suited to the site being observed can be obtained.

The above description was of an example of using two different types of optical probes 112A and 112B according to the type of scanning to be done, but it is also possible to use two optical probes 112A (or 112B) of the same type and vary the diameter of the probes, the size of the scanner, etc., so that the scanners will be driven at different resonant frequencies. In other words, even if the scanning type is the same, probes of the type suited to the application at hand may be readied, the type thereof identified by the identification circuit 131, and the scanners built into the optical probes driven at resonant frequencies for the identified type of probe.

On the imaging device 115 side as well, the identification signal from the identification circuit 131 may be received and imaging suited to that case performed.

Figure 9A:
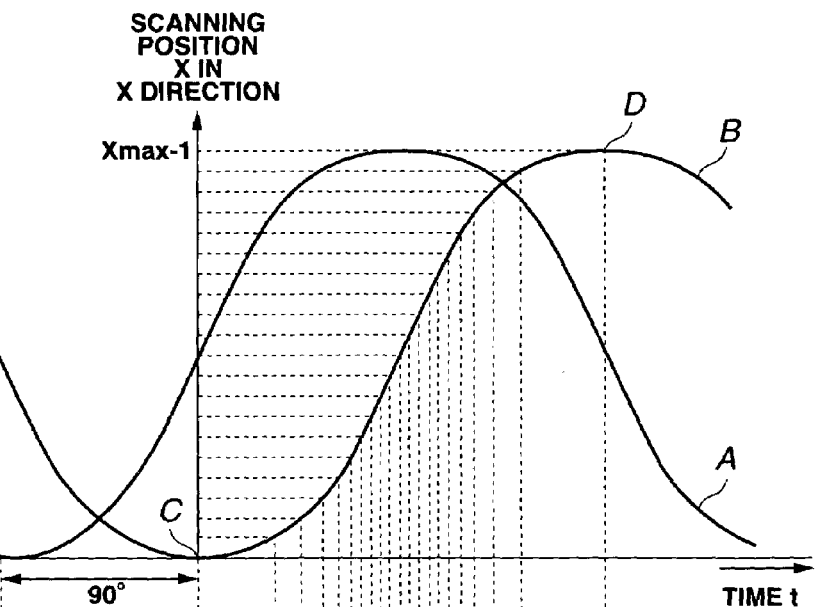
FIGS. 9A to 9C illustrate the operation of sampling with aperiodic pulses.
Figure 9B:

Next, sampling using aperiodic pulses as shown in FIG. 9B will be described.

In the past, as shown in FIG. 54A, because drive in the X direction was by a nonlinear sine wave, if sampling was performed by an A/D converter using periodic pulses (see FIG. 54B) as a reference, then as shown on the X axis (vertical axis) in FIG. 54A, the sampling was coarse near the middle in the X direction, becoming finer toward the ends, and when the image was displayed on a monitor, as shown in FIG. 54C, the middle portion was spread out and the ends squeezed together, resulting in a distorted image.

Figure 9C:
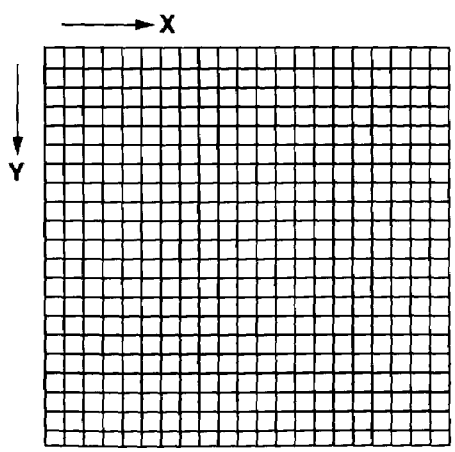

In view of this, with this embodiment, sampling is performed with aperiodic pulses such that the pixels in the X direction are aperiodic (see FIG. 9A) in the imaging with sampling pulses shown in FIG. 9B, resulting in the distortion-free image shown in FIG. 9C.

First, the aperiodic pulse waveform and waveform data in the X direction are produced as the same file using a time axis as a reference, and these are stored in the hard disk device 150 inside the imaging device 115. Because resonant drive is used here, though, the actual scanning position B in the X direction is delayed in phase by 90° with respect to the drive waveform A, as shown in FIG. 9A, so a aperiodic pulse waveform that is delayed by 90° with respect to the drive waveform is produced and stored in advance. Also, the image in the X direction is displayed only at the rise of the sine wave.

The number of pulses p of the aperiodic pulses is found from p=fclk/fx, where fx is the X direction frequency and fclk is the clock signal frequency of the external clock signal generator 117. The aperiodic pulses satisfy the equation t=(p/2π)×arccos(1−2X/(Xmax−1)), where t is an arbitrary time, X is an arbitrary scanning position in the X direction, and Xmax is the number of pixels in the X direction. The interval of the aperiodic pulses is set by the value of each time t when X in this equation is incremented one at a time from 0 to (Xmax−1), and this setting is used to produce the aperiodic pulse waveform.

Thus driving the scanners with a drive waveform A and also sampling with aperiodic pulses yields an image that has no distortion and is free of phase shift due to resonant drive.

Figure 10:
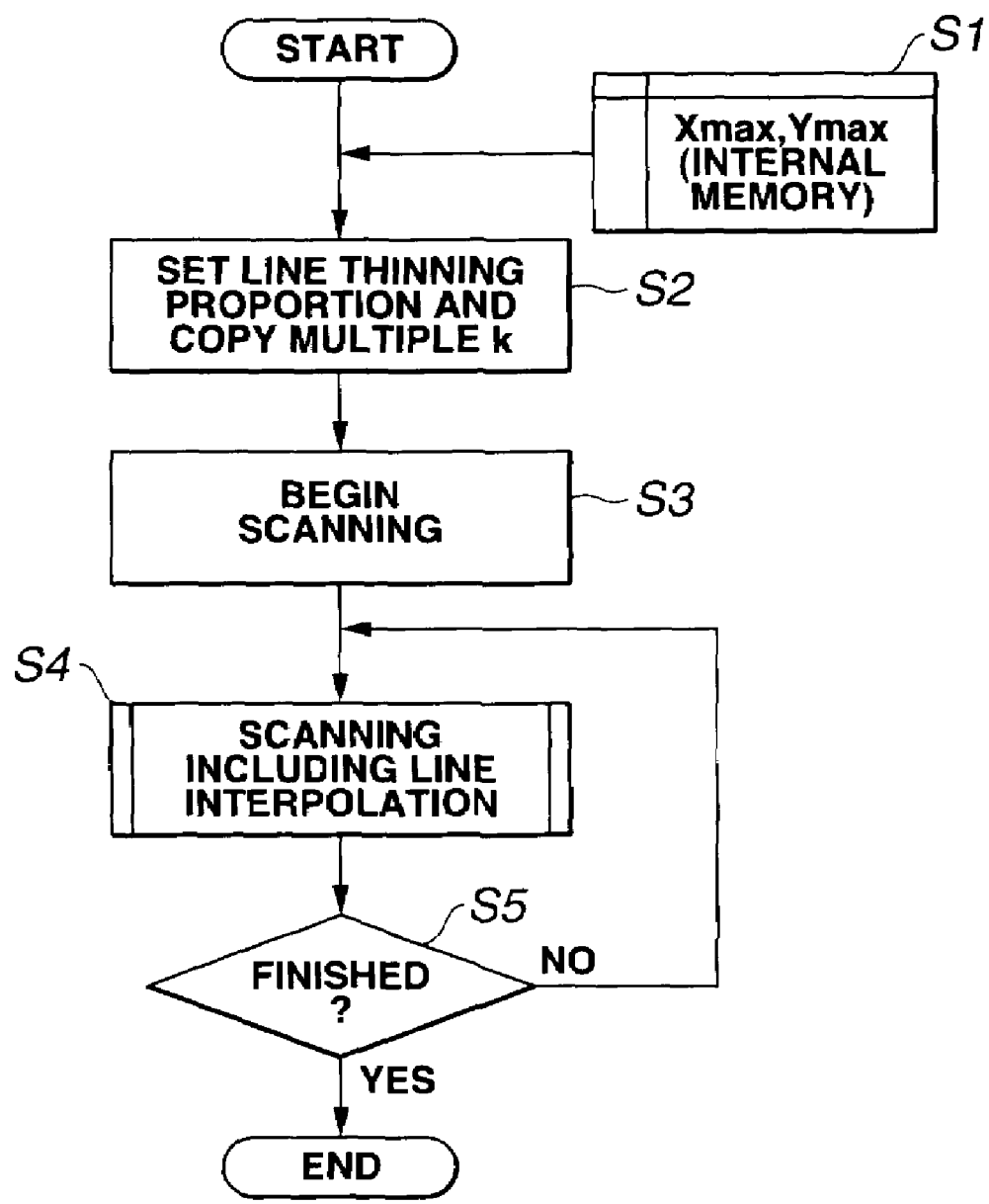

Next, a line interpolation method with which the frame rate can be raised will be described through reference to FIG. 10.

The data A/D-converted by the A/D converter 140 shown in FIG. 6 is successively stored one line at a time in the frame memory 141. Rather than all being read out by the CPU 143, the stored data is instead thinned in a proportion of one out of two lines, for instance. The thinned and read data is written to the main memory 142 via the I/O port 144 and the data bus 146. The written data is read from the main memory 142 by the CPU 143.

Here, lines are read a number of times according to the number of lines thinned as above, and are outputted as an image to the monitor 116 via the I/O port 144.

The flow of the above-mentioned line thinning and display of the same lines a number of times will be described through reference to the flow chart in FIG. 10. First, in step S1 the number of display pixels in the X direction (Xmax) and the number of display pixels in the Y direction (Ymax) are stored ahead of time in the hard disk device 150 inside the imaging device 115. Next, in step S2 the proportion of lines to be thinned, and the factor k indicating the multiplication in copying are set. In step S3 scanning is commenced, in step S4 scanning including line interpolation, that is, the thinning of lines, and copying is executed, and in step S5 scanning is continued unless already complete.

Figure 11:
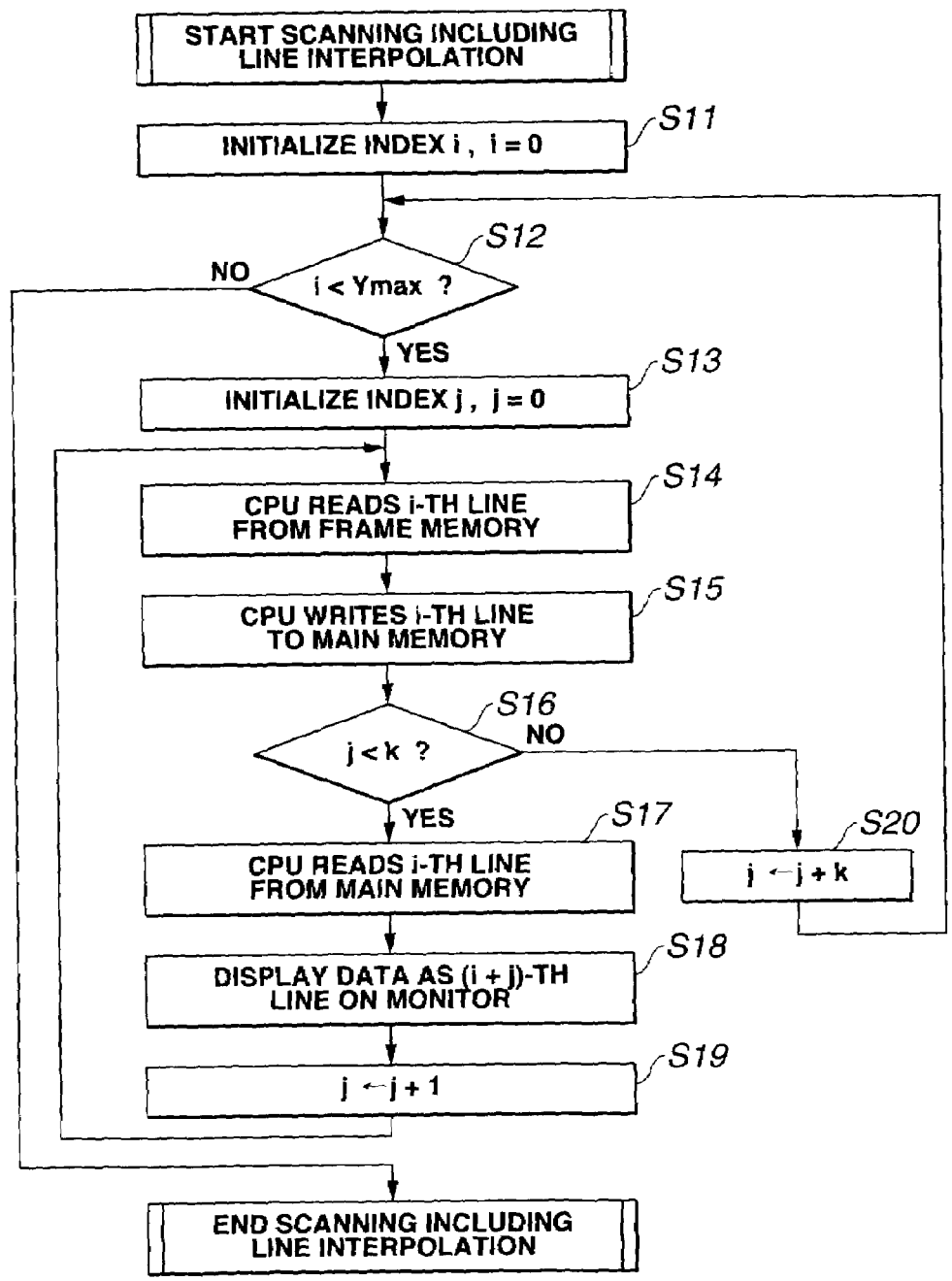

The flow of the scanning including line interpolation in this step S4 will be described through reference to FIG. 11. First, in step S11 an index i, which expresses the number of lines of the image to be displayed, is initialized at i=0. Then, in step S12 a decision is made as to whether i is less than Ymax (i<Ymax). If the answer is yes, then in step S13 an index j, which expresses the number of lines to be copied, is initialized at j=0. Next, the CPU 143 causes the data for the i-th line to be read from the frame memory 141 in step S14, and to be written to the main memory 142 in step S15.

Next, in step S16 a decision is made as to whether the index j is less than the index k (j<k). If the answer is yes, then in step S17 the data for the i-th line written to the main memory 42 is read out, in step S18 this is displayed on the monitor 116 via the I/O port 144 as data for the i+j-th line, in step S19 the index j is incremented, the flow returns to step S14, in step S16 a decision is made as to whether j<k, and this process is repeated until all of the lines to be copied have been displayed.

If j<k is false in step S16, that is, if the data for the i-th line has been copied and displayed by the amount set for k, then in step S20 (i+k) is put in for i by i→i+k, the flow returns to the decision as to whether i<Ymax, and the process of displaying the data for the i+k-th line, and the copied data thereof, is repeated.

If the answer as to whether i<Ymax in step S12 is no, that is, if the display of one frame of data has been finished, this sub-routine is ended, a decision is made as to whether to end scanning, and unless it is ended, the next frame image is repeatedly overwritten according to the above flow. Thus, rather than displaying all of the data stored in the frame memory 141, the portion remaining after thinning is copied and displayed according to how much it was thinned.

Therefore, when sampling is performed with aperiodic pulses, the resulting image has no distortion and is free of phase shift due to resonant drive. The optical probes 170A, 170B, 176B, 201A, 221A, 231A, 401A, 431, and 451 discussed below can also be driven in this embodiment.

Second Embodiment

A second embodiment of the present invention will now be described through reference to FIGS. 12A to 19. It is an object of this embodiment to provide an optical probe that is simple to assemble and therefore lower in cost, and with which the effect of interference due to resonance can be reduced.

FIG. 12A is an exploded view (prior to assembly) of a drive unit 161 and a support member 162 that is attached to the rear of this drive unit 161. This drive unit 161 is provided with a slit 163d, wherein a rectangular bottom plate 163a and side plate 163b are formed from a single piece of spring material such as stainless steel (SUS), linked by a small linking component 163c at the rear end.

Unimorph piezoelectric elements 164a and 164b in the form of rectangular thin plates are affixed to the bottom plate 163a and side plate 163b, respectively. One of the plates, such as the bottom plate 163a, is formed such that its distal end is longer than that of the side plate 163b, and the outer surface of the tip component can be fixed with an adhesive or the like to a tip frame 165 as shown in FIG. 12C.

The spring material shown in FIG. 12A is bent at a right angle at the linking component 163c, and the two faces on the inside at the rear end which form a right angle are fixed with an adhesive or the like to the support member 162, which is provided with a hole through which an optical fiber 167 passes.

Figure 13:
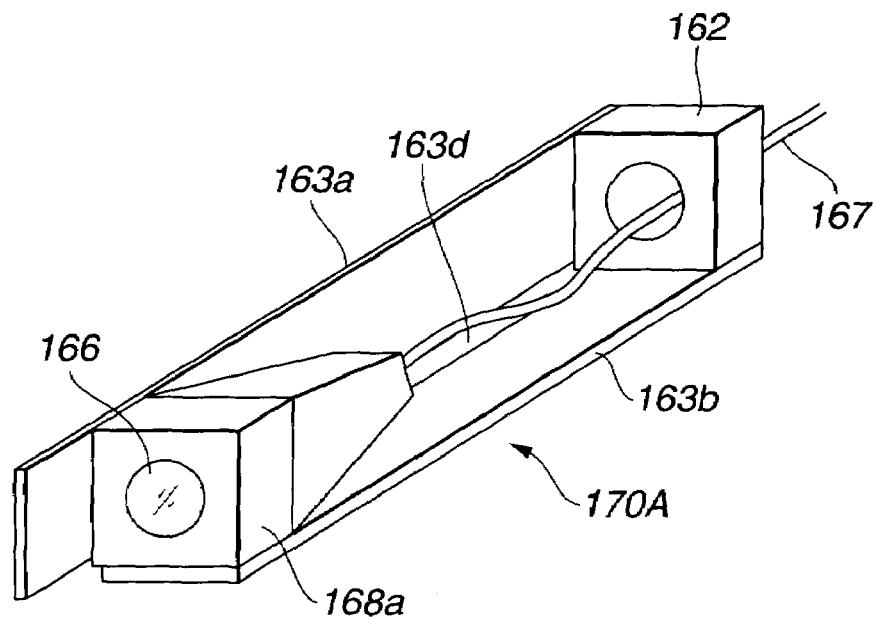

After this, a lens holder 168a to which are fixed the tip of the optical fiber 167 and an object lens 166 shown in FIG. 12C is fixed with an adhesive or the like to the two faces at the distal end of the spring material bent as shown in FIG. 12B, signal lines 169 or the like (see FIG. 12C) for applying a drive signal to the piezoelectric elements 164a and 164b are connected, and a scanner 170A that performs two-dimensional scanning is formed as shown in FIG. 13. The signal lines 169 are not shown in FIG. 13.

The scanner 170A is such that the tip outer surface of the bottom plate 163a is fixed to the rigid tip frame 165 attached to the distal end opening of a tube 171, and an optical fiber and object lens integrated scanning type of optical probe 173A is formed as shown in FIG. 12C. The opening of the tip frame 165 is blocked off by a cover glass 172.

A drive signal for driving in the X direction is applied to the piezoelectric element 164b through a signal line 169, and a drive signal for driving in the Y direction is applied to the other piezoelectric element 164a, the result being that the tip of the optical fiber 167 and the object lens 166 are integrally vibrated in the X and Y directions and the light is scanned two-dimensionally.

This optical probe 173A can be easily manufactured by affixing the two piezoelectric elements 164a and 164b to a single piece of spring material and then bending, for example. Also, since scanning can be performed with this optical probe 173A such that the piezoelectric elements 164a and 164b are vibrated one in the X direction and the other in the Y direction, the structure and assembly are both simpler than when scanning is performed with a pair of piezoelectric elements, so the cost is lower and the apparatus is lighter.

Also, compared to a scanner in which a pair of piezoelectric elements are two-dimensionally vibrated, scanning by the vibration of one element has less effect on scanning by the vibration of the other element.

The support member 162 has the function of preventing twisting or the like from occurring at the distal and rear ends of the spring material. In other words, if this support member 162 is not used, there is the possibility that twisting will occur at the distal and rear ends of the spring material, but the occurrence of this twisting can be effectively prevented by using the support member 162.

In the above description, a unimorph piezoelectric actuator in the drive unit 161 was constituted by affixing the plate-form piezoelectric elements 164a and 164b to one side of the spring material such that they were adjacent in the direction perpendicular to the lengthwise direction, but as with the drive unit 161' shown in FIG. 12D, plate-form piezoelectric elements 164a' and 164b' may also be affixed to the other side of the spring material to configure a bimorph piezoelectric actuator. The piezoelectric elements 164a' and 164b' have the same shape as the piezoelectric elements 164a and 164b, respectively. FIG. 12D depicts the unit shown in FIG. 12A, viewed from the right side, for example.

A drive unit may also be employed that combines the drive units 161 and 161'. For instance, the low-speed drive side may be a unimorph piezoelectric actuator, and the high-speed drive side a bimorph piezoelectric actuator.

The assembly of the optical fiber and object lens integrated type of optical probe 173A shown in FIG. 12C featuring the drive unit 161 and support member 162 shown in FIG. 12A was described, but an optical fiber scanning type of optical probe 173B can also be assembled as described below using the drive unit 161 and support member 162.

Figure 14:
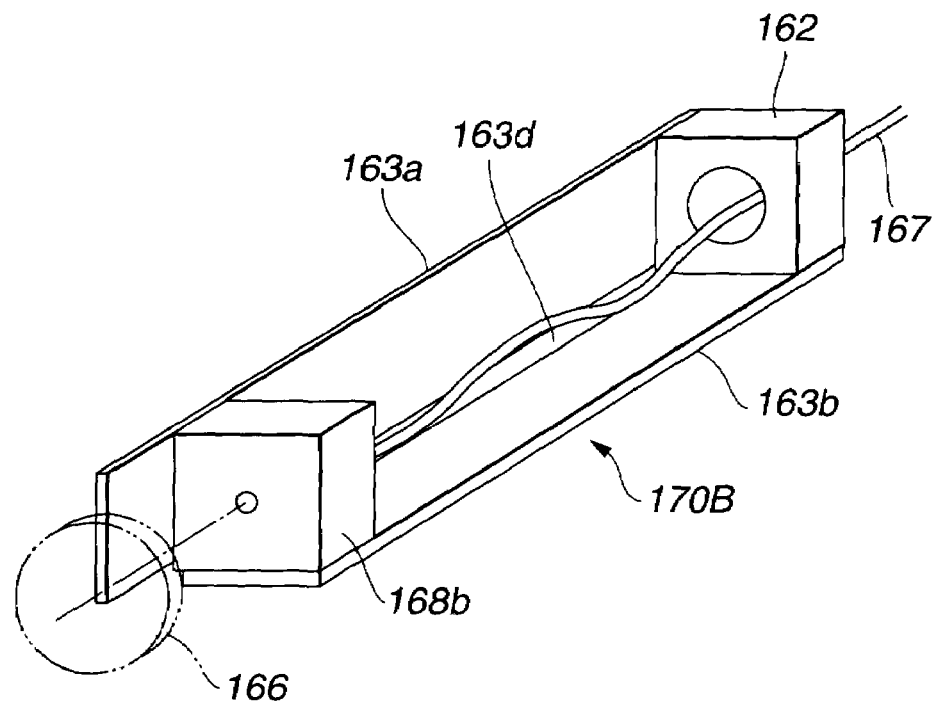

FIG. 14 shows a scanner 170B in the case of an optical fiber scanning type. With the scanner 170A in FIG. 13, the lens holder 168a to which were fixed the object lens 166 and the tip of the optical fiber 167 was attached to the bottom plate 163a and side plate 163b bent at a right angle, but with the scanner 170B shown in FIG. 14, a fiber holder 168b to which is fixed the tip of the optical fiber 167 is attached to the distal end of the bottom plate 163a and side plate 163b.

Figure 15:
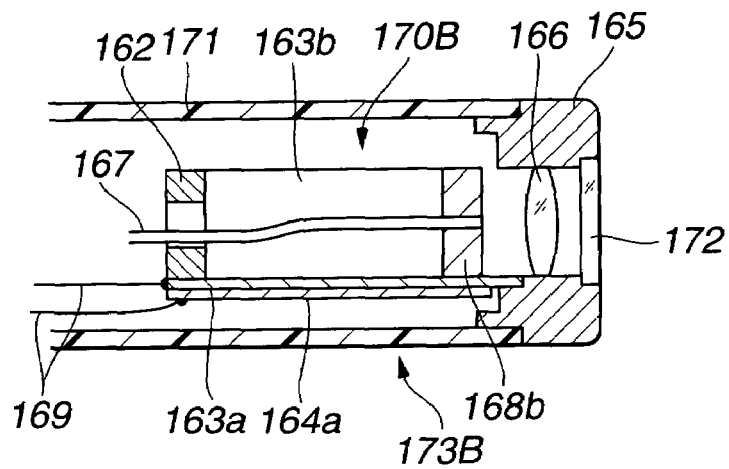

As shown in FIG. 15, the object lens 166 is fixed by the tip frame 165 to which the cover glass 172 is fixed ahead of the tip face of the optical fiber 167, thereby forming the optical probe 173B shown in FIG. 15.

In this case, when a drive signal is applied to the two piezoelectric elements 164a and 164b, the tip of the optical fiber 167 is two-dimensionally vibrated along with the fiber holder 168b. This scanner 170B has the same effect as the scanner 170A discussed above.

Figure 16:
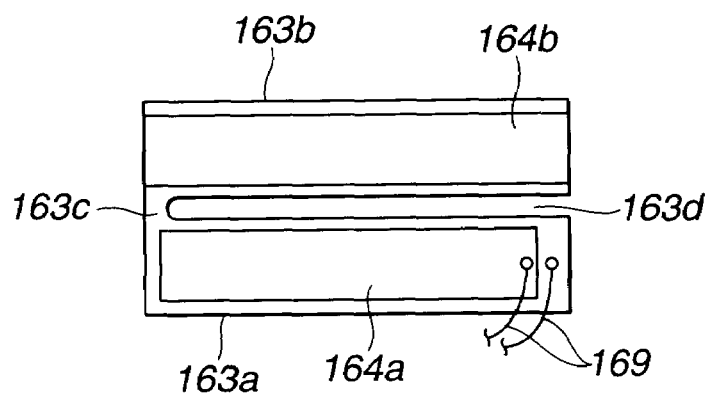

FIG. 16 illustrates the spring material, etc., in a first variation example of FIG. 12A. In FIG. 12A, the bottom plate 163a is longer than the side plate 163b, but in FIG. 16, the bottom plate 163a and side plate 163b are the same length, and the lengths of the affixed piezoelectric elements 164a and 164b are different.

In the case of FIG. 16, the piezoelectric element 164a is made shorter than the piezoelectric element 164b, and the signal lines 169 are connected to the distal end. With this variation example, when either the piezoelectric element 164a or 164b is resonantly vibrated, because the other piezoelectric element has a resonance point at a different frequency from the resonance frequency of the vibrating side, there is no interference caused by this vibration.

Figure 17:
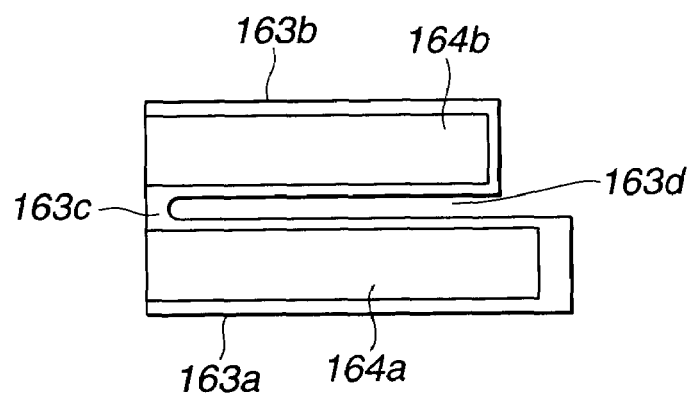

In FIG. 16, the piezoelectric elements 164a and 164b of different lengths were affixed to the bottom plate 163a and side plate 163b of the same length, but as in the second variation example shown in FIG. 17, the same effect as in the case of FIG. 16 will be obtained if the piezoelectric elements 164a and 164b of the different lengths are affixed to the bottom plate 163a and side plate 163b of different lengths.

Figure 18A:
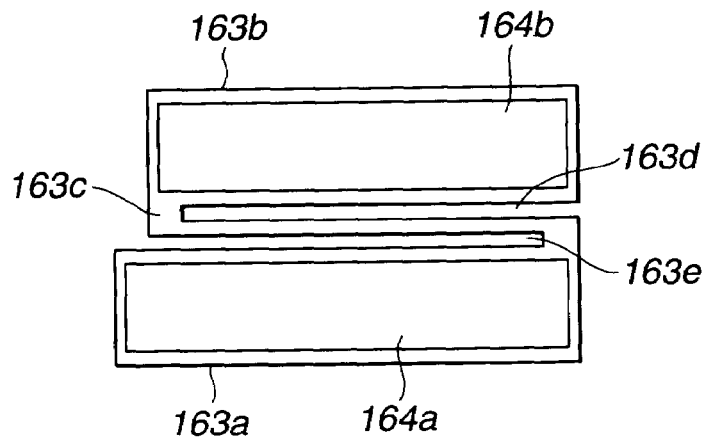
FIGS. 18A and 18B illustrate, for example, the spring material in a third variation example.

FIG. 18A illustrates the spring material, etc., in a third variation example. In FIG. 12A, the slit 163d was formed by cutting out the material from the distal end, but in FIG. 18A, material is further cut out from the rear end, forming a slit 163e that is adjacent to the slit 163d.

Figure 18B:
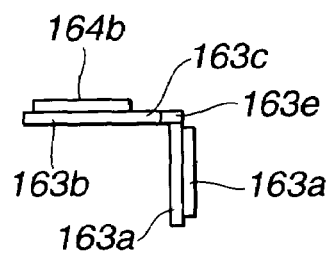
Figure 19:
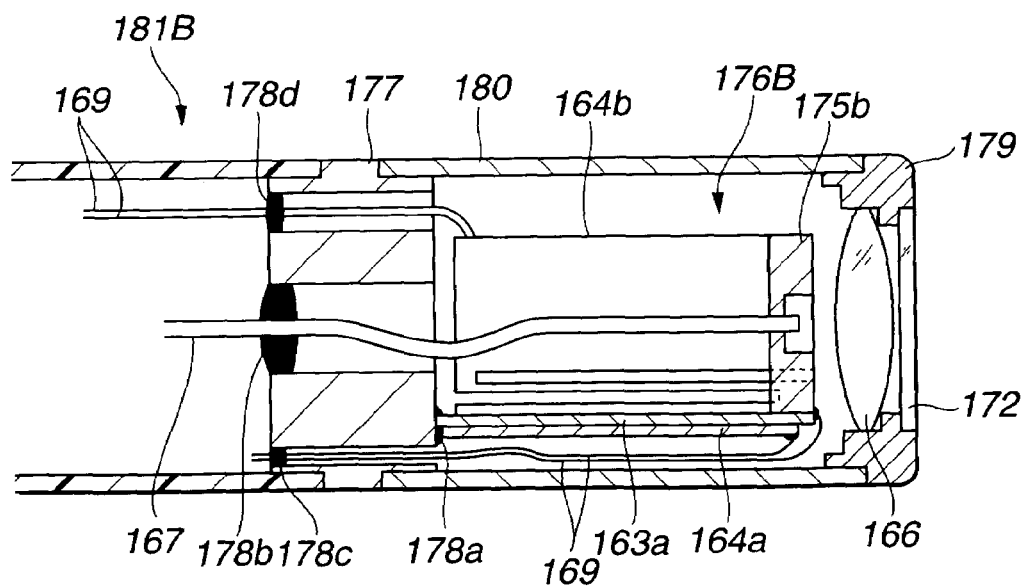

The spring material in FIG. 18A is bent at a right angle as in FIG. 18B. FIG. 18B is a view of when the spring material in FIG. 18A is bent at a right angle, viewed from the rear end side thereof, that is, from the left. A scanner 176B is formed by attaching a fiber holder 175b, to which is fixed the tip of the optical fiber 167 as shown in FIG. 19, for example, to the distal end of the bent spring material in FIG. 18B. The rear end of one of the bent spring material sides (such as the bottom plate 163a) is fixed by an adhesive 178a at the front end of a base member 177.

The object lens 166 is attached to a tip cover 179 right in front of the tip face of the optical fiber 167. This tip cover 179 has attached to it the cover glass 172 at the opening in front of the object lens 166. The front end of a rigid tip tube 180 is fixed to this tip cover 179, and the rear end of this tip tube 180 is fixed to the base member 177. The distal end of the flexible tube 171 is affixed to this base member 177.

The optical fiber 167, whose tip is fixed by the fiber holder 175b, is inserted into a through hole in the base member 177 and extends toward the rear end, and is affixed with an adhesive 178b in the through hole portion in a state in which there is some play in the fiber.

The signal lines 169 connected to the piezoelectric elements 164a and 164b are also inserted into the through hole of the base member 177 and extend toward the rear end, and are affixed by adhesives 178c and 178d in the through hole portion in a state in which there is some play in the lines, so that an optical fiber scanning type optical probe 181B is formed.

FIG. 19 depicts an optical fiber scanning type of optical probe 181B, but an optical fiber and object lens integrated scanning type of optical probe can also be formed by using a lens holder that fixes the object lens 166 and the tip of the optical fiber 167 instead of the fiber holder 175b.

This variation example also yields substantially the same effect as that described for FIG. 12.

Third Embodiment

A third embodiment of the present invention will now be described through reference to FIG. 20. It is an object of this embodiment is to provide an optical probe with which a vertical tomogram can be obtained with a simple structure.

A scanner generally must be driven in the depth direction to obtain a tomogram in the depth direction with an optical probe, but with a scanner that two-dimensionally scans an object lens and an optical fiber, any further drive in the depth direction results in an extremely complicated scanner structure, and the assembly of this scanner is difficult, so in this embodiment a tomogram having a component of the depth direction is obtained with a simple structure as described below.

Figure 20:
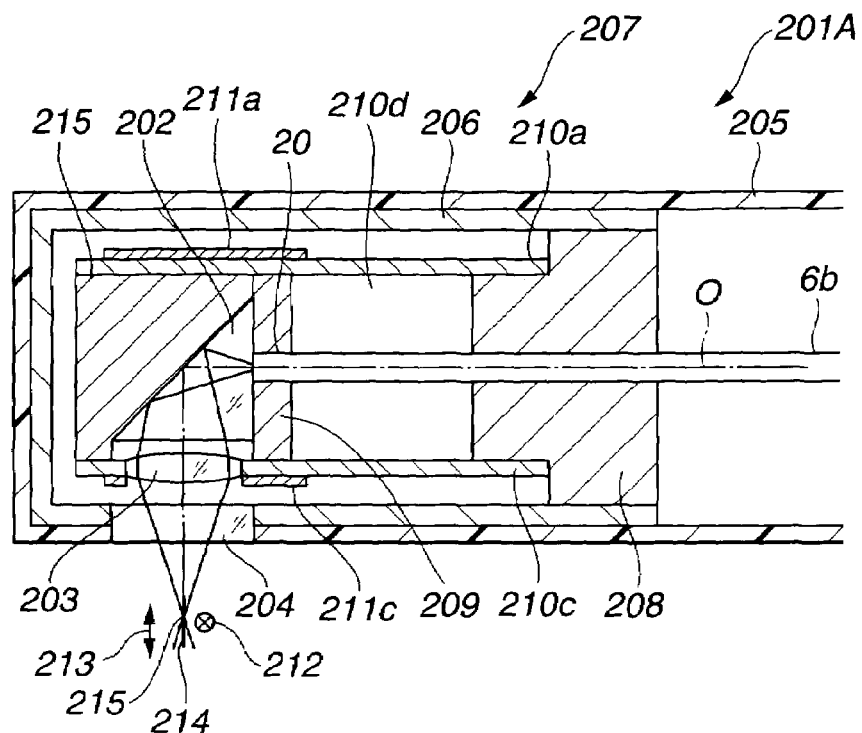
FIG. 20 is a cross section of the structure on the tip end of an optical probe in a third embodiment of the present invention.

The optical probe 201A shown in FIG. 20 is like the optical probe 112A in FIG. 2, but a prism 202 for changing the optical path to the side at a right angle is disposed ahead of the emission end 20 of the optical fiber 6b, and the light emitted in the lengthwise direction by this prism 202 is reflected at a right angle and guided to the side, then condensed by an object lens 203 disposed facing this side direction, and emitted to the side through a transparent cover glass 204.

Accordingly, in this embodiment, a flexible tube 205 that serves as a sheath tube for the optical probe 201A is blocked off at its distal end and opens to the side, and a rigid optical frame 206 to which the cover glass 204 is attached is disposed in the portion of the inside of the distal end of this tube 205 that opens to the side, forming a tip component 207.

A base member 208 is affixed on the inside at the rear end of the optical frame 206, and the tip of the optical fiber 6b passing through the center hole of this base member 208 is affixed by press-fitting or the like into the center hole in a fiber holder 209, with the four sides (top, bottom, left, and right) of this fiber holder 209 being supported by thin plates 210a, 210b, 210c, and 210d (210d is not shown).

The rear ends of the thin plates 210a, 210b, 210c, and 210d are supported by the base member 208, and piezoelectric elements 211a, 211b, 211c, and 211d (211b and 211d are not shown) are respectively affixed to the outer surfaces thereof on the distal end side.

The prism 202 is fixed with an adhesive or the like to the front face of the fiber holder 209, and the light emitted from the tip 20 of the optical fiber 6b is entirely reflected at a right angle off an inclined face, and is incident on the opposing object lens 203.

This object lens 203 is attached with an adhesive or the like at an opening provided on the distal end side of the thin plate 210c, and light is emitted to the side through the cover glass 204 attached to an opening in the tube 205 and an opening in the optical frame 206 facing the object lens 203, and focused at a focal point 215.

A drive signal from the X drive circuit is applied to the paired piezoelectric elements 211b and 211d, a drive signal from the Y drive circuit is applied to the paired piezoelectric elements 211a and 211c, and these piezoelectric elements are driven in the X direction 212 (perpendicular to the paper plane in FIG. 20) or the Y direction 213 (vertically in FIG. 20) as the case may be. The scanning plane 214 in this case is a plane indicated by a bold line in FIG. 20, which is perpendicular to the paper plane and includes the vertical direction, and the Y direction 213 coincides with the depth direction of the examination site, so an image having the scanning plane 214 in the depth direction is obtained.

The inclined face of the prism 202 may be fixed via a fixing member 215 as shown in the figure, or it may be fixed to the fiber holder 209 without the use of the fixing member 215.

With the optical probe 201A shown in FIG. 20, the optical fiber 6b and the object lens 203 are integrally scanned, but if the object lens 203 is attached on the optical frame 206 side, an optical fiber scanning type of optical probe can be formed.

With this embodiment, scanning is possible in the depth direction and in the horizontal direction (lateral direction) with a simple structure featuring two-dimensional scanning, so a perpendicular tomogram can be obtained.

Fourth Embodiment

A fourth embodiment of the present invention will now be described through reference to FIG. 21. It is an object of this embodiment to provide an optical probe with which a tomogram having a component of the depth direction can be obtained with a simple structure.

Figure 21:
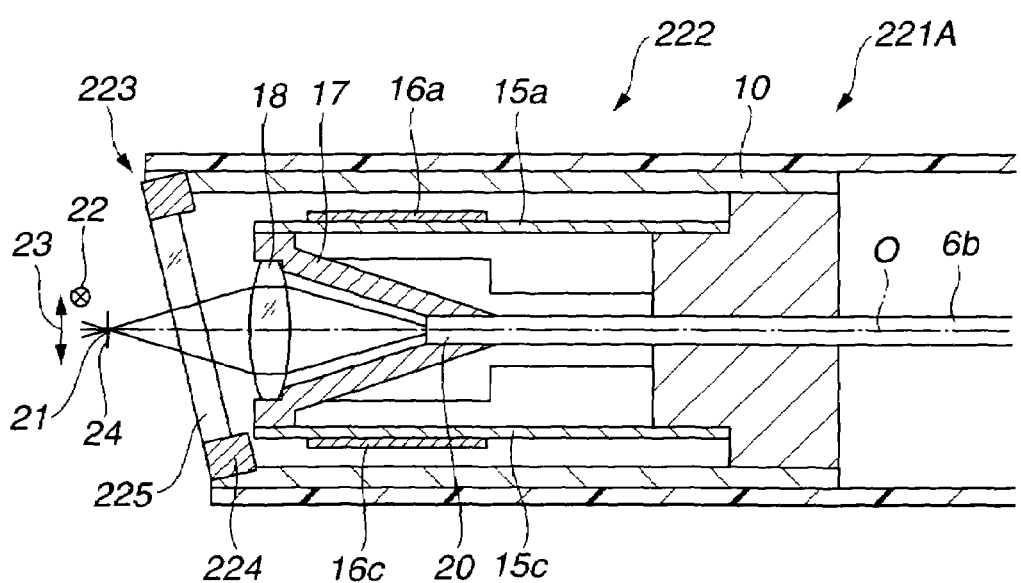
FIG. 21 is a cross section of the structure on the tip end of an optical probe in a fourth embodiment of the present invention.

With the optical probe 112A shown in FIG. 2, the tip cover unit 12 of the tip component 9 was perpendicular to the optical axis O, but with the optical probe 221A shown in FIG. 21, a tip-cover unit 223 provided to a tip component 222 is at a specific angle other than 90 degrees to the optical axis O.

The tip cover unit 223 comprises a cover holder 224 and a cover glass 225. The cover glass 225 is affixed to the cover holder 224, and the cover holder 224 is covered with the tube 8 and adhesively fixed along with the distal end of the tube 8 to the distal end of a rigid optical frame 10 whose distal end has been cut at an angle.

The rest of the structure is the same as that described for FIG. 2, and will therefore not be described.

In this embodiment, when the outer surface of the cover glass 225, which serves as the angled observation face of the tip cover unit 223, is pressed against tissue for observation, a diagonal tomogram is obtained in which the image of the scanning plane 24 deepens as scanning proceeds in the Y direction 23.

The angle of inclination of the tip cover unit 223 in FIG. 21 is merely one example, and a variety of angles may be employed in order to obtain the desired diagonal tomogram.

With this embodiment, the observation plane is provided at an angle, rather than perpendicular, to the optical axis O, so an image having a component of the depth direction is obtained according to the inclination, which allows a diagonal tomogram to be obtained.

The structure can also be such that the tip cover unit 12 shown in FIG. 2 and the tip cover unit 223 shown in FIG. 21 can each be selected for detachable mounting to the optical frame 10, allowing the user to obtain the desired image.

Fifth Embodiment

A fifth embodiment of the present invention will now be described through reference to FIG. 22. It is an object of this embodiment to provide an optical probe with a wide range of applicability to various observation planes.

With a straight-on viewing type of optical probe, when the probe is inserted into an endoscope channel and the probe tip pressed against the examination site for observation, the probe works effectively when the examination site has a plane that is perpendicular to the tip face of the probe, but it is difficult to press the probe against tubular tissue such as that in the esophagus. On the other hand, a side viewing type is effective when observing tubular tissue, but is difficult to press against tissue that is perpendicular to the probe tip. Accordingly, in this embodiment the structure allows observation in either case, as discussed below.

Figure 22:
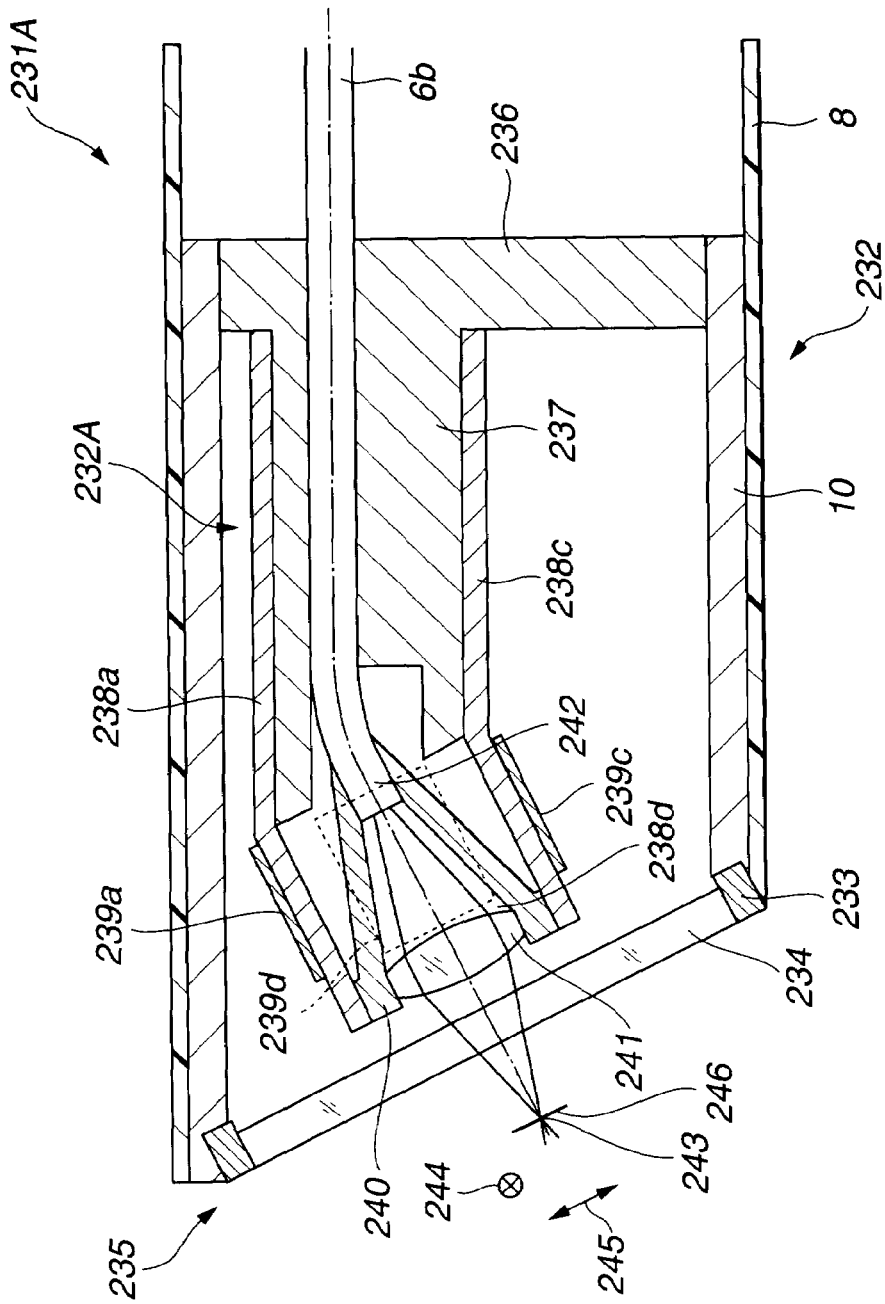
FIG. 22 is a cross section of the structure on the tip end of an optical probe in a fifth embodiment of the present invention.

The tip component 232 of the optical probe 231A shown in FIG. 22 has an optical unit 232A structured such that the distal end side of the optical unit 11G in the optical probe 112A in FIG. 2 is bent at a specific angle (such as about 45 degrees).

Accordingly, a tip cover unit 235 is structured such that the tube 8 and the distal end face of the optical frame 10 housed inside the distal end of this tube 8 are cut at an angle (such as about 45 degrees), a cover glass 234 is attached to the optical frame 10 by a cover holder 233 at this open portion cut at an angle, and the face of the cover glass 234 is tilted forward.

A base 236, to which is fixed the rear end of the optical frame 10, has formed on it an extension 237 extending forward and becoming more slender in stepwise fashion, and the tip end of the optical fiber 6b is inserted into a through hole provided in the lengthwise direction of this extension 237.

Thin plates 238a and 238c are affixed to this extension 237 above and below, with the distal ends bent midway (such as at about 45 degrees), piezoelectric elements 239a and 239c are applied to the outer surface on the distal end sides of these thin plates 238a and 238c, and the outer surfaces at the top and bottom of a lens holder 240 are affixed to the thin plates 238a and 238c on the inside at the distal ends.

An object lens 241 is affixed on the inside at the distal end of this lens holder 240, and the optical axis O is disposed so that it coincides with the center axis of the object lens 241 and is perpendicular to the face of the cover glass 234 and the face of the object lens 241. A bent tip component 242 in the optical fiber 6b is affixed in a hole at the conically tapered rear end of the lens holder 240.

Thin plates 238d and 238b (238b is not shown) are attached to the left and right sides of the extension 237, piezoelectric elements 239d and 239b (239b is not shown) are applied to the outer surface at the distal ends of these thin plates, and the left and right sides of the lens holder 240 are affixed to the inner surface at the distal ends of these two thin plates.

The piezoelectric elements 239a and 239c, and the piezoelectric elements 239d and 239b (239b is not shown) perpendicular to these, are then driven so that the focal point 243 is scanned in the horizontal direction (X direction) 244 and vertical direction (Y direction) 245 in FIG. 22, allowing the scanning plane 246 including the focal point 243 to be scanned two-dimensionally.

With this optical probe 231A, the observation-use distal end face of the tip component 232 is angled, rather than being perpendicular to the lengthwise direction of the tip component 232, so when tissue is being observed with the optical probe 231A through an endoscope channel, regardless of whether the tissue is perpendicular to the lengthwise direction of the tip component 232 or is tubular tissue, the tip can be easily pressed against the tissue by tilting it about 45 degrees, for instance, making it easier to perform the observation.

Sixth Embodiment

A sixth embodiment of the present invention will now be described through reference to FIGS. 23 to 25. It is an object of this embodiment to provide an optical probe with which the frame rate can be increased, and the resolution in the Y direction can be raised. When raster scanning is performed using an optical probe, if only the information for the forward path or backward path is imaged out of the forward and backward scans, there will be fewer lines, the frame rate will be lower, and there will be a decrease in resolution in the vertical direction (the Y direction of the image).

On the other hand, there are hysteresis characteristics with a scanner that features piezoelectric elements, and the image is slightly different in the forward and backward paths, so if information is imaged for both forward and backward paths, the result will be a distorted image in which the images of the forward and backward paths are alternately woven into each other one line at a time.

Accordingly, the structure described below is employed to obtain an image with higher frame rate and so forth.

FIG. 23 shows the internal structure of an imaging device 251 in this embodiment. This imaging device 251 makes use of a first frame memory 252 and a second frame memory 253 instead of the frame memory 141 connected to the I/O port 144 in FIG. 6, and the digital signals for each line that have undergone A/D conversion by the A/D converter 140 are alternately stored in the first frame memory 252 and second frame memory 253 via signal lines 140b and 140c.

The switching between the first frame memory 252 and the second frame memory 253 by the A/D converter 140 is controlled by the CPU 143 via the signal line 143a, the I/O port 144, and a signal line 144e. The data stored in the first frame memory 252 and the second frame memory 253 is controlled so that it is alternately read out one line at a time from each frame memory via a signal line 143a, I/O port 144, and signal line 144a or 144f, by the CPU 143.

The storage addresses for the data in the first frame memory 252 and second frame memory 253 are specified by the CPU 143 through the address bus 145, and are controlled such that the data is stored in the main memory 142 through the data bus 146. The CPU 143 controls the system such that a hysteresis characteristic conversion program stored ahead of time in the hard disk device 150 is read out to the main memory 142, causing the data in the second frame memory 253 to be converted to the same characteristics as the data stored in the first frame memory 252.

The data in the first frame memory 252 and the data in the second frame memory 253 are alternately read out one line at a time from the main memory 142 to the I/O port 144, sent to the monitor 116, and imaged.

Figures 24A, 24B:
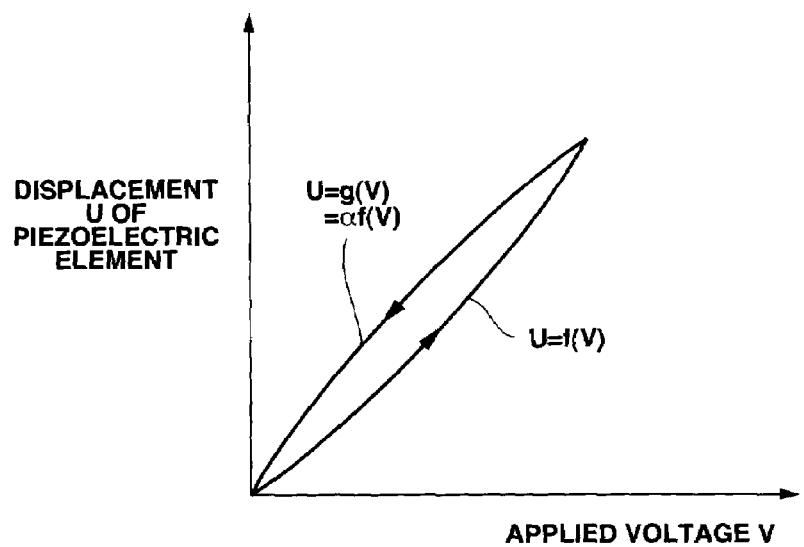
FIG. 24A is a graph of hysteresis characteristics in which the displacement of a piezoelectric element with respect to an applied voltage varies from the forward path to the backward path.
FIG. 24B is a table listing correction coefficients for correcting the hysteresis characteristics.
Figure 25:
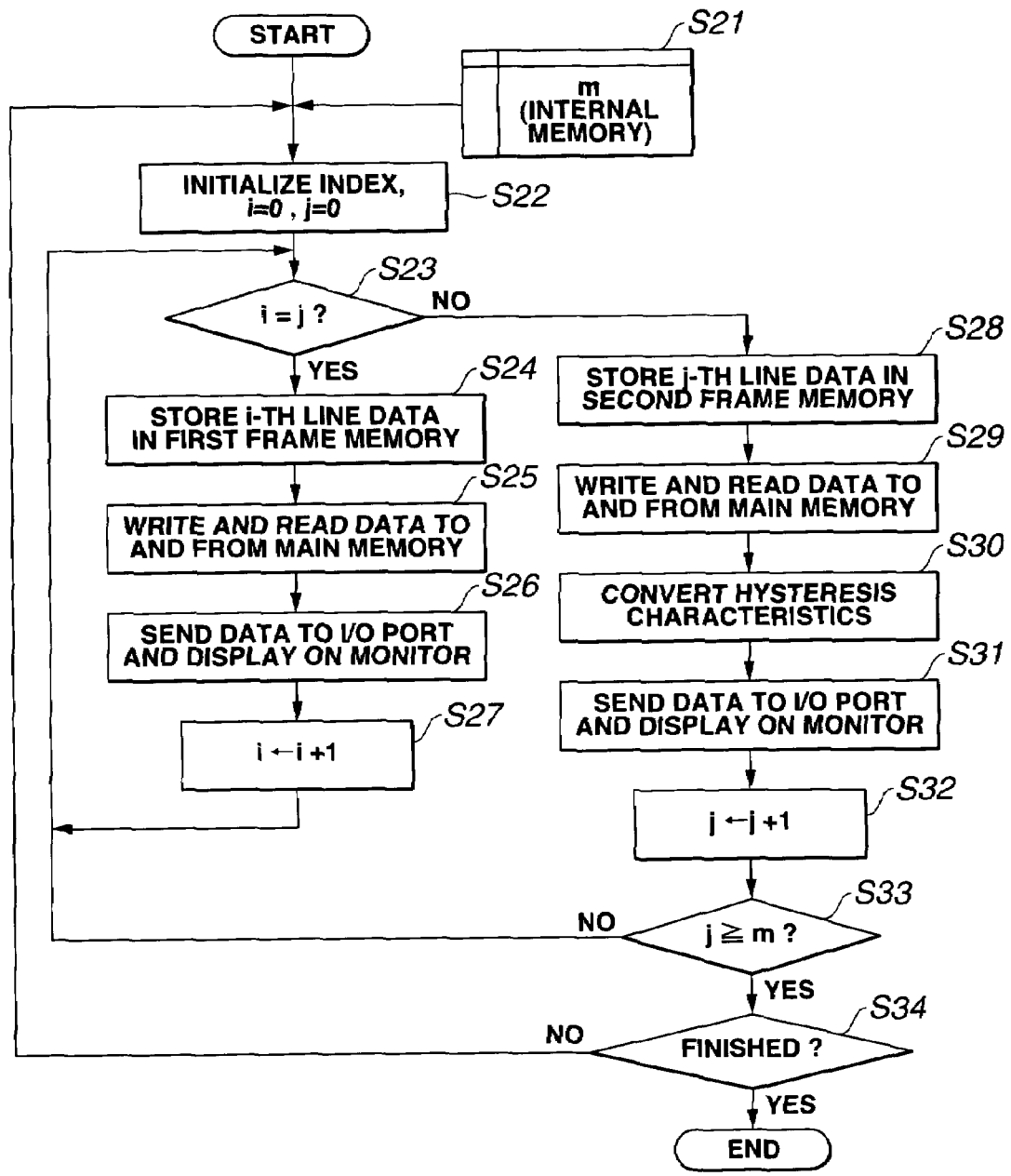

When the data is thus converted such that the hysteresis characteristics of the forward and backward paths shown in FIG. 24A are the same, or, in this case, when the characteristics of the backward path are made the same as the characteristics of the forward path, an image of both the forward path and the backward path is displayed with no distortion.

For example, if we let U be the amount of displacement of the piezoelectric element with respect to the applied voltage V, and if the displacement U on the forward path is expressed as U=f(V) and on the backward path as U=g(V), a correction coefficient α is introduced such that the equation will be U=αf(V), and correction coefficients α are readied in table form in the hard disk device 150, for example, as shown in FIG. 24B. On the forward path, the display is at a monitor screen location corresponding to the displacement U, while on the backward path, the display is at a monitor screen location at which the characteristics in the case of the forward path have been corrected with the correction coefficient α.

The above flow will be described using the flow chart of FIG. 25. Here, the number of lines in the first frame memory 252 and the second frame memory 253 is indicated by i and j, respectively, and the number of lines of one frame of image is 2m (where m is an integer). This m is stored in a register of the CPU 143, for example (step S21), and the indexes i and j are initialized to 0 (step S22).

In the next step S23, the CPU 143 compares the indexes i and j, and if they are equal, the i-th line of data is stored in the first frame memory 252 (step S24). The CPU 143 writes this i-th line of data to the main memory 142, and this line data is read out (step S25), and then the CPU 143 outputs the data to the monitor 116 via the I/O port 144, and causes this line data to be displayed on the monitor 116 (step S26). In the subsequent step S27 the index i is incremented by one, and the flow returns to step S23.

Thereupon, since i and j are no longer equal, the flow moves to step S28, and the CPU 143 causes the line data to be stored in the second frame memory 253, and causes it to be written to and read from the main memory 142 (step S29).

The CPU 143 controls the system such that the data read from the main memory 142 is used by a hysteresis conversion program stored ahead of time in the hard disk device 150 to convert the hysteresis characteristics thereof into characteristics that are the same as in the case of the forward path (step S30).

The CPU 143 then outputs the line data that has undergone this characteristic conversion to the monitor 116 via the I/O port 144, and causes the data to be displayed on the monitor 116 (step S31).

In the subsequent step S32 the index j is incremented by one, after which a decision is made as to whether j is equal to or greater than m (step S33). If not, the flow returns to step S23 and the processing of steps S23 to S32 are repeated until j is equal to or greater than m. One frame of image is obtained in this way. Then, in step S34 a decision is made as to whether to end the processing, and if the next frame is to be displayed, the flow returns to step S22, this processing is repeated, and the processing is ended when the next frame is not to be displayed.

The result of this processing is that two lines of image are obtained by forward and backward scans, so the frame rate is higher. Also, the resolution in the vertical direction (the Y direction of the image) can be enhanced without lowering the frame rate.

Seventh Embodiment

A seventh embodiment will now be described through reference to FIGS. 26 to 29D.

An optical probe system equipped with the seventh embodiment is such that in FIG. 1, for instance, the scanner of the optical probe 112I is provided with a strain sensor for detecting displacement, and the hysteresis characteristics when the scanner is driven are improved by this strain sensor.

Figure 26:
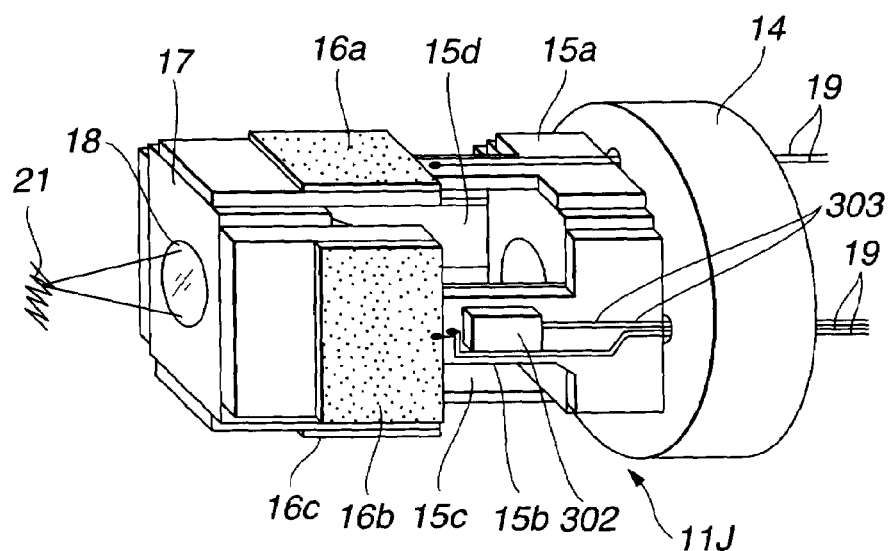

Accordingly, with the integral scanning type of optical probe in this embodiment, the optical unit 11G portion of the optical probe 112A in FIG. 2 is changed to the optical unit 11J shown in FIG. 26.

The optical unit 11J shown in FIG. 26 is like the optical unit 11G in FIG. 3, but a strain sensor 302 is adhesively fixed on the thin plate 15b that moves in the horizontal direction (X direction), in order to detect the displacement of this thin plate 15b.

Figure 27:
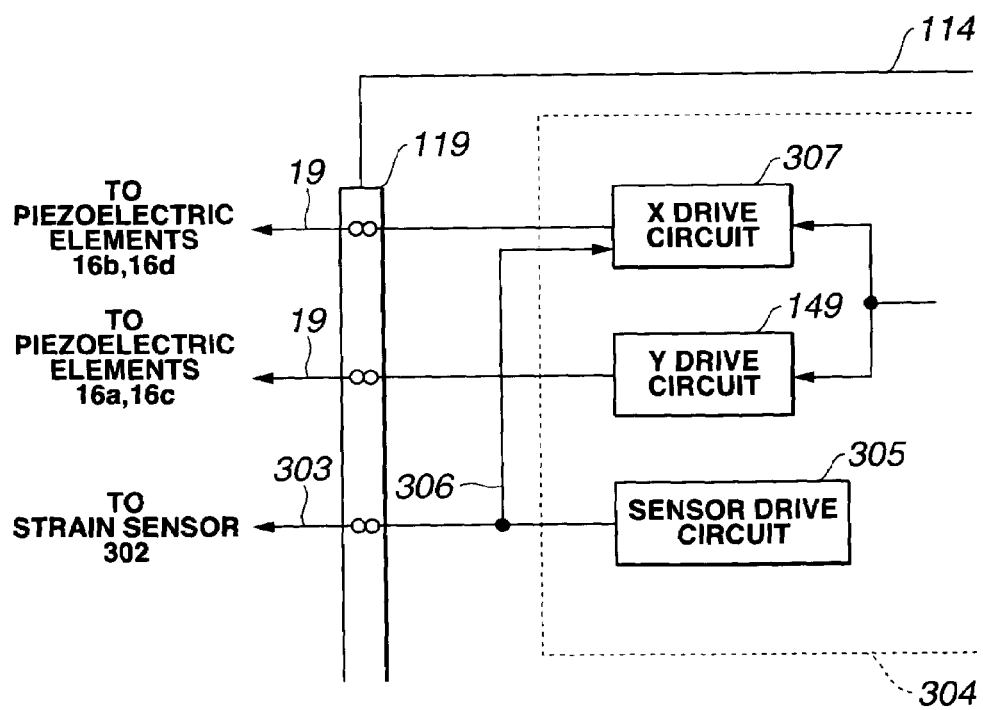

As shown in FIG. 27, a signal line 303 connected to this strain sensor 302 is electrically connected to a sensor drive circuit 305 within a control circuit 304, which controls the drive of the strain sensor 302. The output signal of the strain sensor 302 is inputted to an X drive circuit 307 via a signal line 306, an electrical signal corresponding to the displacement of the thin plate 15b is inputted, and drive in the X direction is controlled by this signal. In FIG. 27, a portion of the signal line 303 and the signal line 306 is shared.

As shown in FIG. 28, the X drive circuit 307 in this embodiment comprises a sine wave generator 308 that generates a signal for driving in the X direction, a drive signal correction circuit 309 that compares this sine wave with the electrical signal indicating the displacement of the strain sensor 302 and corrects the hysteresis characteristics of the scanning forward and backward paths, and an amplifier 310 that amplifies the signal for driving the piezoelectric elements 16b and 16d.

The sine wave signal generated by the sine wave generator 308 is inputted to the drive signal correction circuit 309. The sensor signal of the strain sensor 302 is inputted to the drive signal correction circuit 309 via the signal line 306, and the signal outputted to the amplifier 310 is outputted after being corrected by this sensor signal.

Similarly, with an optical fiber scanning type of optical probe, a strain sensor is attached to the thin plate 15b that constitutes the optical unit thereof. The rest of the structure is the same as in the sixth embodiment, and will therefore not be described again.

FIGS. 29A to 29D illustrate the operation of correcting the waveform when the output of the strain sensor 302 is different from the drive signal. In this case, a rising waveform indicates the forward path of scanning, and a falling waveform indicates the backward path of scanning.

If the sensor output (displacement signal) from the strain sensor 302 shown in FIG. 29B is different from the sine wave that is the drive signal in FIG. 29A, the drive signal correction circuit 309 compares the waveforms of these signals, and as shown in FIG. 29C, outputs a correction signal to the amplifier 310 that leaves the forward path as a sine wave but changes the waveform of the backward path so that the sine wave becomes flatter.

The waveform of the sensor output inputted by feedback from the strain sensor 302 to the drive signal correction circuit 309 is made to be in linear symmetry in the forward and backward paths, as shown in FIG. 29D. In other words, even if the waveforms are different in the forward and backward paths as shown in FIG. 29B when not corrected with the sensor output, there will be virtually no hysteresis characteristics in the forward and backward paths as shown in FIG. 29D after correction with the sensor output.

Thus correcting the hysteresis of the forward and backward paths before driving the piezoelectric elements 16b and 16d yields an image with no distortion in the forward and backward paths.

In this embodiment, the displacement of the piezoelectric element 16b or 16d is detected by the strain sensor (strain gauge), but piezoelectric elements with smaller hysteresis characteristics may also be used.

With this embodiment, two lines of image are obtained by forward and backward scanning, so the frame rate is higher. Also, the resolution in the vertical direction (the Y direction of the image) can be enhanced without lowering the frame rate.

Figure 30:
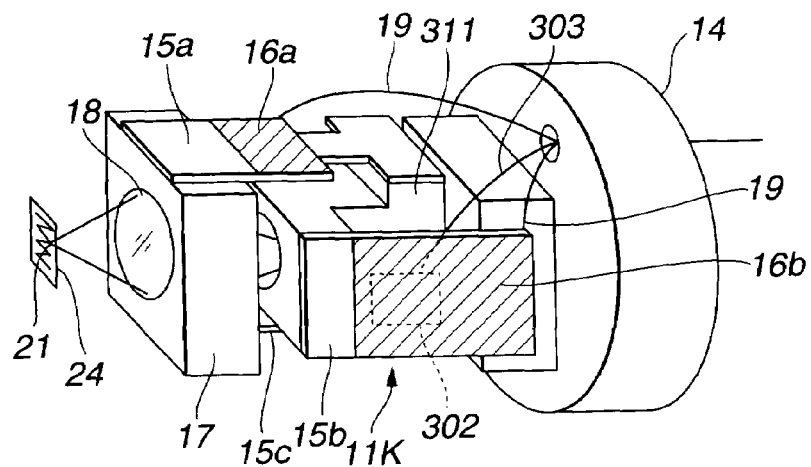

FIG. 30 shows an optical unit 11K in a first variation example. This optical unit 11K is structured differently from the optical unit 11J in FIG. 41, so its structure will be described.

With this optical unit 11K, both sides of the distal ends of a relay member 311, rather than the lens holder, are fixed to both sides of the distal ends of the thin plates 15b and 15d (15d is not shown in the figure) whose rear ends are adhesively fixed to both side faces of the base 14, the rear ends of the thin plates 15a and 15c are affixed to the upper and lower surfaces at the rear end of this relay member 311, and the upper and lower surfaces of the lens holder 17 are affixed to the distal ends of these thin plates 15a and 15c.

Figure 45:
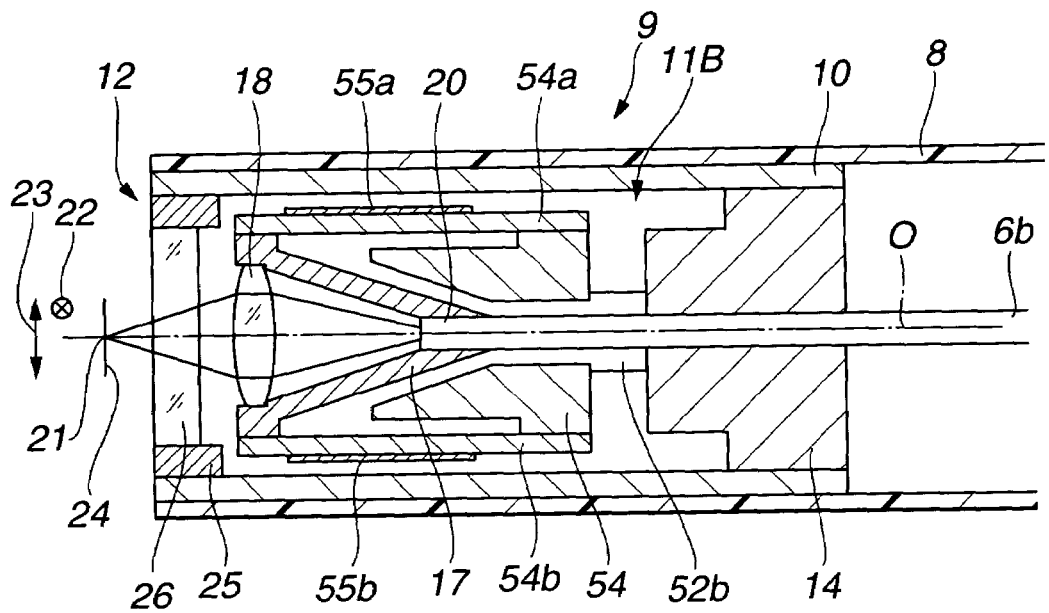
FIGS. 45 and 46 pertain to a twelfth embodiment of the present invention.

The piezoelectric elements 16b and 16d, and 16a and 16c (16d and 16c are not shown) are applied to the outer surfaces of the thin plates 15b and 15d, and 15a and 15c, respectively. In this first variation example, the strain sensor 302 is applied to the inner surface of the thin plate 15b. The rest of the structure is the same as in the optical unit 11J. In FIG. 45, the signal lines 19 and 303 are shown as a single line for the sake of simplicity.

Figure 31:
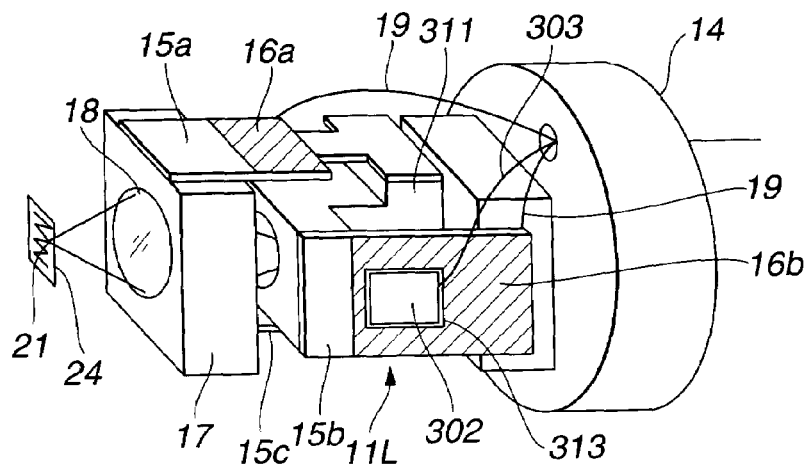
Figure 32:
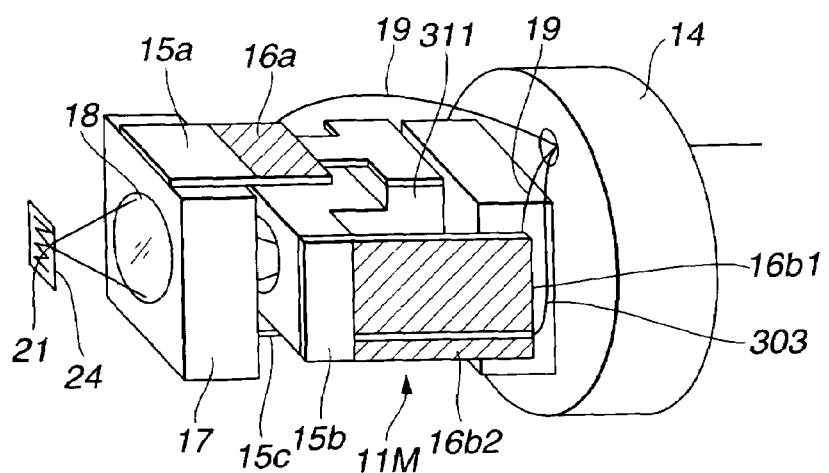

FIGS. 31 and 32 illustrate optical units 11L and 11M in second and third variation examples, respectively. In FIG. 31, the strain sensor 302 is attached to the upper surface of the piezoelectric element 16b via an insulating plate 313 made of polyimide or another such insulating material.

In FIG. 32, two piezoelectric elements 16b1 and 16b2 are used for the piezoelectric element applied to the thin plate 15b, with one of these, the piezoelectric element 16b2, being used as a sensor.

The effect of these variation examples is substantially the same as that with the optical unit 11J.

Eighth Embodiment

An eighth embodiment of the present invention will now be described through reference to FIG. 33. It is an object of this embodiment to provide an optical probe with which tomograms can be obtained at different depth locations.

Figure 33:
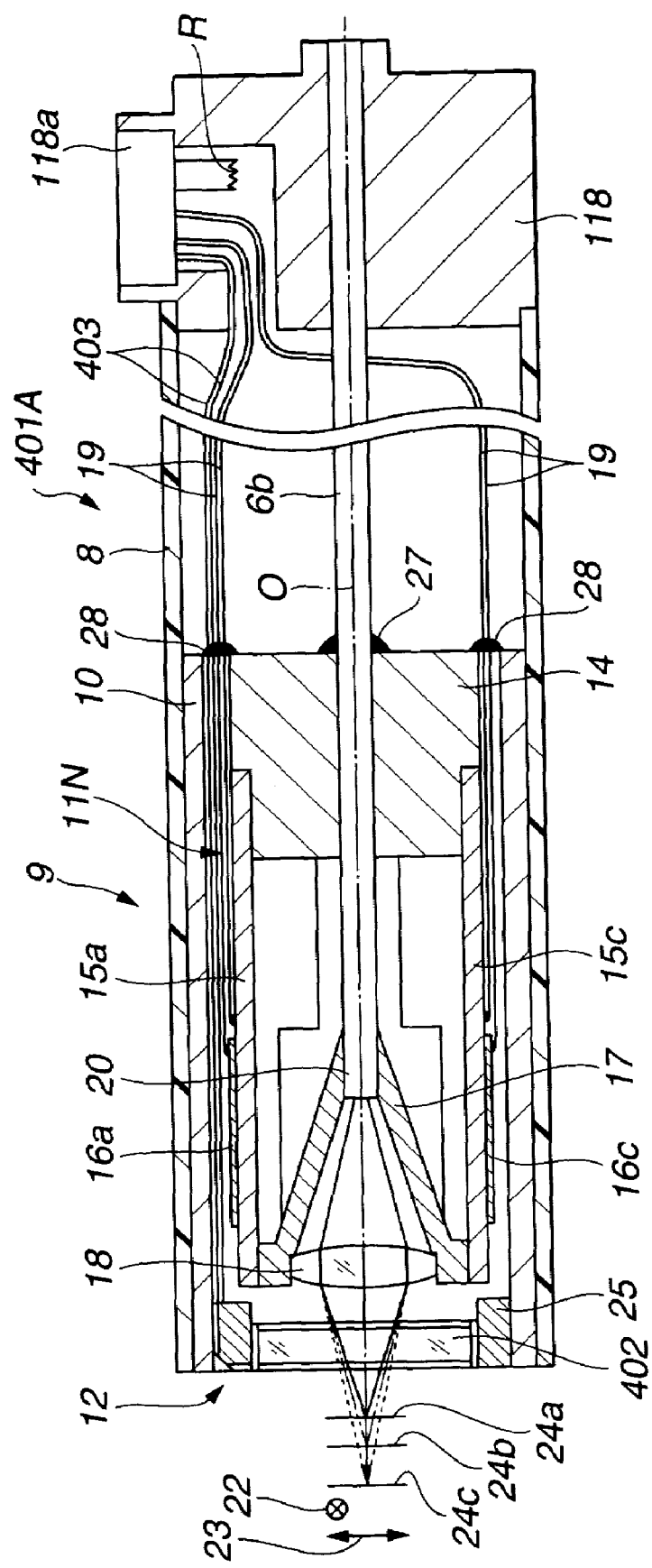
FIG. 33 is a cross section of the structure of the optical probe in an eighth embodiment of the present invention.

The optical probe 401A in FIG. 33 is like the optical probe 112A in FIG. 2, but has an optical unit 11N that employs a liquid crystal lens 402 that varies the refractive index through the application of voltage, instead of the cover glass 26 that constituted the optical unit 11G. With this liquid crystal lens 402, a liquid crystal is sealed within transparent, parallel containers provided with transparent electrodes, and is attached to the distal end of the optical frame 10 via the cover holder 25. The read end of a signal line 403 connected to both of the transparent electrodes is connected to the electrical contact of the electrical connector 118a, and connected to a voltage generation circuit via a depth (or refractive index) adjustment switch (not shown) provided to the control device 114 (see FIG. 1).

When this depth adjustment switch is operated, voltage that will achieve a refractive index corresponding to the selected depth is applied to the liquid crystal lens 402.

The scanning planes 24a, 24b, and 24c can be scanned with the focal position varied in three stages, for example, by adjusting the applied voltage in three stages. The applied voltage may also be varied continuously so that scanning is performed a continuously varying depth.

Therefore, with this embodiment, tomograms of sites at different depths can be obtained with ease.

In FIG. 33, an integrated scanning type of optical probe 401A was described, but an optical fiber scanning type of optical probe can also be employed by using the liquid crystal lens 402 for the optical probe 112B in FIG. 4 as well.

Ninth Embodiment

A ninth embodiment of the present invention will now be described through reference to FIG. 34. It is an object of this embodiment to provide an optical probe with which the scanner can be vibrated stably.

Figure 34:
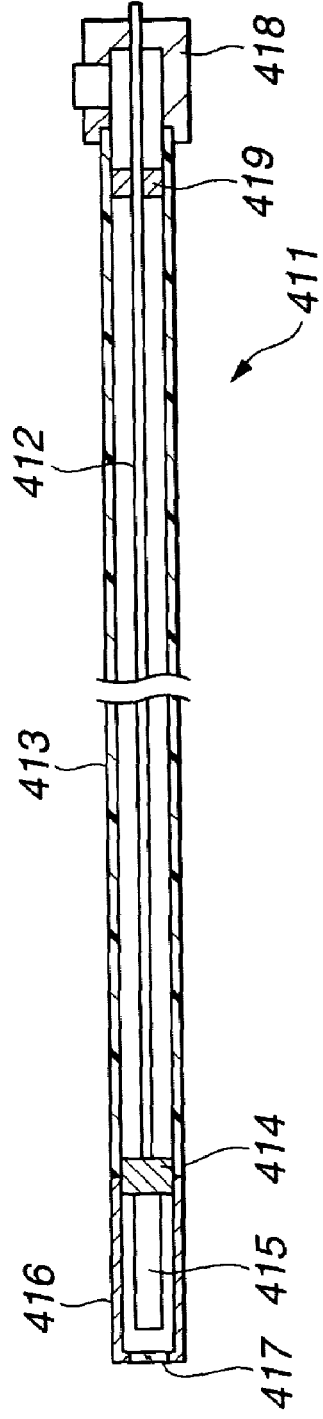
FIG. 34 is a cross section of the structure of the optical probe in an ninth embodiment of the present invention.

As shown in FIG. 34, the optical probe 411 in this embodiment is designed such that a rigid base member 414 is attached to the distal end of a flexible tube 413 into which an optical fiber 412 has been inserted, the proximal end of a scanner 415 (either an optical fiber and object lens integrated scanning type or an optical fiber scanning type) is fixed to this base member 414, and the proximal end of a rigid distal end frame 416 covering this scanner 415 is fixed to the base member 414.

An opening is provided to the portion of the distal end frame 416 irradiated by the light emitted from the scanner 415, and this opening is blocked off by a cover glass 417 through which light passes.

The optical fiber 412 inserted through the tube 413 is fixed by a fixing component 419 near a connector 418 at the rear end of the tube 413. In other words, the optical fiber 412 is fixed at a position where vibration from the scanner 415 is not transmitted.

Therefore, when the scanner is vibrated, vibration from the optical fiber 412 does not reach the fixing component thereof, allowing the scanner to be vibrated more stably.

Figure 35:
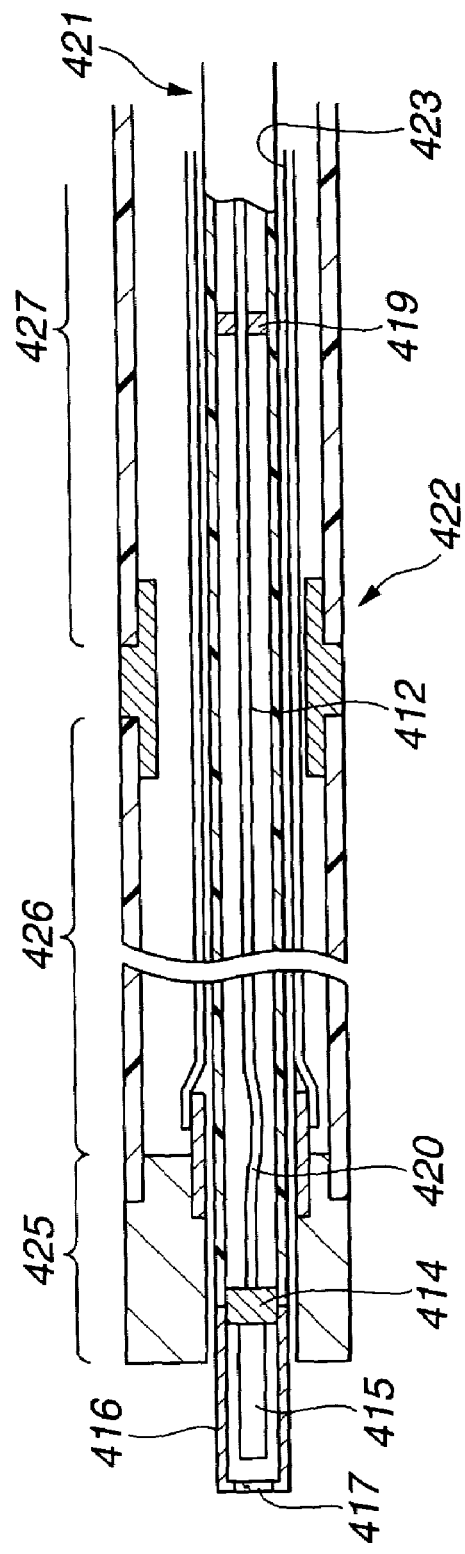
FIG. 35 is a cross section of a state in which the optical probe in a variation example of the ninth embodiment has been inserted into an endoscope.

FIG. 35 shows the state when an optical fiber 421 in a first variation example has been inserted into a channel 423 of an endoscope 422.

The endoscope 422 comprises a tip component 425 with a rigid insertion component, a bendable bending component 426, and a flexible tube 427 that is slender and flexible. The optical fiber 421 is inserted into the channel 423 provided to this insertion component.

With this optical probe 421, the fixing component 419 that fixes the optical fiber 412 is provided at the location of the flexible tube 427 to the rear of the bending component 426. This location is to the rear of the fixing component of the scanner 415 by at least the length L of the scanner 415, and is also an integer multiple of the length L (the location of mL, where m is an integer).

Also, this optical fiber 412 is fixed by the fixing component 419 in a state in which play 420 (or slack) is provided between the fixing component 419 and the fixing component of the scanner 415. This makes it possible to accommodate situations in which the optical probe 421 is bent.

Tenth Embodiment

A tenth embodiment of the present invention will now be described through reference to FIG. 36. It is also an object of this embodiment to provide an optical probe with which the scanner can be vibrated stably. FIG. 36 shows an optical unit 431 in the tenth embodiment.

With this optical unit 431, a side face 432a is formed by cutting off one side of a substantially annular base member 432, the rear end of a flat piezoelectric actuator 433 that serves as the low-speed drive side is affixed to this side face 432a, and the front end of this piezoelectric actuator 433 is affixed to the outer side face at the front end of a substantially L-shaped (when viewed from above) relay member 434. The piezoelectric actuator 433 comprises a flat member to which is applied a piezoelectric element that is flat and is provided on both sides with electrodes.

The front end of this relay member 434 faces the side surface near the front end of a square lens holder 436 to which an object lens 435 is attached.

A cylindrical extension 436a extends to the rear from the lens holder 436, to which is affixed an optical fiber 437 that passes through a through hole in the relay member 434 and the base member 432.

The object lens 435 and the tip component of the optical fiber 437 can be vibrated in the horizontal direction indicated by 439h by applying a drive signal to the piezoelectric actuator 433 via a signal line 438a.

A side plate portion of the relay member 434 extends to the rear in parallel with the flat piezoelectric actuator 433, and its rear end is integrally formed with a square support block 434a that faces the front of the base member 432. The rear end of a flat piezoelectric actuator 440 that serves as the high-speed drive side is affixed to the top of this support block 434*a*, and the distal end of the piezoelectric actuator 440 is affixed to the top at the front end of the lens holder 436.

A signal line 438*b* is affixed by solder 441 near the top of the support block 434*a* and connected to the electrode on the top side of the piezoelectric element that makes up the piezoelectric actuator 440, and the electrode on the lower surface of this piezoelectric actuator 440 is such that the signal line 438*b* is affixed by solder 441 near the top of the lens holder 436 and connected to the flat member (that constitutes the piezoelectric actuator 440) electrically connected to this electrode.

In other words, the signal line 438*b* for applying drive signals is connected near both ends of the piezoelectric actuator 440. The result of fixing at both ends in this way is that there is no need to solder to the middle portion of the piezoelectric element that undergoes the most deformation, so the piezoelectric element is resistant to cracking, and less vibration reaches the signal line 438*b* than when the connection is in the middle.

Also, the signal line 438*b* extends such that it turns back in the lengthwise direction of the piezoelectric actuator 433 and the side plate portion of the relay member 434, and the middle thereof is spot-bonded at suitable intervals, which keeps it from being exposed to excessive vibration.

When a drive signal is applied to the piezoelectric actuator 440 via the signal line 438*b*, the object lens 435 and the tip component of the optical fiber 437 are vibrated up and down in the direction indicated by 439*v*.

This optical unit 431 is covered by a tip cap 444, to the distal end of which is attached a cover glass 443 as shown by the broken lines.

With this embodiment, the scanner portions that are vibrated horizontally and vertically (up and down) are constituted by the flat construction piezoelectric actuators 433 and 440, respectively, so the vibration can be at a higher amplitude and a wider range can be observed than with a parallel plate construction in which the components are disposed facing each other in parallel.

Also, the signal line 438*b* for applying drive signals to the piezoelectric actuator 440 on the high-speed drive side, whose rear end is fixed to the rear end of the relay member 434, is disposed in the lengthwise direction of the piezoelectric actuator 433 on the low-speed drive side and in the lengthwise direction of the relay member 434, and its middle is spot-fixed at suitable intervals, so stable vibration can be ensured.

For instance, if the signal line 438*b* is merely given some play, vibration can cause the signal line to become entangled with the optical fiber, resulting in unstable scanner vibration, and there is also the possibility that the signal line will become so entangled with the optical fiber that the signal line is broken by the vibration of the optical fiber, but these are prevented from happening with this embodiment.

FIGS. 37 and 38 show an optical unit 452 provided to the tip component of an optical probe 451 in a variation example.

In this variation example, the high-speed drive actuator consists of two piezoelectric actuators disposed in parallel, while the low-speed drive actuator consists of a single piezoelectric actuator.

With the optical unit 452 in this variation example, the rear ends of two parallel thin plates 453*a* and 453*b* are affixed as shown in FIG. 37 to the upper and lower surfaces of the support block 434*a* in the optical unit 431 in FIG. 36, and the front ends of the thin plates 453*a* and 453*b* are affixed to the lens holder 436.

Flat high-speed piezoelectric elements 454*a* and 454*b* are applied (formed as high-speed piezoelectric actuators) on the thin plates 453*a* and 453*b*, respectively.

The side plate portion extending toward the front from one side face of the support block 434*a* in the relay member 434 is formed shorter than in FIG. 36, and the low-speed piezoelectric actuator is attached between this side face portion and the base member 432.

In other words, as shown in FIG. 38, the distal and rear ends of the thin plate 455 are affixed to the distal end of the side face portion of the relay member 434 and to the side face of the base member 432, respectively, and the flat low-speed piezoelectric element 456 is applied to this thin plate 455.

In this variation example, the piezoelectric actuator for high-speed drive consists of two parallel sets, and the piezoelectric actuator for low-speed drive consists of just one set. The rest of the structure is almost the same as that described for FIG. 36, and will therefore not be described again.

The effect with this variation example is complementary to that in FIG. 36. That is, the scanning range is narrower than in FIG. 36, but an advantage is that high-speed scanning can be performed more easily.

Eleventh Embodiment

An eleventh embodiment of the present invention will now be described through reference to FIGS. 39 to 44.

Figure 39:
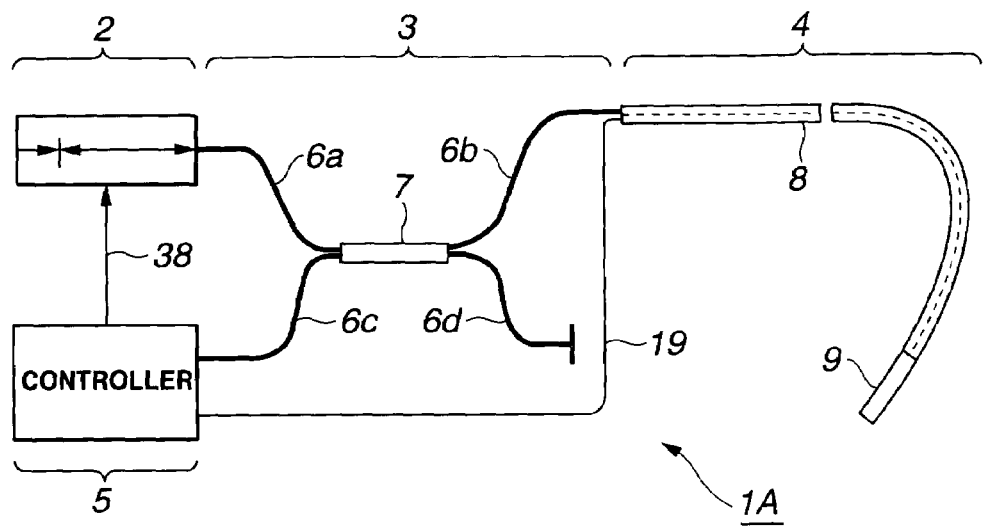
FIGS. 39 to 44 pertain to an eleventh embodiment of the present invention.

As shown in FIG. 39, an optical scanning microscope 1 equipped with the eleventh embodiment of the present invention comprises a light source component 2 that generates light, an optical transmission component 3 that transmits this light, an optical scanning probe device (hereinafter referred to simply as optical scanning probe or optical probe) 4 that is formed slender enough to be inserted into a body cavity or the like and that shines the light coming from the optical transmission component 3 from its tip toward the examination site and guides the return light thereof back to the optical transmission component 3, and a control component 5 that detects the return light coming from the optical probe 4 through the optical transmission component 3 and performs signal processing for imaging, control over optical scanning means provided in the optical probe 4, and so forth.

The light source component 2 is, for example, a laser oscillation device that outputs laser light. This laser light will be suited to cell observation if it is from an argon laser with a wavelength of 488 mm.

The optical transmission component 3 comprises optical transmission fibers (hereinafter referred to merely as fibers) 6*a*, 6*b*, 6*c*, and 6*d* and a four-terminal coupler 7 that branches these fibers in two directions and performs photocoupling. The fibers 6*a*, 6*b*, 6*c*, and 6*d* are single mode fibers.

The end of the fiber 6*a* is connected to the light source component 2, the end of the fiber 6*c* is connected to the control component 5, and the end of the fiber 6*d* is connected to (blocked off by) a non-reflecting device or the like.

The fiber 6*b* is long and slender, passing through the inside of the flexible tube 8, for example, that constitutes the sheath of the optical probe 4, and being guided to the tip component 9. This optical probe 4 can also be inserted into an instrument channel of an endoscope and inserted into a body cavity, for example.

The light source component 2, the optical transmission component 3, and the control component 5 constitute an observation device connected to the optical probe 4. The reflected light from the examination site resulting from the optical scanning of the optical probe 4 is detected and guided to the observation device, this light is imaged by the control component 5 (discussed below) within the observation device, and a confocal type of microscope image featuring optical scanning is displayed by a displayed means.

Figure 40:
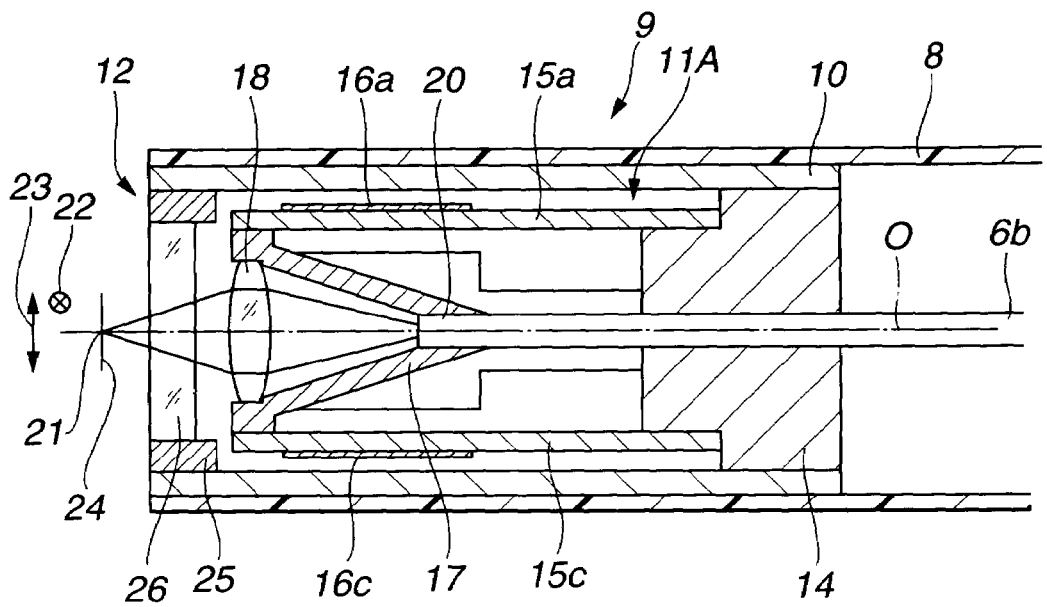

As shown in FIG. 40, the tip component 9 comprises the rigid, annular optical frame 10 attached at one end to the distal end of the tube 8, an optical unit 11A attached to the inside of this optical frame 10, and a tip cover unit 12 (transparent and rigid) that serves as a transparent window member that is pressed against the examination site, and that is attached to the distal end of the optical frame 10 via a piezoelectric element 28 (discussed below).

The tip of the slender optical fiber 6b inserted into the tube 8 is fixed to the optical unit 11A, the light emitted from the tip of this optical fiber 6b is condensed and directed at the examination site via an optical scanning mechanism (scanner), and the reflected light (return light) from the examination site is received by this optical fiber 6b.

Figure 41:
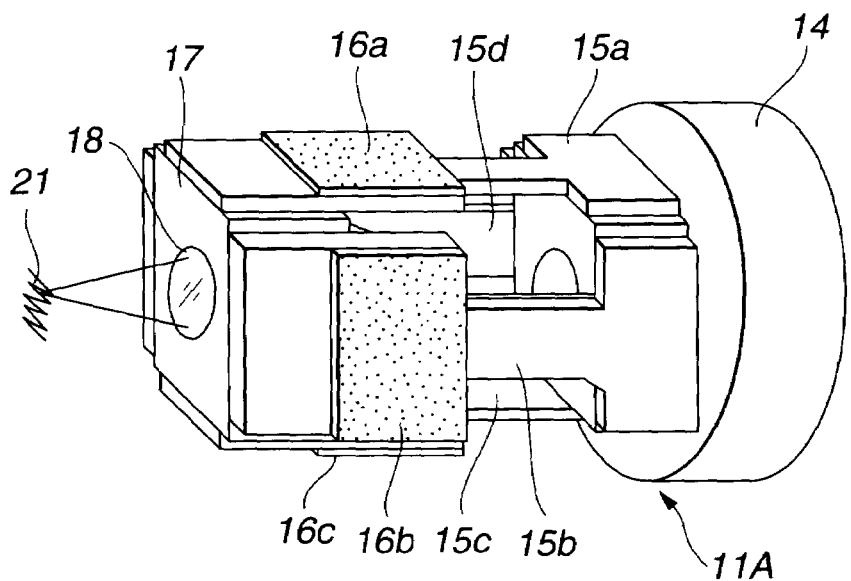

The optical unit 11A portion shown in the cross section of FIG. 40 is shown in detail in the perspective view of FIG. 41. This optical unit 11A is structured as follows.

The base 14 of the optical unit 11A is fixed to the optical frame 10. The base 14 is designed to be heavier than the lens holder 17 and object lens 18 (discussed below) so that it will stay in place better. The tip end of the optical fiber 6b is inserted in a center hole of the base 14, and the part of the optical fiber 6b near the tip that is press-fitted to the inner wall of the hole in the base 14 is fixed.

Two sets of parallel thin plates 15a, 15b, 15c, and 15d are fixed at the rear end to the base 14. More specifically, the thin plates 15a and 15c and the thin plates 15b and 15d, which constitute parallel flat springs, are parallel to each other in their plate planes, respectively, the thin plate 15a (or 15c) is disposed such that its plate plane is perpendicular to that of the thin plate 15b (or 15d), the rear end of each plate is fixed to the base 14, and the distal end (as opposed to the rear end) is capable of elastic deformation up and down and to the left and right.

Each thin plate 15i (i=a, b, c, or d) has mounted to it, at a location near the front of the thin plate 15i, a piezoelectric element 16i (16d is not shown) in the form of a plate polarized in the thickness direction. Each piezoelectric element 16i is a unimorph piezoelectric element. The electrodes on either side of each piezoelectric element 16i are each connected to cables 19 (see FIG. 39) for driving these piezoelectric elements 16i, and are connected through the inside of the tube 8 to the (drive means of the) control component 5.

The lens holder 17 is adhesively fixed to the distal ends of the four thin plates 15i, and to this lens holder 17 are fixed the object lens 18 (which serves as a condensing optical system) and the tip component of the optical fiber 6b (which serves as a light transmission means), that is, the optical fiber tip 20. This lens holder 17 has a frame for attaching the object lens 18, and a frame extension that extends conically from this frame toward the rear, and the optical fiber tip 20 is fixed by being press-fitted into a small hole provided at the apex of this frame extension, which is located on the optical axis O of the object lens 18 (the optical fiber tip component (optical fiber end component) 20 is disposed on the optical axis O of the object lens 18).

When a drive signal is applied to the piezoelectric element 16i, the combination of the plate-shaped piezoelectric element 16i and the thin plate 15i deforms such that the tip end thereof bends perpendicularly to the plate plane with respect to the rear end, the lens holder 17 held at the tip is designed to be able to move in the direction of the bending caused by this deformation, and the object lens 18 and the optical fiber tip 20 held by the lens holder 17 both move, allowing the emitted light to be scanned.

Here, the spreading emitted light is condensed by the object lens 18 using the extremely slender optical fiber tip 20 as the focal point, with the light being emitted so as to be focused at the position of a focal point 21 on the examination site side.

The focal point 21 is scanned in the horizontal direction (X direction) 22 and the vertical direction (Y direction) 23 in FIG. 40 by driving the piezoelectric elements 16a, 16b, 16c, and 16d, allowing the scanning plane 24 including the focal point 21 to be scanned. This scanning plane 24 is substantially perpendicular to the axial direction of the optical probe 4.

The object lens 18 is one with a numerical aperture of at least 0.3, for example.

Meanwhile, the tip cover unit 12 consists of a cover holder 25 and a cover glass 26 fixed to this cover holder 25. The cover holder 25 is fixed to the distal end of the optical frame 10. The construction here is such that the probe tip component is sealed.

Figure 42:
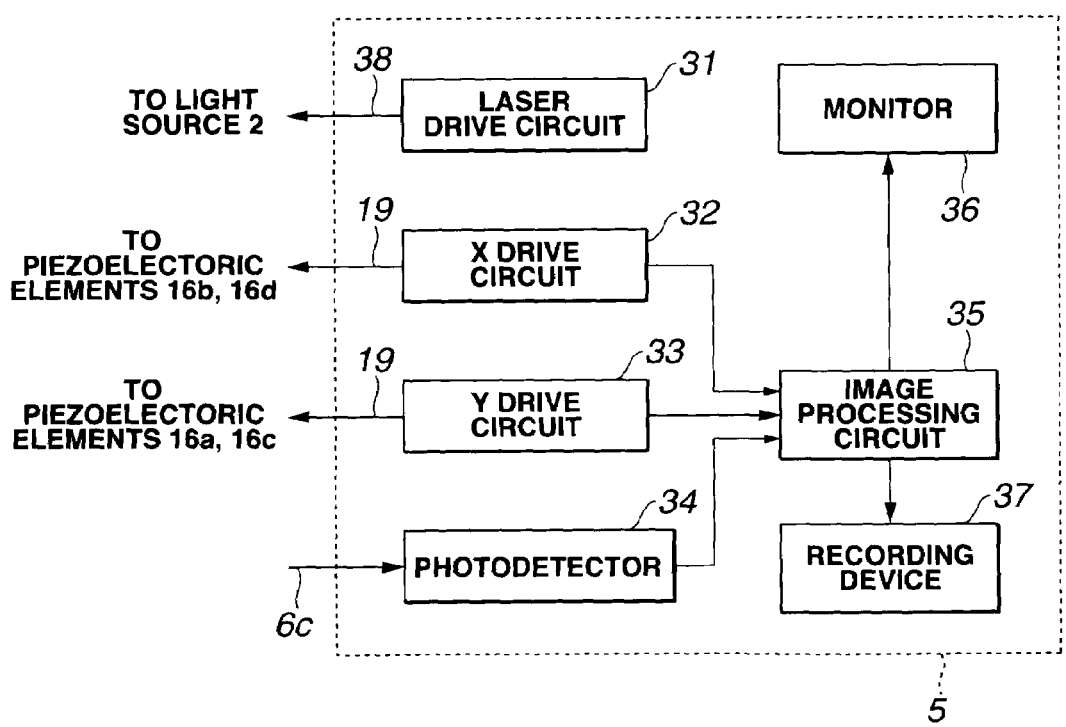

FIG. 42 illustrates the control component 5.

The control component 5 comprises a laser drive circuit 31 for driving the laser of the light source component 2, an X drive circuit 32 for driving the piezoelectric elements 16b and 16d, a Y drive circuit 33 for driving the piezoelectric elements 16a and 16c, a photodetector 34 with a built-in amplifier for subjecting the output light from the optical fiber 6c to photo-electrical conversion, an image processing circuit 35 for performing image processing on the output signal from the photodetector 34, a monitor 36 for displaying a microscope image using reflected light from the scanning of the scanning plane 24 by input of a video signal produced by the image processing circuit 35, and a recording device 37 for recording the video signal produced by the image processing circuit 35. The internal connections of the control component 5 are as shown in FIG. 42.

The laser drive circuit 31 is connected to the light source component 2 by a cable 38. The X drive circuit 32 is connected to the piezoelectric elements 16b and 16d via a cable 19, and the Y drive circuit 33 is connected to the piezoelectric elements 16a and 16c via another cable 19.

When the piezoelectric elements 16b and 16d are driven at high speed by the X drive circuit 32 via the cable 19, and the piezoelectric elements 16a and 16c are driven slowly by the Y drive circuit 33 via the other cable 19, the scanning plane 24 is two-dimensionally scanned as shown in FIG. 43.

For instance, the scanning range in the X direction 22 can be increased by increasing the amplitude of the voltage driving the piezoelectric elements 16b and 16d, and the scanning range in the Y direction 23 can be increased by increasing the amplitude of the voltage driving the piezoelectric elements 16a and 16c, so the desired scanning range can be obtained with ease.

Figure 44:
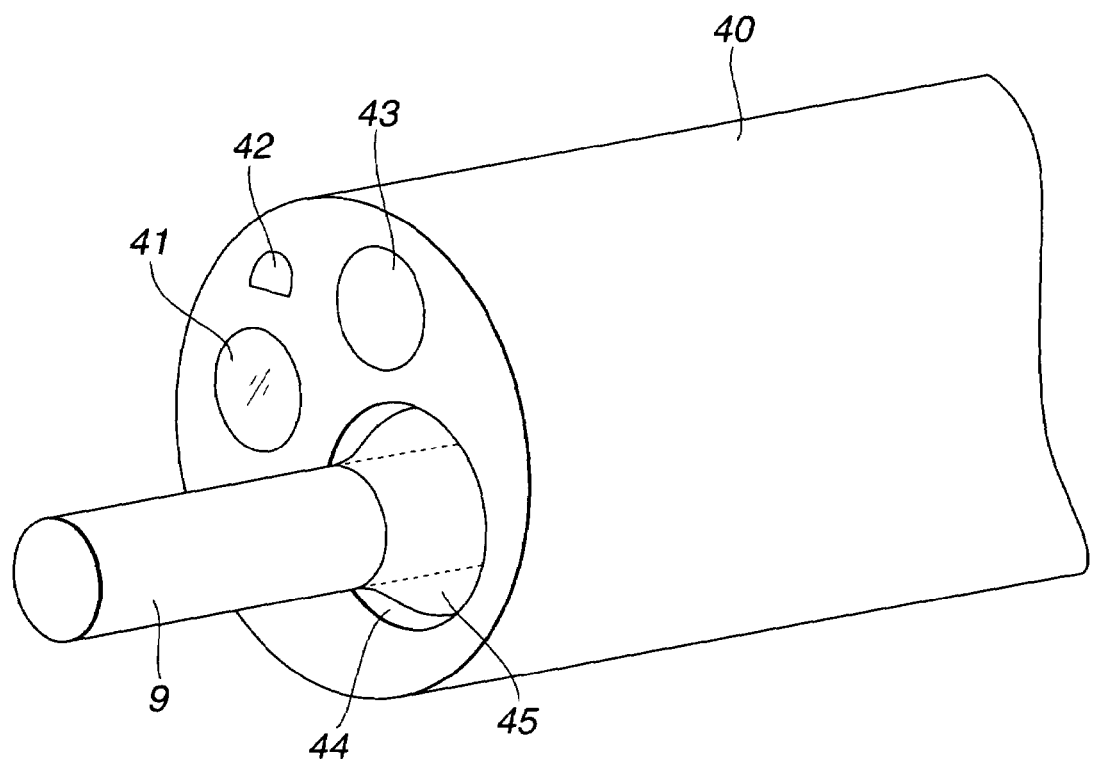

FIG. 44 illustrates the use of the optical probe 4 combined with an endoscope. The endoscope tip component 40 is provided with an endoscopic object lens 41, a nozzle 42 for washing the object lens, a light guide 43, and a forceps channel 44. This optical probe 4 is used by being inserted into the forceps channel 44 as in FIG. 44. A balloon 45 is provided to the outer surface toward the rear of the tip component 9 of the probe 4, an air tube (not shown) is connected, and a syringe (not shown) is connected to the air tube.

With this embodiment, light from the light source component 2 is transmitted by the slender optical fiber 6b inserted in the optical probe 4 to the tip of this fiber, and is directed at the examination site by the object lens 18 serving as a condensing optical system fixed (supported) along with the tip face by the lens holder 17 (serving as a fixing or supporting means). Here, the lens holder 17 is scanned at high speed in the horizontal direction by applying a sine wave as an AC signal to the piezoelectric elements 16b and 16d that make up the scanning means, and light is also scanned in the vertical direction by applying a low-frequency triangular wave to the piezoelectric elements 16a and 16c, the result being that reflected light is obtained from the focal point position, and a scanning image is obtained.

With this structure in which the lens holder 17 supporting the tip face of the optical fiber 6b and the object lens 18 is moved by a scanning means (drive means), the desired scanning range can be covered, there is no need for a special object lens 18, allowing the lens design to be simple, and resolution can be increased by raising the numerical aperture.

The operation of this embodiment will now be described.

First, the syringe (not shown) is used to inflate the balloon 45 in order to fix the tip component 9 of the optical probe 4 with respect to the endoscope tip component 40. The tip component 9 is then pressed against the area to be examined. The image of the examination site here is not very blurry because the tip component 9 is fixed.

The light source component 2 driven by the laser drive circuit 31 emits laser light that is incident on the optical fiber 6a. This laser light is split in two by the four-terminal coupler 7, one of the beams is guided to the blocked-off end, and the other beam is guided through the optical fiber 6b to the tip component 9 of the optical probe 4.

This laser light is spread out and emitted such that the optical fiber tip 20 is the focal point, after which it is condensed by the object lens 18, then passes through the cover glass 26, after which it reaches the focal point 21 at the examination site. The light reflected from the focal point 21 travels the same optical path as the incident light, and is again incident on the fiber at the optical fiber tip 20. In other words, the optical fiber tip 20 and the focal point 21 of the examination site are in a confocal relationship with respect to the object lens 18.

The reflected light that is not at this focal point 21 cannot travel the same optical path as the incident light, and therefore virtually none of it is incident on the fiber of the optical fiber tip 20. Therefore, the optical probe 4 forms a confocal optical system.

The piezoelectric elements 16b and 16d are driven by the X drive circuit 32 of the control component 5 in this state. The operation of the piezoelectric elements 16i will be described.

The thickness of the piezoelectric elements 16i changes when voltage is applied to them. The thickness increases when a positive voltage is applied to the piezoelectric elements 16i, which is accompanied by contraction of the piezoelectric elements 16i in the lengthwise direction. Because the piezoelectric elements 16i are bonded to thin plates 15i whose length does not change at this point, there is an overall deformation involving curvature toward the piezoelectric elements 16i.

Conversely, the thickness decreases when a negative voltage is applied to the piezoelectric elements 16i, which is accompanied by expansion of the piezoelectric elements 16i in the lengthwise direction. Because the piezoelectric elements 16i are bonded to thin plates 15i whose length does not change, there is an overall deformation involving curvature toward the thin plates 15i. If drive signals of different polarity are applied to the two opposing piezoelectric elements 16b and 16d such that one is deformed toward the piezoelectric element and one toward the thin plate, these piezoelectric elements will be deformed in the same direction as the horizontal direction 22.

When alternating current of opposite polarity is applied to the piezoelectric elements 16b and 16d, the lens holder 17 vibrates, this causes the object lens 18 and the optical fiber tip 20 to move, and the position of the focal point 21 of the laser light is scanned in the X direction 22 of the scanning plane 24 (perpendicular to the paper plane in FIG. 40).

In this case, significant displacement results from driving this system at a resonant frequency. Just as with the X drive, the position of the focal point 21 of the laser light is scanned in the Y direction 23 of the scanning plane 24 by the Y drive circuit 33. Here, the frequency of vibration in the Y direction is made sufficiently slower than the frequency of scanning in the X direction, the result of which is that the focal point is scanned over the scanning plane 24 as shown in FIG. 43 from top to bottom (Y direction) while vibrating at high speed in the horizontal direction. Along with this, the reflected light at the various points of the scanning plane 24 is transmitted by the optical fiber 6b.

The light incident on the optical fiber 6b is split in two by the four-terminal coupler 7, guided through the fiber 6c to the photodetector 34 of the control component 5, and detected by the photodetector 34. Here, the photodetector 34 outputs an electrical signal corresponding to the intensity of the incident light, and this signal is amplified by a built-in amplifier (not shown).

This signal is sent to the image processing circuit 35. The image processing circuit 35 refers to the drive waveforms of the X drive circuit 32 and the Y drive circuit 33 to calculate the focal point position corresponding to the signal output, further calculates the intensity of the reflected light at this point, and repeats this procedure to image the reflected light of the scanning plane 24. This result is temporarily stored as image data in the image memory of the image processing circuit 35, this image data is read out in synchronization with a synchronization signal, and a two-dimensional image of the reflected light intensity of the focal point position when the scanning plane 24 is scanned is displayed on the monitor 36. If needed, the image data is recorded in the recording device 37.

A single mode fiber was used as an example in this embodiment, but this embodiment is not limited to such use, and a multi-mode fiber that performs the same role may be used instead.

Also, the piezoelectric elements are not limited to a unimorph type, and a bimorph type may be used instead.

This embodiment has the following effects.

Since the optical fiber tip 20 and the object lens 18 are driven together, the optical system is simple, and a high-performance optical system can be realized with ease.

To describe this in more specific terms, because both the optical fiber tip 20 and the object lens 18 are driven together, rather than either one being driven alone, there is almost no change in the relationship of the two when they are being driven and not being driven, and this solves the problem encountered with prior art of the difficulty in designing a lens which focused when just one of these components was driven. In other words, the object lens 18 is easier to design. Alternatively, no special lens system need be used.

As discussed above, the positional relationship between the optical fiber tip 20 and the object lens 18 is maintained such that it is virtually unaffected by the drive state, so if the system is designed such that the light emitted from the optical fiber tip 20 disposed at the focal point position of the object lens 18 on the optical axis O thereof can be efficiently condensed by the object lens 18, then this relationship will be maintained even when the components are driven, and a high-resolution scanning image can be obtained.

In contrast, with prior art in which just one component was driven, the positional relationship between the optical fiber tip 20 and the object lens varied with the drive state, so it was difficult of the light emitted from the optical fiber tip 20 to be effectively used by the object lens (that is, the situation was substantially the same as when the aperture is small), and resolution decreased.

Also, with this embodiment, an image of higher resolution can be obtained by increasing the aperture of the object lens 18.

Further, the scanning range in the X direction can be increased by driving at a resonant frequency in the direction in which the drive is high speed, such as the X direction.

Twelfth Embodiment

Figure 46:
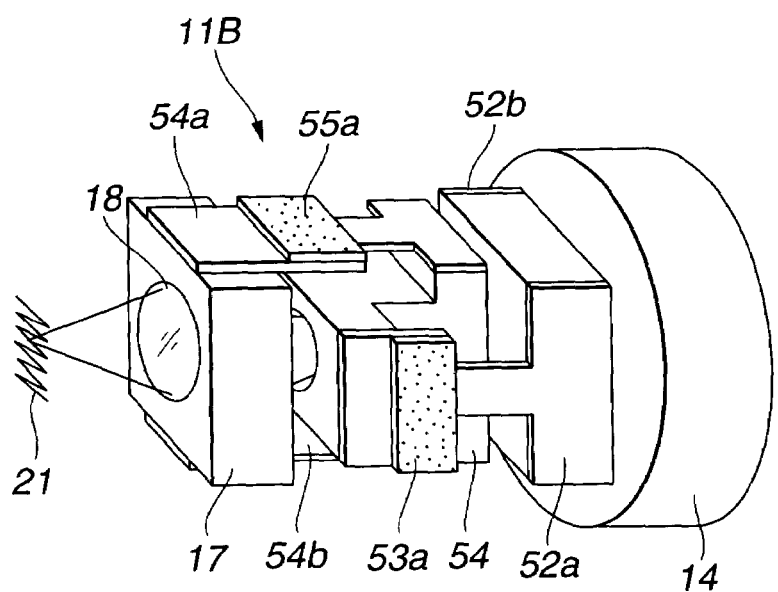

A twelfth embodiment of the present invention will now be described through reference to FIGS. 45 and 46.

This embodiment differs from the eleventh embodiment only in part of the structure of the optical unit 11B provided to the tip component 9. Therefore, those components that are the same as in the eleventh embodiment are labeled the same and will not be described again.

Again in this embodiment, the optical frame 10 is fixed to the tube 8, and the base 14 of the optical unit 11B is fixed to this optical frame 10. The portion of the optical fiber 6b toward the tip is fixed to this base 14. Two parallel thin plates 52a and 52b are also fixed to this base 14.

Piezoelectric elements 53a and 53b are bonded to the thin plates 52a and 52b, respectively, at positions near the tips thereof. (The piezoelectric element 53b provided to the thin plate 52b is on the other side and cannot be seen in FIG. 7.) The distal ends of the thin plates 52a and 52b are fixed to a middle member 54.

The rear ends of two parallel thin plates 54a and 54b are fixed to the top and bottom of this middle member 54. Piezoelectric elements 55a and 55b are bonded to the thin plates 54a and 54b at positions near the tips thereof.

The same lens holder 17 as in the first embodiment is fixed to the distal ends of the thin plates 54a and 54b, and the object lens 18 and optical fiber tip 20 are fixed to the lens holder 17.

The piezoelectric elements 53a and 53b are connected to the X drive circuit 32 via cables 19, and the piezoelectric elements 55a and 55b are connected to the Y drive circuit 33 via cables 19.

In this embodiment, the scanning means scanned in the X and Y directions are longitudinally (serially) connected in the lengthwise direction of the optical probe.

The operation of this embodiment will now be described.

The piezoelectric elements 53a and 53b are driven by the X drive circuit 32, and the focal point 21 is moved in the X direction 22.

The piezoelectric elements 55a and 55b are driven by the Y drive circuit 33, and the focal point 21 is moved in the Y direction 23.

This drive may be performed at the resonant frequency of the system. Everything else is the same as in the eleventh embodiment, and will therefore not be described again.

This embodiment has the following effects.

Thin plates for moving the focal point 21 are provided independently in the X and Y directions, so they do not interfere with each other in their operation, and the focal point 21 can be moved farther than in the eleventh embodiment.

The rest of the effects are the same as in the eleventh embodiment.

A variation example of the twelfth embodiment will now be described.

The thin plate 52b and the piezoelectric element 53b in the twelfth embodiment are eliminated, but the rest of the structure and operation is the same, and will therefore not be described again.

This variation example has the following effects.

Because drive in the X direction is changed from a dual to a single parallel plate structure, greater displacement is possible, and a wider scanning image is obtained by scanning over a wider range.

Also, since the resonant frequency in the X direction can be lowered, a differential can be obtained in the resonant frequencies in the X and Y directions, which reduces the effect that scanning in one direction has on scanning in the other direction.

Thirteenth Embodiment

Figure 47:
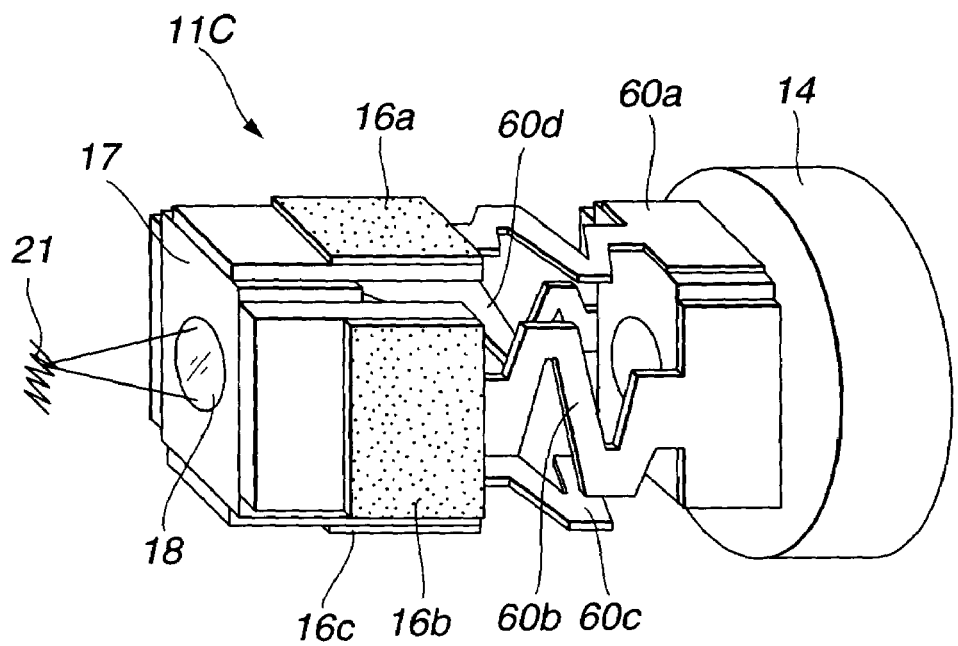
FIG. 47 is a perspective view of the structure of the optical unit provided to the tip of the optical probe in a thirteenth embodiment of the present invention.

A thirteenth embodiment of the present invention will now be described through reference to FIG. 47. FIG. 47 illustrates an optical unit 11C in the thirteenth embodiment.

The structure and operation in this embodiment are the same as in the eleventh embodiment, except that the thin plates 15a, 15b, 15c, and 15d are replaced with thin plates 60a, 60b, 60c, and 60d in a V- or W-shape as shown in FIG. 47, and therefore will not be described again.

This embodiment has the following effect.

The focal point can be moved farther more easily than in the eleventh embodiment, allowing an image to be obtained over a wider scanning range.

Fourteenth Embodiment

Figure 48:
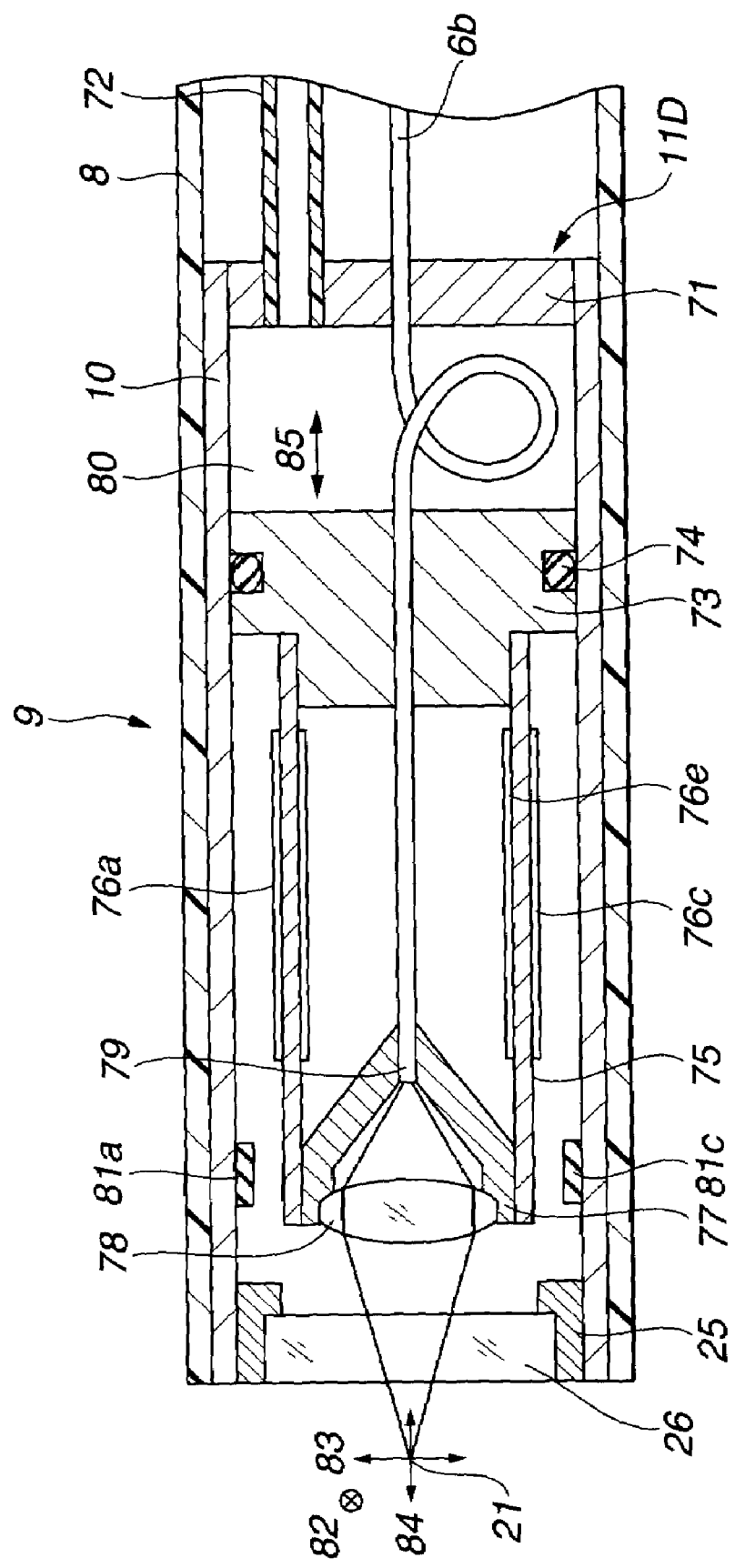

A fourteenth embodiment of the present invention will now be described through reference to FIGS. 48 and 49.

The only difference between this embodiment and the eleventh embodiment is the optical unit 11D of the tip component 9. (Those components that are the same as in the eleventh embodiment are labeled the same and will not be described again.)

Again in this embodiment, the optical frame 10 to which the optical unit 11D is attached is fixed to the tube 8.

A base 71 of the optical unit is fixed to the optical frame 10. The distal end of a tube 72 is bonded to the base 71. The opposite end of the tube 72 is connected to a pneumatic device (not shown).

A movable carriage 73 disposed ahead of the base 71 in the optical frame 10 is slidably attached to the base 71. An O-ring 74 is provided to the movable carriage 73 to make it airtight. Compressed air is injected (pumped) from and drawn back into the pneumatic device via the tube 72, which allows the movable carriage 73 to move back and forth as indicated by 85 in the figure.

Figure 49:
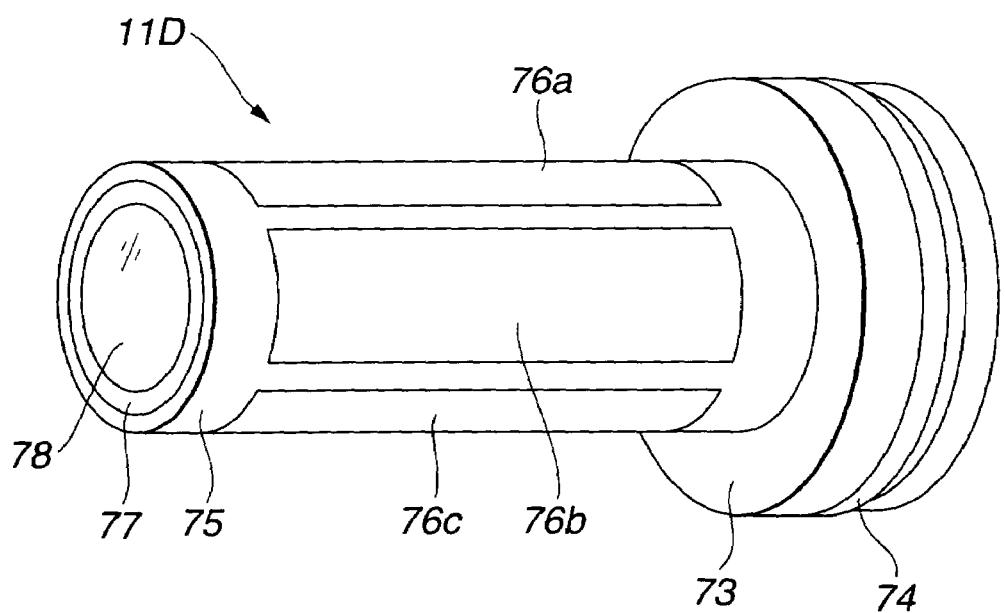
FIGS. 48 and 49 pertain to a fourteenth embodiment of the present invention.

FIG. 49 is a detail view of the area around the movable carriage 73.

A cylindrical piezoelectric element 75 is provided to the movable carriage 73. Four electrodes 76a, 76b, 76c, and 76d are provided to this cylindrical piezoelectric element 75 so as to divide up the periphery into four parts, and an electrode 76e is provided to the inner surface of the piezoelectric element 75. The electrodes are connected to the control component 5 via cables 19.

A lens frame 77 is fixed to the distal end of the cylindrical piezoelectric element 75, and an object lens 78 and an optical fiber tip 79 are fixed to the lens frame 77. The optical fiber 6b is fixed at the sections where it is in contact with holes in the movable carriage 73 and the base 71 as shown in FIG. 48. The optical fiber 6b is looped or otherwise given play in a space 80 between the base 71 and the movable carriage 73.

Rubber cushions 81a, 81b, 81c, and 81d are provided to the optical frame 10 at four places (81b and 81d are not shown). These are designed so that the piezoelectric element 75 will hit the rubber cushions 81i when it is driven far enough that it reaches its stroke limit. The rubber cushions 81i are provided at positions facing the distal end of the piezoelectric element 75.

The operation of this embodiment will now be described.

In the X drive circuit 32, the electrode 76c on the inner surface is grounded, and when alternating current of opposite polarity is applied to the electrodes 76b and 76d, the cylindrical piezoelectric element 75 vibrates and turns in the X direction (because the electrode 76d portion contracts when the electrode 76b portion expands, and the electrode 76b portion contracts when the electrode 76d portion expands). This causes the focal point 21 to vibrate in the X direction 82 direction.

Similarly, in the Y drive circuit 33, the electrode 76c on the inner surface is grounded, and when voltage is applied to the electrodes 76a and 76c, the cylindrical piezoelectric element 75 vibrates in the Y direction 83, causing the focal point 21 also to vibrate in the Y direction 83.

This drive may be performed at the resonant frequency of the system.

Otherwise, scanning is performed in the same manner as in the eleventh embodiment.

The movable carriage 73 can be moved in the axial direction 85 of the optical frame 10 by using the pneumatic device (not shown) to inject air into or draw it from the space 80 via the tube 72.

Along with this, the focal point 21 can be moved in the Z direction 84 of the axial direction 85. As a result, moving the focal point 21 in the Z direction 84 allows images to be obtained at planes of different depth. Also, if these functions are combined, images can be obtained not only at planes perpendicular to the axis of the probe, but also cross sections perpendicular to the axis of the probe, and even cross sections in the diagonal direction.

Even if too much voltage is applied to the piezoelectric element 75, or if the probe is subjected to an impact, the piezoelectric element 75 will hit the rubber cushions 81a, 81b, 81c, and 81d, and the impact will be absorbed, making it less likely that the piezoelectric element 75 will be damaged. These rubber cushions 81a, 81b, 81c, and 81d may also be provided on the piezoelectric element 75 side.

This embodiment has the following effects.

The structure of the scanning means is simpler than in the eleventh embodiment.

Also, since there is a function for moving the focal point 21 in the axial direction of the probe, images of various cross sections can be obtained.

Also, since cushioning members are provided at the stroke end of the piezoelectric element 75, the piezoelectric element 75 is less prone to damage.

Fifteenth Embodiment

A fifteenth embodiment of the present invention will now be described through reference to FIGS. 50 to 53.

Only the portions that are different from the eleventh embodiment are discussed. Those portions that are the same as in the eleventh embodiment are labeled the same and will not be described again.

Figure 50:
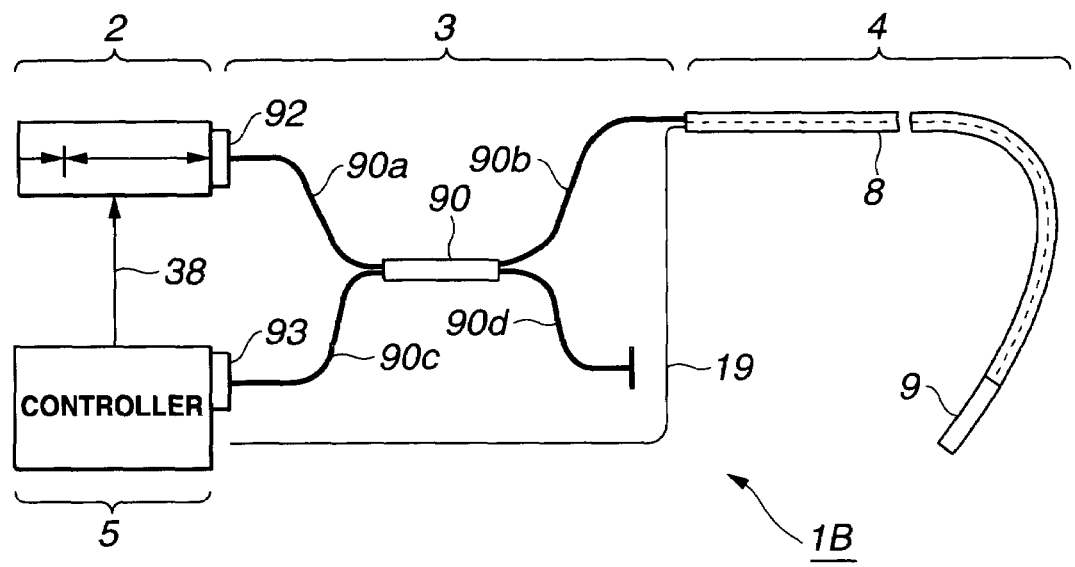
FIGS. 50 to 53 pertain to a fifteenth embodiment of the present invention.

The optical scanning microscope 1B shown in FIG. 50 comprises the light source component 2, the optical transmission component 3, the optical probe 4, and the control component 5, just as in the eleventh embodiment.

The light source component 2 consists of a laser oscillation device, and the optical transmission component 3 comprises optical transmission fibers 90a, 90b, 90c, and 90d and a four-terminal coupler 91 that branches these fibers in two directions. The fibers 90a, 90b, 90c, and 90d are polarization plane-preserving fibers, in which the plane of polarization is preserved.

The fiber 90a is connected to the light source component 2, while the fiber 90c is connected to the control component 5. The fiber 90d is blocked off.

The fiber 90b is long and slender, passing through the inside of the flexible tube 8 of the optical probe 4, and being guided to the tip component 9.

A polarizing plate 92 is disposed in front of a laser light source 2a that constitutes the light source component 2. The light transmitted by the optical fiber 90c is also inputted to the control component 5 via a polarizing plate 93.

The polarizing plates 92 and 93 are disposed such that their polarization planes are at right angles to each other (crossed Nicol state).

Figure 51:
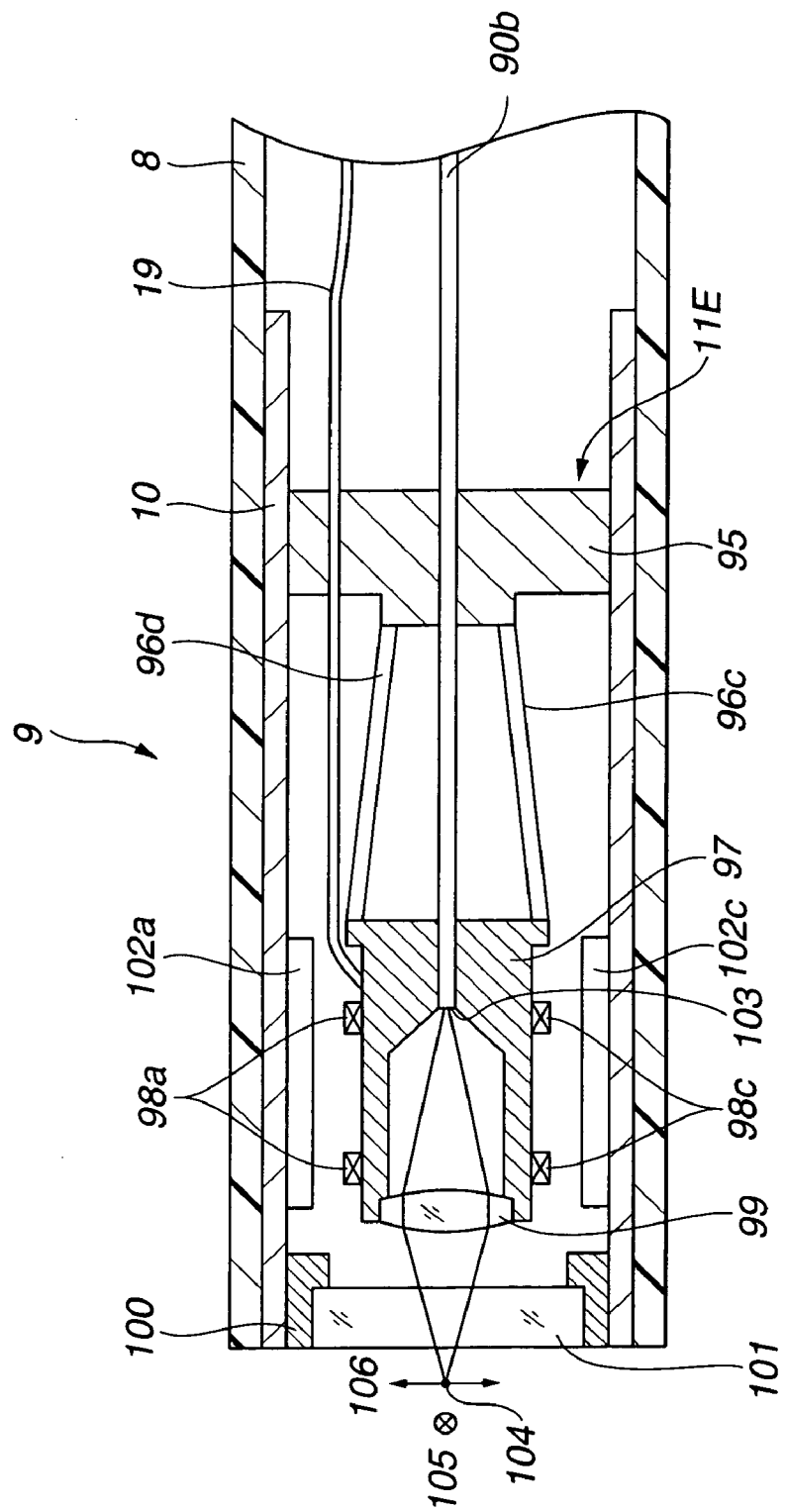
Figure 52:
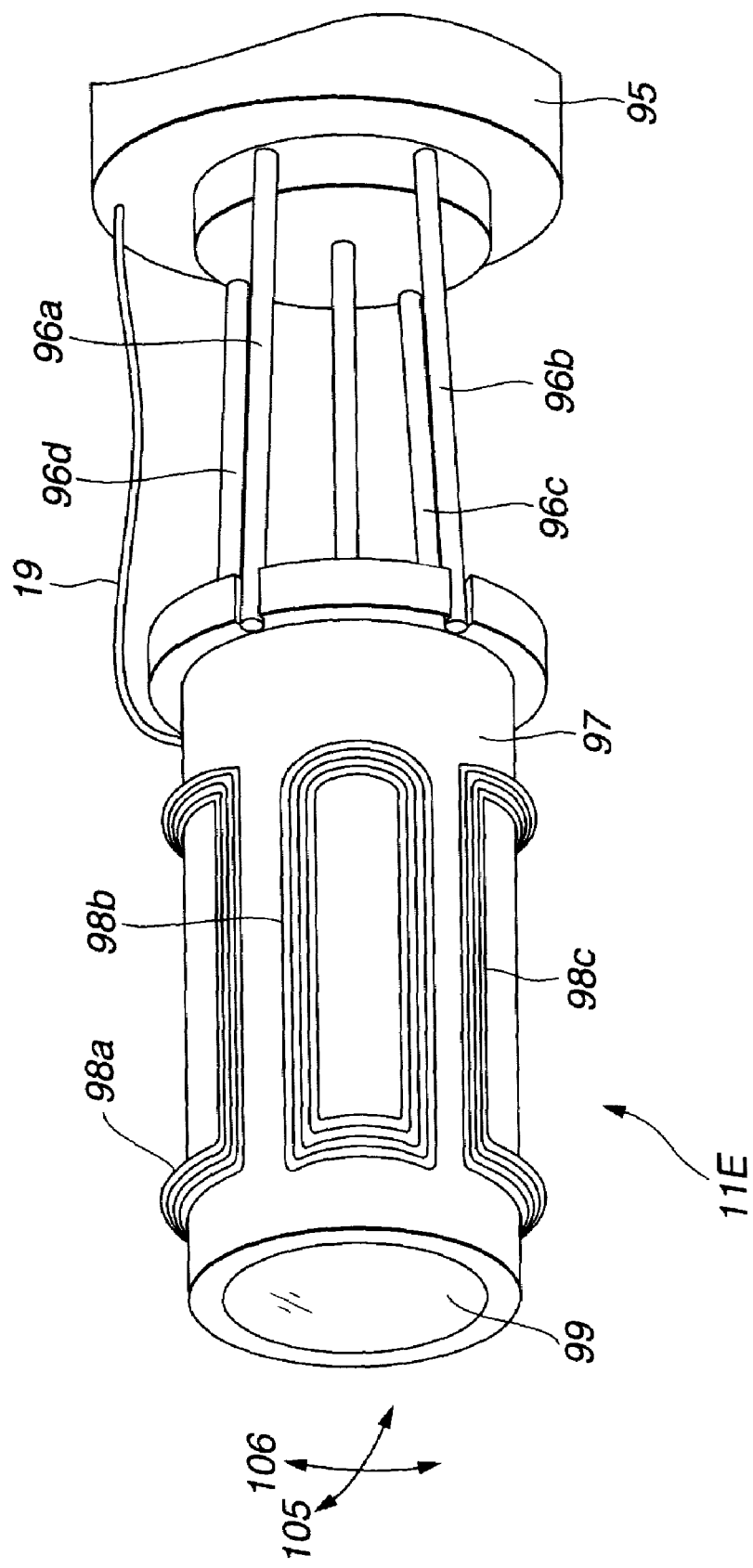

FIG. 51 shows the construction of the tip component 9. In this tip component 9, the optical frame 10 is fixed to the distal end of the tube 8, and an optical unit 11E is attached on the inside of this optical frame 10. FIG. 52 is a perspective view of the optical unit 11E.

The base 95 of the optical unit 11E is fixed to the optical frame 10. The rear ends of four linear members, and more specifically, four wires 96a, 96b, 96c, and 96d, are adhesively fixed to the base 95. A lens frame 97 is fixed to the distal ends of the four wires 96i.

Four coils 98a, 98b, 98c, and 98d that function as voice coils are bonded to this lens frame 97. More specifically, the coils 98a, 98b, 98c, and 98d are bonded above and below and to the left and right of the lens frame 97.

Although not shown, the coil 98d is on the other side from the coil 98b. These coils are connected to the control component 5 via cables 19.

Figure 53:
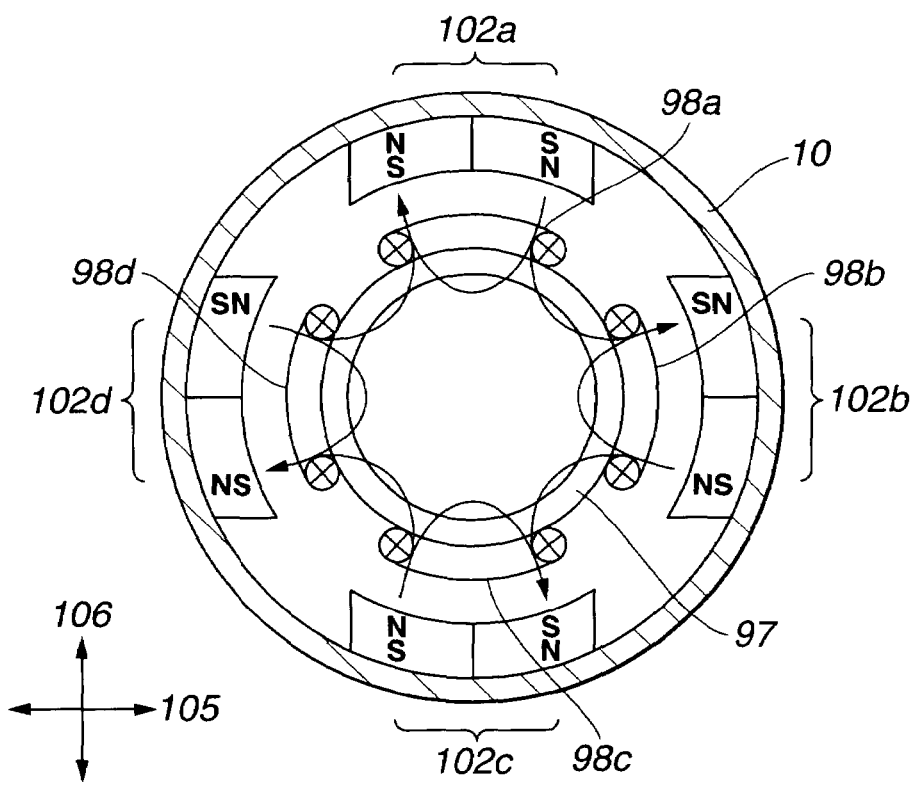

An object lens 99 is fixed to the lens frame 97. Also, four sets of permanent magnets 102a, 102b, 102c, and 102d are adhesively fixed to the optical frame 10 such that they are facing the coils 98a, 98b, 98c, and 98d, respectively. FIG. 53 is a cross section of the permanent magnet portion. The poles of the permanent magnets 102i are arranged as shown.

A wavelength plate holder 100 is fixed to the optical frame 10, and a quarter-wavelength plate 101 is fixed to the wavelength plate holder 100.

The operation of this embodiment will now be described.

Laser light is transmitted by the polarizing plate 92 to the optical fiber 90a, but only light having a specific polarization plane is transmitted, and part of this light is transmitted to the optical fiber 90b. Because these fibers are polarization plane-preserving fibers, the orientation of the polarization is maintained. This light is emitted from the tip face 103 of the fiber 90b.

This light is focused at a focal point 104 by the condensing function of the object lens 99. From this focal point 104, the light travels the same optical path and is incident on the tip face 103 of the optical fiber 90b, but when it passes twice through the quarter-wavelength plate 101, it becomes light having a polarization plane that is perpendicular to that of the light emitted from the fiber.

This light is split by the four-terminal coupler 91 and transmitted to the control component 5 through the optical fiber 90c, but only the light whose polarization direction matches that of the polarizing plate 93 can be transmitted by the polarizing plate 93. Thus, only the signal from the focal point 104 is detected, whereas the polarization plane of the reflected light from the optical fiber tip face 113 and so on does not match, so this light is not transmitted to the control component 5.

In the X drive circuit 32, current crosses the magnetic field when current flows to the coils 98a and 98c, so electromagnetic force, and more specifically, Lorentz's force, comes into play. This force acts in the horizontal direction (X direction) 105 shown in FIG. 51 or 53 and is accompanied by deformation of the wires 96a, 96b, 96c, and 96d, which moves the lens frame 97 in the horizontal direction 105.

This causes the focal point 104 to move in the horizontal direction 105 as well. Here, the focal point 104 can be vibrated in the horizontal direction 105 by applying alternating current to the coils 98a and 98c.

This drive may be performed at the resonant frequency of the system.

Similarly, in the Y drive circuit 33, current flows to the coils 102b and 102d and causes the focal point 104 to vibrate in the vertical direction (Y direction) 106.

Otherwise, scanning is performed in the same manner as in the eleventh embodiment.

This embodiment has the following effects.

The scanning means can operate over a wider range than in the eleventh embodiment.

Also, since polarizing plates are used so that light outside of the focal point tends not to be detected, just the signal can be detected at good sensitivity, allowing an image with a good S/N ratio, that is good quality, to be obtained.

Embodiments in which the various embodiments given above are partially or otherwise combined are also included in the present invention.

The invention claimed is:

1. An optical scanning probe system (111), comprising:
 a mounting component (119, 122) for detachably mounting at least one of a plurality of types of optical scanning probes (112A, 112B) having scanning components (16a, 16c, 16b) for scanning an examination site with the focal point of observation light emitted by a light source device (113);
 a recognition component (131) for recognizing the type of optical scanning probe mounted to the mounting component (119); and
 a control device (130) for controlling the scanning components (16a, 16c, 16b) in the optical scanning probe according to the type of the optical scanning probe recognized by the recognition component (131).

2. An optical scanning probe device in which an examination site is scanned with the focal point of observation light emitted by a light source device (113), and the observation light reflected from the examination site as a result of the scanning is transmitted to observation devices (113, 114, 115), comprising:
 a transmission member (6b) for transmitting the observation light emitted by the light source device (113) and emitting said observation light from an end face, and receiving at this end face the observation light reflected from the examination site and transmitting same to the observation devices (113, 114, 115);
 a condensing optical system (18) for condensing the observation light emitted from the end face of the transmission member (6b);
 a fixing member (17) for fixing the condensing optical system (18) along with the end face of the transmission member (6b); and
 scanning components (16a, 16c, 16b) for moving the fixing member (17) and scanning the examination site with the focal point of the observation light.

3. An optical scanning probe device according to claim 2, wherein the scanning components (16a, 16c, 16b) comprise:
 first movement devices (16a, 16c) for moving the fixing member (17) in a specific first direction; and
 a second movement device (16b) for moving the fixing member in a second direction that differs from the first direction.

4. An optical scanning probe device in which an examination site is scanned with the focal point of observation light emitted by a light source device (113), and the observation light reflected from the examination site as a result of the scanning is transmitted to observation devices (113, 114, 115), comprising:
 a transmission member (6b) for transmitting the observation light emitted by the light source device (113) and emitting said observation light from an end face, and receiving at this end face the observation light reflected from the examination site and transmitting same to the observation devices; and
 a condensing optical system (18) for condensing the observation light emitted from the end face of the transmission member (6b),
 wherein the relative positions of the condensing optical system (18) and the end face of the transmission member (6b) are maintained during scanning.

5. An optical scanning probe system, comprising:
 a light source device (113) for emitting observation light;
 an optical fiber (6b) for transmitting the observation light;
 a photocoupler (125) for guiding the observation light to the emitting terminal side of the optical fiber (6b) and guiding the return light coming in from the base side of the optical fiber (6b) to a photodetector side;
 a photodetector (124) for detecting the return light and subjecting it to photo-electric conversion;
 an optical scanning probe (112A) having scanners (16a, 16c, 16b) for integrally scanning an object lens (18) and the tip of the optical fiber (6b) positioned facing each other at the emitting terminal of the optical fiber (6b), and scanning the focal position in a confocal relationship with the emitting terminal of the optical fiber (6b);
 an imaging device (115) for performing signal processing that images the output signal of the photodetector (124);
 scanner drivers (148, 149) for driving the scanners (16a, 16c, 16b); and
 a display device (116) for displaying the output signal of the imaging device (115).

6. An optical scanning probe device, wherein at least the emitting terminal of an optical fiber (6b) and an object lens (203) are integrally fixed, and a reflection member (202) is provided so that the emitted light is reflected laterally and the return light thereof is detected.

7. An optical scanning probe device structured such that at least the emitting terminal of an optical fiber (6*b*) and object lenses (18, 241) are integrally fixed, and tip cover glasses (225, 234) of the optical scanning probe doing the scanning have an angle that is not perpendicular to the optical axis.

8. An optical scanning probe device, wherein a tip cover glass (234) of an optical scanning probe has an angle that is not perpendicular to the axis of the optical scanning probe, and two-dimensional scanners (239*a*, 239*c*, 239*d*) are structured such that their optical axes are perpendicular to this cover glass (234).

9. An optical scanning probe device comprising a probe (8) inserted into a body cavity, light sources (123, 2) for irradiating an examination site with light, an optical fiber (6*b*) for guiding the light from the light sources (123, 2) to the probe (8) tip, a focusing optical system (18) for focusing the light from the optical fiber (6*b*) onto the examination site and condensing the light from the examination site onto the end face of the optical fiber (6*b*), optical scanning components (16*a*, 16*c*, 16*b*) for scanning the examination site with the focal point focused by the focusing optical system (18), separating devices (125, 7) for separating at least a portion of the return light coming from the examination site from the optical path of the light coming from the light sources (123, 2), and photodetectors (124, 34) for detecting the separated light,
wherein the scanning components (16*a*, 16*c*, 16*b*) integrally scan the condensing optical system (18) and the optical fiber (6*b*) tip in a probe tip (9).

10. The optical scanning probe device according to claim 9, wherein the scanning components (16*a*, 16*c*, 16*b*) scan the focal point in at least two directions.

11. The optical scanning probe device according to claim 9, wherein the scanning components (55*a*, 55*b*, 55*c*) have two differently orientated scanning components which are connected serially.

12. The optical scanning probe device according to claim 9, wherein at least one (16*b*) of the scanning components (16*a*, 16*c*, 16*b*) is driven at a resonant frequency.

13. The optical scanning probe device according to claim 9, wherein the scanning components (16*a*, 16*c*, 16*b*) have at least one deformation component (15*a*, 15*c*, 15*b*) of low rigidity.

14. The optical scanning probe device according to claim 13, wherein the deformation components have parallel plate structures (15*a*, 15*c*, 15*b*, 15*d*).

15. The optical scanning probe device according to claim 13, wherein the deformation components are structured as linear members (96*a*, 96*b*, 96*c*, 96*d*).

16. The optical scanning probe device according to claim 9, wherein the probe tip (9) has a sealed construction.

17. The optical scanning probe device according to claim 9, wherein the scanning components (16*a*, 16*c*, 16*b*) are scanned within the sealed portion, and the exterior part of the probe tip does not move.

18. The optical scanning probe device according to claim 9, wherein the probe (8) has a base (14) for fixing the scanning components (15*a*, 15*c*, 15*b*).

19. The optical scanning probe device according to claim 18, wherein the base (14) is heavier than the lens (18) to be scanned.

20. The optical scanning probe device according to claim 18, wherein a portion of the optical fiber (6*b*) is fixed to the base (14).

21. The optical scanning probe device according to claim 9, wherein impact cushioning devices (81*a*, 81*c*) are provided in the stroke ends of the scanning range of the scanning components (76*a*, 76*c*, 76*b*).

22. The optical scanning probe device according to claim 9, provided with a device (45) for fixing the area close to the probe tip (9) to an endoscope.

23. The optical scanning probe device according to claim 9, wherein the scanning components (76*a*, 76*c*, 76*b*) have a member (73) for moving the focal point in the axial direction of the probe.

24. The optical scanning probe device according to claim 9, wherein the optical fiber is a single-mode fiber (6*b*).

25. The optical scanning probe device according to claim 9, wherein the optical fiber is a multi-mode fiber.

26. The optical scanning probe device according to claim 9, wherein the optical fiber is a polarization plane-preserving fiber (90*b*).

27. An optical scanning probe device in which observation light emitted by a light source device (113) is condensed by a specific lens (18), and the focal point of said observation light is scanned with respect to an examination site, comprising:
a single first deformation component (163*a*) deformable in a specific first direction;
a single second deformation component (163*b*) connected via a connecting component (163*c*) to one end of the first deformation component (163*a*) and deformable in a second direction that is perpendicular to the first direction;
a fixing component connected to the other end of the first deformation component (163*a*) with respect to the end with the connecting component (163*c*), for fixing the first deformation component (163*a*) to a probe unit (165) side;
a condenser fixing component (168*a*) formed on the other end of the second deformation component (163*b*) with respect to the end with the connecting component (163*c*), for fixing a condenser (166) that condenses observation light emitted by the light source device (113) to the second deformation component (163*b*);
a first drive device (164*a*) provided in the first deformation component (163*a*) and able to drive in the first direction; and
a second drive device (164*b*) provided to the second deformation component (163*b*) and able to drive in the second direction.

28. An optical probe device, in which an examination site is scanned with the focal point of observation light emitted by a light source device (113),
wherein a first deformation component (163*a*) and a second deformation component (163*b*) are formed by forming a cut-out groove (163*d*) of a specific width in an elastic plate that is elastically deformable within a specific range, while leaving a portion uncut to form a connecting component (163*c*), the connecting component (163*c*) is bent such that the deformation direction of the first deformation component (163*a*) is perpendicular to the deformation direction of the second deformation component (163*b*),
the other end of the first deformation component (163*a*) with respect to the end with the connecting component (163*c*) is fixed on the probe unit (165) side, and
a condenser (166) that condenses the observation light emitted by the light source device (113) is disposed on the other end of the second deformation component (163*b*) with respect to the end with the connecting component (163*c*).

29. An optical scanning probe device having a two-dimensional scanner for two-dimensionally scanning an optical fiber (6b),
  wherein the two-dimensional scanner is operatively connected to the optical fiber and has a first set of parallel plate structures (16a, 16c) for scanning in a first direction and a second set of parallel plate structures (16b, 16d) for scanning in a second direction.

30. An optical scanning probe device, having a two-dimensional scanner with which at least the emitting terminal of an optical fiber (6b) and an object lens (203) are integrally fixed and integrally subjected to two-dimensional scanning,
  wherein the two-dimensional scanner is operatively connected to the optical fiber and has a first set of parallel plate structures (16a, 16c) for scanning in a first direction and a second set of parallel plate structures (16b, 16d) for scanning in a second direction.

31. The optical scanning probe device according to claim 29, wherein the first and second sets of parallel plate structures (16a, 16c; 16b, 16d) are each linked by an intermediate member (311).

32. The optical scanning probe device according to claim 30, wherein the first and second sets of parallel plate structures (16a, 16c; 16b, 16d) are each linked by an intermediate member (311).

33. An optical scanning probe device having a two-dimensional scanner with which just an optical fiber (437) is two-dimensionally scanned, or at least the emitting terminal of the optical fiber (437) and an object lens (435) are integrally fixed and integrally subjected to two-dimensional scanning,
  wherein the two-dimensional scanner comprises two plate-form actuators (433, 440) each scanning in a different direction and an intermediate member (434), the tip end side of the plate-form actuator (433) fixed on the proximal side of the two-dimensional scanner is fastened on the tip end of the intermediate member (434), and the proximal side of the plate-form actuator (440) disposed on the tip end side of the two-dimensional scanner is fastened on the proximal side of the intermediate member (434).

34. The optical scanning probe device according to claim 33, wherein an electrode is soldered at the portion located at the fixed part of the plate-form piezoelectric actuator (440).

35. An optical scanning probe device having a two-dimensional scanner with which just an optical fiber (437) is two-dimensionally scanned, or at least the emitting terminal of the optical fiber (437) and an object lens (435) are integrally fixed and integrally subjected to two-dimensional scanning,
  wherein the two-dimensional scanner comprises a set of parallel plate structure actuators (453a, 454a, 453b, 454b), plate-form actuators (455, 456), and an intermediate member (434), the proximal side of the plate-form actuators (455, 456) is fixed to the near fixed part (432) side of the two-dimensional scanner, the tip end side of the plate-form actuators (455, 456) is fixed to the tip end side of the intermediate member (434), the proximal side of the parallel plate structure actuators (453a, 454a, 453b, 454b) is fixed to the proximal side of the intermediate member (434), and the tip end side of the parallel plate structure actuators (453a, 454a, 453b, 454b) is fixed to the optical fiber (434), or to the optical fiber (434) and the object lens (435).

36. An optical scanning probe device having a two-dimensional scanner with which just an optical fiber (167) is two-dimensionally scanned, or at least the emitting terminal of the optical fiber (167) and an object lens (166) are integrally fixed and integrally subjected to two-dimensional scanning,
  wherein the two-dimensional scanner comprises two unimorphs in which two piezoelectric elements (164a, 164b) are bonded to a single bending plate (163a, 163b) having a slit (163d), with the slit (163d) interposed in between.

37. An optical scanning probe device having a two-dimensional scanner with which just an optical fiber (167) is two-dimensionally scanned, or at least the emitting terminal of the optical fiber (167) and an object lens (166) are integrally fixed and integrally subjected to two dimensional scanning,
  wherein the two-dimensional scanner comprises two bimorphs in which two piezoelectric elements (164a, 164a'; 164b, 164b') are bonded to both sides of a single bending plate (163a, 163b) having a slit (163d), with the slit (163d) interposed in between.

38. An optical scanning probe device having a two-dimensional scanner with which just an optical fiber (167) is two-dimensionally scanned, or at least the emitting terminal of the optical fiber (167) and an object lens (166) are integrally fixed and integrally subjected to two-dimensional scanning,
  wherein the two-dimensional scanner comprises two plate-form piezoelectric actuators (163a, 164a; 163b, 164b), and the lengths of the piezoelectric elements are different.

39. An optical scanning probe device having a two-dimensional scanner (415) with which the emitting terminal of an optical fiber (412), or the emitting terminal of the optical fiber (412) and an object lens are integrally subjected to two-dimensional scanning,
  wherein the optical fiber (412) and a fixed part (419) of the optical scanning probe are located where vibration produced by the two-dimensional scanner is not transmitted.

40. An optical scanning probe device having a two-dimensional scanner with which the emitting terminal of an optical fiber (6b), or the emitting terminal of the optical fiber (6b) and an object lens (18) are integrally subjected to two-dimensional scanning,
  wherein a fixed part (27) of the optical scanning probe and the optical fiber (6b) are located inside the hard tip (9) of the optical scanning probe.

41. An optical scanning probe device having a two-dimensional scanner (415) with which the emitting terminal of an optical fiber (412), or the emitting terminal of the optical fiber (412) and an object lens are integrally subjected to two-dimensional scanning,
  wherein a fixed part (419) of the optical scanning probe and the optical fiber (412) are located to the rear by at least the same length as the two-dimensional scanner.

42. An optical scanning probe device having a two-dimensional scanner (415) with which the emitting terminal of an optical fiber (412), or the emitting terminal of the optical fiber (412) and an object lens are integrally subjected to two-dimensional scanning,
  wherein a fixed part (419) of the optical scanning probe and the optical fiber (412) are located at a position corresponding to an integer multiple of the length of the two-dimensional scanner.

43. An optical scanning probe device having a two-dimensional scanner (415) with which the emitting terminal of an optical fiber (412), or the emitting terminal of the optical fiber (412) and an object lens are integrally subjected to two-dimensional scanning, wherein slack (420) is provided to the optical fiber (412) on the tip end side from the location of a fixed part (419) of the optical fiber (412).

44. An optical scanning probe device having a two-dimensional scanner with which the emitting terminal of an optical fiber (6b), or the emitting terminal of the optical fiber (6b) and an object lens (18) are integrally subjected to two-dimensional scanning, wherein a barrier (14b) is formed between the optical fiber (6b) and a signal line (19) that drives the two-dimensional scanner.

45. An optical scanning probe device having a two-dimensional scanner with which the emitting terminal of an optical fiber (6b), or the emitting terminal of the optical fiber (6b) and an object lens (18) are integrally subjected to two-dimensional scanning, wherein a signal line (19) that drives the two-dimensional scanner is fixed at the rear end (28) of the two-dimensional scanner.

46. An optical scanning probe device having a two-dimensional scanner with which the emitting terminal of an optical fiber (6b), or the emitting terminal of the optical fiber (6b) and an object lens (18) are integrally subjected to two-dimensional scanning, wherein provision is made such that a signal line connected to the two-dimensional scanner does not come into contact with the optical fiber (6b) on the tip end from a fixed part (28) thereof.

47. An optical scanning probe device comprising a probe (8) with a built-in scanner that is reciprocally driven, a control device (114) for driving the scanner, a light source (123) for irradiating an examination site with light, an optical fiber (6b) for guiding the light from the light source (123) to the probe tip, a focusing optical system (18) for focusing the light from the optical fiber (6b) on the examination site and condensing the light from the examination site on the end face of the optical fiber (6b), a separating device (125) for separating at least a portion of the return light coming from the examination site from the optical path of the light coming from the light source (123), a detector (124) for detecting the separated light, and an imaging device (115) for imaging the signal from the detector (124) and displaying the image on a display device (116), wherein the imaging device (115) has image synthesizers (140, 141, 142, 144, 150, 252, 253) for synthesizing forward path and backward path images.

48. The optical scanning probe device according to claim 47, wherein the image synthesizers have a first frame memory (252) for storing forward path images, a second frame memory (253) for storing backward path images, and a characteristic correction device (150) for matching to the hysteresis characteristics of either the forward path or the backward path, or both.

49. The optical scanning probe device according to claim 48, wherein the characteristic correction device (150) comprises a reference table including the deviation from the forward path, a hysteresis correction coefficient, and the deviation from the backward path, uniquely corresponding to the values of the drive voltage at which the scanner is driven.

50. An optical scanning probe device comprising a probe (8) with a built-in scanner that is reciprocally driven, a control device (114) for driving the scanner, a light source (123) for irradiating an examination site with light, an optical fiber (6b) for guiding the light from the light source (123) to the probe tip, a focusing optical system (18) for focusing the light from the optical fiber (6b) on the examination site and condensing the light from the examination site on the end face of the optical fiber (6b), a separating device (125) for separating at least a portion of the return light coming from the examination site from the optical path of the light coming from the light source (123), a detector (124) for detecting the separated light, and an imaging device (115) for imaging the signal from the detector (124) and displaying the image on a display device (116), wherein the scanner has a scanning position correction device (302) for making the forward and backward path scanning positions coincide with the scanning position of either the forward path or the backward path.

51. The optical scanning probe device according to claim 50, wherein the imaging device (115) has a drive signal correction circuit (309) for receiving a signal from the position correction device (302) and correcting the drive signal that drives the scanner.

52. An optical scanning probe device comprising:

a probe (8) with a built-in scanner that is driven by a non-linear drive signal;

a control device (114) for driving the scanner;

a light source (123) for irradiating an examination site with light;

an optical fiber (6b) for guiding the light from the light source (123) to the probe tip;

a focusing optical system (18) for focusing the light from the optical fiber (6b) on the examination site and condensing the light from the examination site on the end face of the optical fiber (6b);

a separating device (125) for separating at least a portion of the return light coming from the examination site from the optical path of the light coming from the light source (123);

a detector (124) for detecting the separated light; and an imaging device (115) for imaging the signal from the detector (124) and displaying the image on a display device (116), wherein the imaging device (115) has a linear correction device for the linear correction of the image displayed on the display device (116), and the linear correction device is equipped with a non-linear drive signal generator for generating these non-linear drive signals, an aperiodic pulse generator for generating aperiodic pulses, and an A/D converter (140) for subjecting these aperiodic pulses to A/D conversion as sampling clock signals.

53. A confocal optical scanning probe device comprising a probe (8) having a reciprocally driven scanner, a control device (114) for driving the scanner, a light source (123) for irradiating an examination site with light, an optical fiber (6b) for guiding the light from the light source (123) to the probe tip, a focusing optical system (18) for focusing the light from the optical fiber (6b) on the examination site and condensing the light from the examination site on the end face of the optical fiber (6b), a separating device (125) for separating at least a portion of the return light coming from the examination site from the optical path of the light coming from the light source (123), a detector (124) for detecting the separated light, and an imaging device (115) for imaging the signal from the detector (124) and displaying the image on a display device (116), wherein the imaging device (115) has a one-way direction display device for displaying only the image of the forward path or the backward path.

54. A confocal optical scanning probe device comprising:
a probe (8) with a built-in scanner that is driven by a non-linear drive signal;
a control device (114) for driving the scanner;
a light source (123) for irradiating an examination site with light;
an optical fiber (6*b*) for guiding the light from the light source (123) to the probe tip;
a focusing optical system (18) for focusing the light from the optical fiber (6*b*) on the examination site and condensing the light from the examination site on the optical fiber end face;
a separating device (125) for separating at least a portion of the return light coming from the examination site from the optical path of the light coming from the light source (123);
a detector (124) for detecting the separated light; and
an imaging device for A/D converting and imaging the signal from the detector (124) and displaying the image on a display device,
wherein the imaging device (115) has a display timing device for displaying an image by adjusting the phase of the A/D converted sampling pulses with respect to the non-linear drive waveform, and the display timing device shifts the phase of the sampling pulses by 90° with respect to the non-linear drive waveform.

55. A confocal optical scanning probe device comprising:
a probe (8) with a built-in scanner that is driven by a non-linear drive signal;
a control device (114) for driving the scanner;
a light source (123) for irradiating an examination site with light;
an optical fiber (6*b*) for guiding the light from the light source (123) to the probe tip;
a focusing optical system (18) for focusing the light from the optical fiber (6*b*) on the examination site and condensing the light from the examination site on the optical fiber end face;
a separating device (125) for separating at least a portion of the return light coming from the examination site from the optical path of the light coming from the light source (123);
a detector (124) for detecting the separated light; and
an imaging device (115) for imaging the signal from the detector (124) and displaying the image on a display device (116),
wherein the imaging device (115) has a frame memory (141) for storing the image as line data, and a line interpolator for interpolating the line data stored in the frame memory (141),
the line interpolator has a thinning device for reading the line data from the frame memory (141) thinned to an integer fraction, and a copier for copying to a plural multiple the line data read by the imaging device, and
the number of lines of line data stored in the frame memory is the same as the number of lines of line data copied by the copier.

56. An observation method in which the force with which the tip of an optical scanning probe (112A, 112B) is pressed against an examination site is adjusted to adjust the observation depth, and the angle at which this tip is pressed is adjusted to adjust the angle of the observation plane.

\* \* \* \* \*